(12) United States Patent
Shum et al.

(10) Patent No.: US 12,102,652 B2
(45) Date of Patent: Oct. 1, 2024

(54) CONSTITUTIVELY ACTIVE CYTOKINE RECEPTORS FOR CELL THERAPY

(71) Applicant: Baylor College of Medicine, Houston, TX (US)

(72) Inventors: Thomas C. T. Shum, Houston, TX (US); Stephen M. G. Gottschalk, Houston, TX (US); Bilal Omer, Houston, TX (US); Cliona M. Rooney, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 1071 days.

(21) Appl. No.: 16/326,270

(22) PCT Filed: Aug. 11, 2017

(86) PCT No.: PCT/US2017/046588
§ 371 (c)(1),
(2) Date: Feb. 18, 2019

(87) PCT Pub. No.: WO2018/038945
PCT Pub. Date: Mar. 1, 2018

(65) Prior Publication Data
US 2019/0183936 A1 Jun. 20, 2019

Related U.S. Application Data

(60) Provisional application No. 62/380,021, filed on Aug. 26, 2016.

(51) Int. Cl.
| | | |
|---|---|---|
| *C07K 14/715* | (2006.01) | |
| *A61K 35/12* | (2015.01) | |
| *A61K 35/17* | (2015.01) | |
| *A61K 39/00* | (2006.01) | |
| *A61P 35/00* | (2006.01) | |
| *C07K 14/00* | (2006.01) | |
| *C07K 14/47* | (2006.01) | |
| *C07K 14/725* | (2006.01) | |
| *C12N 15/85* | (2006.01) | |
| *A61K 38/00* | (2006.01) | |

(52) U.S. Cl.
CPC .............. *A61K 35/17* (2013.01); *A61K 35/12* (2013.01); *A61K 39/001119* (2018.08); *A61P 35/00* (2018.01); *C07K 14/00* (2013.01); *C07K 14/4748* (2013.01); *C07K 14/7051* (2013.01); *C07K 14/715* (2013.01); *C07K 14/7155* (2013.01); *C12N 15/85* (2013.01); *A61K 38/00* (2013.01)

(58) Field of Classification Search
CPC .......... A61K 39/001119; C07K 14/715; C07K 14/7155
USPC ........................................................ 930/260
See application file for complete search history.

(56) References Cited

U.S. PATENT DOCUMENTS

| | | | |
|---|---|---|---|
| 8,399,645 B2 | 3/2013 | Campana et al. | |
| 10,548,921 B2* | 2/2020 | Leen ..................... | A61P 35/00 |
| 11,219,646 B2* | 1/2022 | Kruse ................. | C07K 14/7051 |
| 11,717,538 B2* | 8/2023 | Leen .............. | A61K 39/001188 |
| | | | 435/372 |
| 2012/0282258 A1* | 11/2012 | Weinstock .............. | A61P 35/02 |
| | | | 435/6.12 |
| 2014/0050709 A1 | 2/2014 | Leen et al. | |
| 2014/0219975 A1† | 8/2014 | June | |
| 2020/0002402 A1* | 1/2020 | Emtage ............ | C07K 14/70521 |
| 2020/0197437 A1* | 6/2020 | Leen .............. | A61K 39/001186 |

FOREIGN PATENT DOCUMENTS

| | | | |
|---|---|---|---|
| JP | 2015513394 | * | 5/2014 |
| JP | 6850528 B2 | * | 3/2021 |
| WO | WO 2010085643 | * | 7/2010 |
| WO | 2012/138858 A1 | | 10/2012 |
| WO | 2013/123061 A1 | † | 8/2013 |
| WO | 2013/153391 A1 | † | 10/2013 |
| WO | 2014/172584 A1 | | 10/2014 |
| WO | 2016/061574 A1 | | 4/2016 |
| WO | 2017/165245 A2 | † | 9/2017 |
| WO | 2018038945 A1 | | 3/2018 |

OTHER PUBLICATIONS

Leen et al. (Molecular Therapy vol. 22 No. 6, 1211-1220 (Jun. 2014)).*
Lange et al (Cancer Discov Jul. 2021;11(7):1661-1671. Epub Feb. 9, 2021).*
Mohammed et al (Mol Ther. Jan. 4, 2017; 25(1): 249-258).*
McClure et al (Cytokine, vol. 13, No. 4 (Feb. 21), 2001: pp. 240-243).*
Takagi et al (Molecular Biology of the Cell vol. 10, 3633-3642, Nov. 1999).*
Giese et al (J Cell Sci. Nov. 1, 2005;118(Pt 21):5129-40).*
Shikama et al (Blood Jul. 15, 1996;88(2):455-64).*
Behrmann et al (JBC vol. 272, No. 8, Issue of Feb. 21, pp. 5269-5274, 1997).*

(Continued)

*Primary Examiner* — Lynn A Bristol
(74) *Attorney, Agent, or Firm* — Norton Rose Fulbright US LLP

(57) ABSTRACT

Embodiments of the disclosure include methods and compositions for enhancing expansion of immune cells for immunotherapy. In particular embodiments, immune cells, such as T-cells, express a constitutively active cytokine receptor in which the transmembrane and endodomains are able to provide an activating signal separately from any input to the corresponding exodomain to which they are operably linked. In specific embodiments, the transmembrane and endodomain from IL-7Rα is utilized with the exodomain of CD34.

21 Claims, 40 Drawing Sheets

Specification includes a Sequence Listing.

(56) References Cited

OTHER PUBLICATIONS

Morgan (Mol Ther Jun. 2014;22(6):1073-1074).*
ncbi.nlm.nih.gov/gene/3575 (IL7R); p. 1-8; Jun. 16, 2023.*
Toh et al. (Cellular & Molecular Immunology (2013) 10, 379-382).*
Gaffen (Nat Rev Immunol. Aug. 2009 ; 9(8): 556).*
Clinicaltrials.gov (Baylor College; NCT03403036; publication date Jan. 18, 2018).*
Igelmann et al. (Cancers 2019, 11, 1428; Published: Sep. 25, 2019).*
Shochat et al., "Gain-of-function mutations in interleukin-7 receptor-alpha (IL7R) in childhood acute lymphoblastic eukemias", The Journal of Experimental Medicine, vol. 208, No. 5, May 2, 2011 (May 2, 2011), pp. 901-908.
Shum et al., "Constitutive Signaling from an Engineered IL7 Receptor Promotes Durable Tumor Elimination by Tumor-Redirected T Cells", Cancer Discovery, vol. 7, No. 11, Nov. 1, 2017 (Nov. 1, 2017), pp. 1238-1247.
Zenatti et al., "Oncogenic IL7R gain-of-function mutations in childhood T-cell acute lymphoblastic leukemia", Nature Genetics., vol. 43, No. 10, Oct. 1, 2011 (Oct. 1, 2011), pp. 932-939, New York, US.
McElroy et al. "Structural reorganization of the interleukin-7 signaling complex" PNAS, Feb. 14, 2012, vol. 109, No. 7, pp. 2503-2508.
Leen et al: "Reversal of Tumor Immune Inhibition Using a Chimeric Cytokine Receptor", Mol Ther, Mar. 20, 2014, vol. 22, No. 6, pp. 1211-1220.
Lu X et al., "Active conformation of the erythropoietin receptor: random and cysteine-scanning mutagenesis of the extracellular juxtamembrane and transmembrane domains", J Biol Chem, 2006, 281(11):7002-11.
Atanasova M et al., "Understanding Cytokine and Growth Factor Receptor Activation Mechanisms", 2013, HHS Public Access Author Manuscript, NIHMS411101; Crit Rev Biochem Mol Biol. Nov.-Dec. 2012; 47(6): 502-530.
CD52—CAMPATH-1 antigen—*Homo sapiens* (Human) | UniProtKB | UniProt, retrieved Oct. 19, 2023, https://www.uniprot.org/uniprotkb/P31358/entry.
*Homo sapiens* CD52 molecule (CD52), mRNA—Nucleotide—NCBI, retrieved Oct. 20, 2023, https://www.ncbi.nlm.nih.gov/nuccore/NM_001803.3.
Xia et al: "Characterization of the CAMPATH-1 (CDw52) antigen: biochemical analysis and cDNA closing reveal an unusually small peptide backbone", Immunology, vol. 21, Issue 7, Jul. 1991, pp. 1667-1684.
Zeng et al: "Synergy of IL-21 and IL-15 in regulating CD8 T cell expansion and funtion" J Exp Med, Jan. 3, 2005;201 (1):139-48.
Kagoya, et al. "A novel chimeric antigen receptor containing a JAK-STAT signaling domain mediates superior antitumor effects", Nature Medicine. Mar. 2018;24(3):352-359.
Noh et al. 2021, TGF-Beta/IL-7 Chimeric Switch Receptor-Expressing CAR-T Cells Inhibit Recurrence of CD19-Positive B Cell Lymphoma. <https://www.ncbi.nlm.nih.gov/pmc/articles/PMC8395772/>.
Shochat et al., "Novel activating mutations lacking cysteine in type I cytokine receptors in acute lymphoblastic leukemia", Blood 2014;124:106-10.
Tashiro, et al. "Treatment of Acute Myeloid Leukemia with T Cells Expressing Chimeric Antigen Receptors Directed to C-type Lectin-like Molecule 1", Molecular Therapy. Sep. 6, 2017;25(9):2202-2213.
Zhang et al., "The genetic basis of early T-cell precursor acute lymphoblastic leukaemia", Nature 2012;481:157-63.
Quintarelli C. et al., Co-expression of cytokine and suicide genes to enhance the activity and safety of tumor-specific cytotoxic T lymphocytes. Blood, vol. 110, Issue No. 8, pp. 2793-2802 (Oct. 2007).†
Shochat C. et al., Gain-of-function mutations in interleukin-7 receptor-? (IL7R) in childhood acute lymphoblastic leukemias. J Exp Med., vol. 208, Issue No. 5, pp. 901-908 (May 2011).†
Zenatti P. et al., Oncogenic IL7R gain-of-function mutations in childhood T-cell acute lymphoblastic leukemia. Nat Genet., vol. 43, Issue No. 10, pp. 932-939 (Sep. 2011).†

\* cited by examiner
† cited by third party

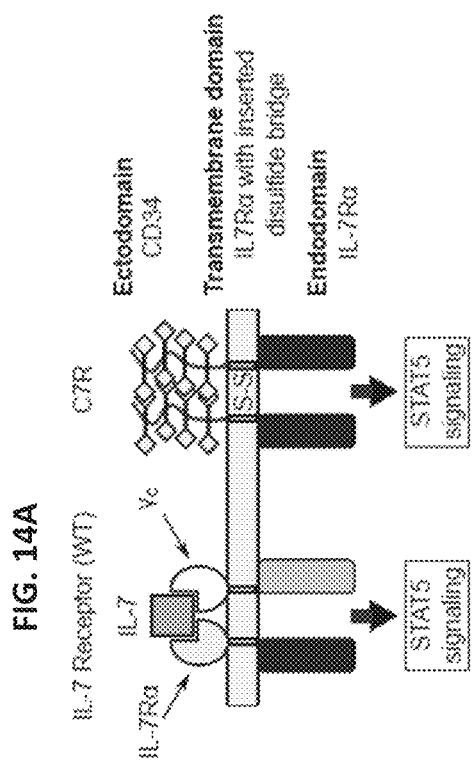

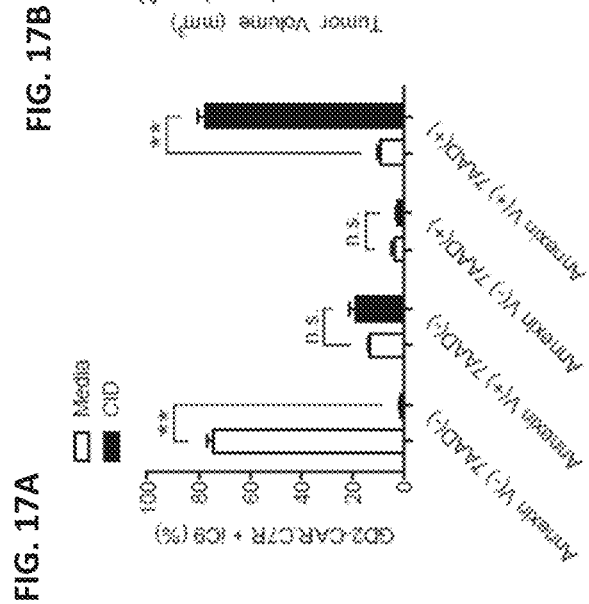
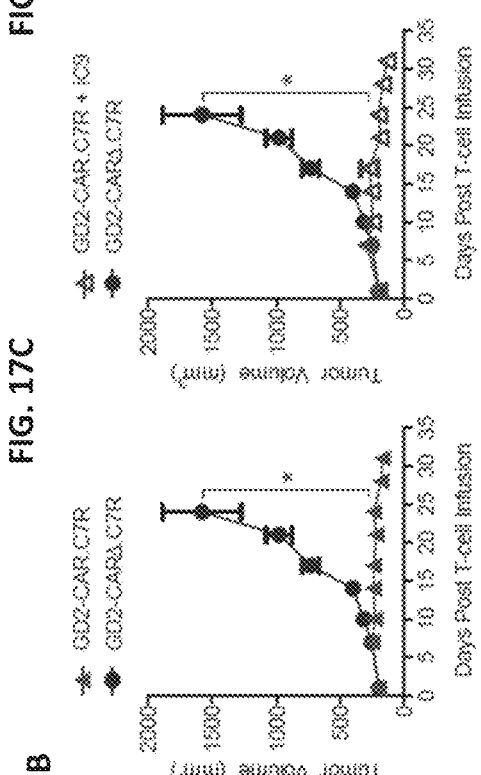
FIG. 17A  FIG. 17B  FIG. 17C  FIG. 17D

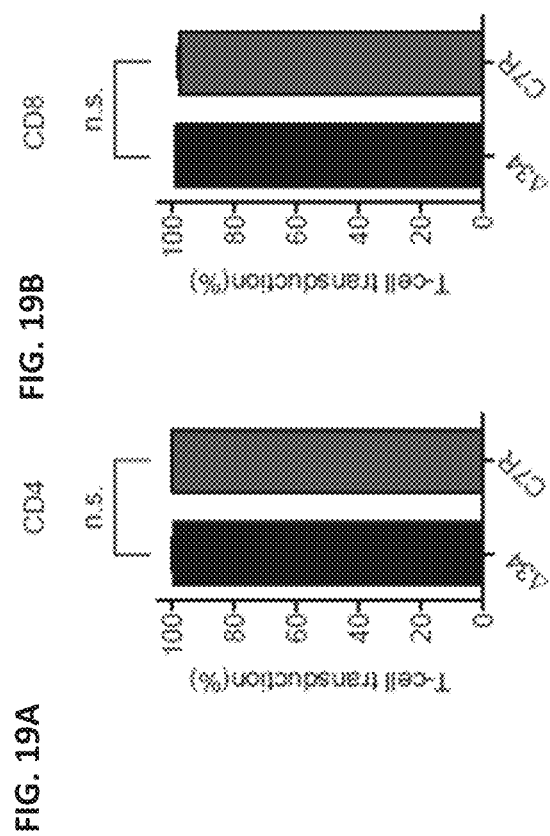

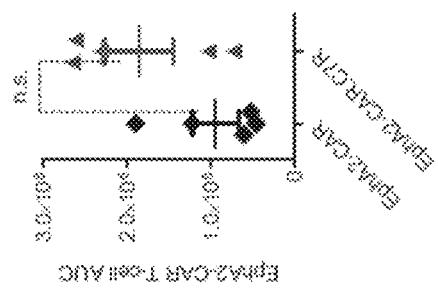
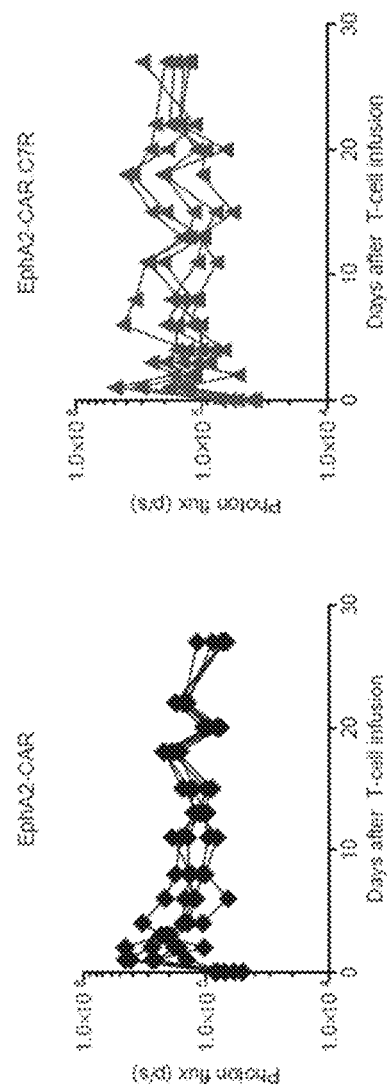
FIG. 21A
FIG. 21B

| Gene Name | P Value | Fold Change | Gene Name | P Value | Fold Change |
|---|---|---|---|---|---|
| SOCS1 | 0.00577 | 2.50472 | IL6ST | 0.00577 | 0.39407 |
| HAVCR2 | 0.00577 | 2.34276 | ABCB1 | 0.00577 | 0.18342 |
| BCL2 | 0.00577 | 2.73604 | CD28 | 0.00577 | 0.12690 |
| NCAM1 | 0.00577 | 6.65741 | CXCL13 | 0.00577 | 0.00690 |
| BATF3 | 0.00587 | 2.73369 | CTSG | 0.00577 | 0.06024 |
| FCGR2A | 0.00697 | 5.25978 | S1PR1 | 0.00577 | 0.25211 |
| IL2RA | 0.01113 | 3.26967 | ITGA6 | 0.00577 | 0.06362 |
| ITGAX | 0.01191 | 2.07030 | IL15 | 0.00577 | 0.25342 |
| FCER1G | 0.01209 | 3.68320 | ITGB1 | 0.00585 | 0.48091 |
| DPP4 | 0.00851 | 2.63478 | CCL24 | 0.00587 | 0.09091 |
| CCL3 | 0.00851 | 3.86553 | CASP8 | 0.00697 | 0.48072 |
| IL13 | 0.00851 | 10.96200 | NLRP3 | 0.00697 | 0.12974 |
| TNFSF10 | 0.01342 | 3.23159 | IL6R | 0.00697 | 0.04533 |
| XCL1 | 0.01350 | 3.63855 | SELL | 0.00784 | 0.27297 |
| GAPDH | 0.01384 | 1.67977 | SYK | 0.00788 | 0.05734 |
| NCF4 | 0.01384 | 1.71959 | TRAF1 | 0.00828 | 0.54448 |
| CISH | 0.01384 | 6.75305 | IL21R | 0.00828 | 0.40174 |
| KLRF2 | 0.01454 | 4.84632 | CIITA | 0.00924 | 0.30701 |
| LAG3 | 0.01460 | 2.64611 | HLA-DPB1 | 0.01209 | 0.58034 |
| PTGS2 | 0.01471 | 5.34714 | TNFRSF14 | 0.01209 | 0.49924 |
| CCL18 | 0.01497 | 2.98956 | HLA-DMB | 0.01209 | 0.63451 |
| LIF | 0.01533 | 5.74462 | CD6 | 0.01209 | 0.44243 |
| PDGFRB | 0.01712 | 3.53609 | RARRES3 | 0.01209 | 0.54712 |
| CCND3 | 0.01743 | 1.83435 | CXCL11 | 0.01314 | 0.10345 |
| GZMA | 0.01821 | 2.11802 | CD44 | 0.01342 | 0.41938 |
| CCR8 | 0.01821 | 1.53114 | TLR1 | 0.01350 | 0.55877 |
| CCL2 | 0.01821 | 5.90181 | TLR9 | 0.01386 | 0.30631 |
| IFIH1 | 0.01821 | 2.20198 | TNFRSF17 | 0.01397 | 0.03631 |
| PLAUR | 0.01821 | 1.69454 | EBI3 | 0.01433 | 0.29787 |
| CCBP2 | 0.01821 | 5.56993 | CD82 | 0.01460 | 0.62381 |
| IFITM1 | 0.01905 | 2.49478 | STAT6 | 0.01460 | 0.57347 |
| TUBB | 0.01958 | 2.01669 | IL7R | 0.01471 | 0.15475 |
| CCR1 | 0.01958 | 7.75882 | EOMES | 0.01471 | 0.32396 |
| TNF | 0.01958 | 1.76365 | CFH | 0.01602 | 0.51495 |
| CDKN1A | 0.01958 | 2.93698 | TGFB1 | 0.01628 | 0.67611 |

FIG. 22

| Gene Name | P Value | Fold Change |
|---|---|---|
| SLAMF6 | 0.01628 | 0.51056 |
| TOLLIP | 0.01655 | 0.66615 |
| LY96 | 0.01655 | 0.64675 |
| HLA-DMA | 0.01712 | 0.64402 |
| ICOSLG | 0.01743 | 0.40284 |
| ATG7 | 0.01743 | 0.68213 |
| MBP | 0.01743 | 0.62974 |
| PTK2 | 0.01743 | 0.02695 |
| TNFAIP3 | 0.01743 | 0.44911 |
| TYK2 | 0.01743 | 0.70494 |
| FAS | 0.01743 | 0.62709 |
| PLAU | 0.01743 | 0.13369 |
| STAT5A | 0.01743 | 0.65752 |
| CTNNB1 | 0.01743 | 0.70534 |
| MS4A1 | 0.01743 | 0.04961 |
| SMAD5 | 0.01754 | 0.67904 |
| MAF | 0.01821 | 0.44447 |
| MAP4K4 | 0.01821 | 0.69104 |
| IL16 | 0.01821 | 0.56076 |
| IKBKB | 0.01821 | 0.67992 |
| NFATC2 | 0.01861 | 0.57920 |
| KIR3DL2 | 0.01867 | 0.40404 |
| CD81 | 0.01886 | 0.69911 |
| TLR3 | 0.01915 | 0.32951 |
| CXCL10 | 0.01958 | 0.14631 |
| ATG16L1 | 0.01958 | 0.63774 |
| ITGAE | 0.01958 | 0.71460 |
| TGFBR2 | 0.01958 | 0.53011 |

FIG. 22 (cont.)

SEQUENCE LISTING

<160> NUMBER OF SEQ ID NOS: 26

<210> SEQ ID NO 1
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 1

Pro Ile Leu Leu Thr Ile Ser Ile Leu Ser Phe Phe Ser Val Ala Leu
1               5                   10                  15

Leu Val Ile Leu Ala Cys Val Leu Trp
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 2

Pro Ile Leu Leu Thr Cys Pro Thr Ile Ser Ile Leu Ser Phe Phe Ser
1               5                   10                  15

Val Ala Leu Leu Val Ile Leu Ala Cys Val Leu Trp
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 3

Pro Ile Leu Asn Pro Cys Leu Thr Ile Ser Ile Leu Ser Phe Phe Ser
1               5                   10                  15

Val Ala Leu Leu Val Ile Leu Ala Cys Val Leu Trp
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 4

Pro Thr Cys Leu Thr Ile Ser Ile Leu Ser Phe Phe Ser Val Ala Leu
1               5                   10                  15

Leu Val Ile Leu Ala Cys Val Leu Trp
            20                  25

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 5

Pro Ser Ala Asn Cys Gly Ala Ile Ser Ile Leu Ser Phe Phe Ser Val
1               5                   10                  15

Ala Leu Leu Val Ile Leu Ala Cys Val Leu Trp
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 6

Pro Ile Leu Leu Val Ser Cys Pro Thr Ile Ser Ile Leu Ser Phe Phe
1               5                   10                  15

Ser Val Ala Leu Leu Val Ile Leu Ala Cys Val Leu Trp
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 7

Pro Ile Leu Leu Ile Ile Ser Ile Gln Trp Leu Ser Phe Phe Ser Val
1               5                   10                  15

Ala Leu Leu Val Ile Leu Ala Cys Val Leu Trp
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 8

Asn Ser Pro Ser Cys Leu Thr Ile Ser Ile Leu Ser Phe Phe Ser Val
1               5                   10                  15

Ala Leu Leu Val Ile Leu Ala Cys Val Leu Trp
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 9

Pro Cys Leu Glu Gly Leu Thr Ile Ser Ile Leu Ser Phe Phe Ser Val
1               5                   10                  15

Ala Leu Leu Val Ile Leu Ala Cys Val Leu Trp
            20                  25

<210> SEQ ID NO 10
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 10

Pro Ile Leu Leu Thr Ile Ser Ile Leu Ser Phe Phe Trp Asn Leu Leu
1               5                   10                  15

Val Ile Leu Ala Cys Val Leu Trp
            20

<210> SEQ ID NO 11
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 11

Arg Phe Cys Pro His Ile Ser Ile Leu Ser Phe Phe Ser Val Ala Leu
1               5                   10                  15

Leu Val Ile Leu Ala Cys Val Leu Trp
            20                  25

<210> SEQ ID NO 12
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 12

Ile Lys Cys Ile Leu Ser Phe Phe Ser Val Ala Leu Leu Val Ile Leu
1               5                   10                  15

Ala Cys Val Leu Trp
            20

<210> SEQ ID NO 13
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 13

Pro Ile Phe His Pro Phe Asn Cys Gly Pro Ile Ser Ile Leu Ser Phe
1               5                   10                  15

Phe Ser Val Ala Leu Leu Val Ile Leu Ala Cys Val Leu Trp
            20                  25                  30

<210> SEQ ID NO 14
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 14

Pro Ile Leu Leu Met Cys Pro Thr Ile Ser Ile Leu Ser Phe Phe Ser
1               5                   10                  15

Val Ala Leu Leu Val Ile Leu Ala Cys Val Leu Trp
            20                  25

<210> SEQ ID NO 15
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 15

Pro Ile Leu Leu Thr Ile Ser Ile Leu Ser Phe Phe Ser Gly Pro Ser

```
                1               5                  10                  15
Leu Ala Leu Leu Val Ile Leu Ala Cys Val Leu Trp
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 16

Pro Ile Leu Arg Leu Gly Cys Val Thr Ile Ser Ile Leu Ser Phe Phe
1               5                  10                  15

Ser Val Ala Leu Leu Val Ile Leu Ala Cys Val Leu Trp
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 17

Pro Ile Pro Gln Gly Gly Cys Ile Leu Ser Phe Phe Ser Val Ala Leu
1               5                  10                  15

Leu Val Ile Leu Ala Cys Val Leu Trp
            20                  25

<210> SEQ ID NO 18
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 18

Leu Gln Ser Cys Ile Leu Ser Phe Phe Ser Val Ala Leu Leu Val Ile
1               5                  10                  15

Leu Ala Cys Val Leu Trp
            20

<210> SEQ ID NO 19
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 19

Pro Ile Phe Pro His Gln His Cys Thr Ile Ser Ile Leu Ser Phe Phe
1               5                  10                  15

Ser Val Ala Leu Leu Val Ile Leu Ala Cys Val Leu Trp
            20                  25

<210> SEQ ID NO 20
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 20
```

```
Pro Ile Leu Leu Thr Ile Ser Lys Cys His Leu Ser Phe Phe Ser Val
1               5                   10                  15

Ala Leu Leu Val Ile Leu Ala Cys Val Leu Trp
            20                  25
```

<210> SEQ ID NO 21
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 21

```
Pro Ile Leu Leu Thr Cys His Leu Ile Ser Ile Leu Ser Phe Phe Ser
1               5                   10                  15

Val Ala Leu Leu Val Ile Leu Ala Cys Val Leu Trp
            20                  25
```

<210> SEQ ID NO 22
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 22

```
Pro Ile Phe Ser Cys Gly Pro Leu Thr Ile Ser Ile Leu Ser Phe Phe
1               5                   10                  15

Ser Val Ala Leu Leu Val Ile Leu Ala Cys Val Leu Trp
            20                  25
```

<210> SEQ ID NO 23
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 23

```
Pro Ile Leu Leu Pro Pro Cys Leu Thr Ile Ser Ile Leu Ser Phe Phe
1               5                   10                  15

Ser Val Ala Leu Leu Val Ile Leu Ala Cys Val Leu Trp
            20                  25
```

<210> SEQ ID NO 24
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 24

```
Pro Ile Leu Leu Thr Pro Pro Val Cys Ser Val Thr Ile Ser Ile Leu
1               5                   10                  15

Ser Phe Phe Ser Val Ala Leu Leu Val Ile Leu Ala Cys Val Leu Trp
            20                  25                  30
```

<210> SEQ ID NO 25
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 25

```
Leu Leu Thr Ile Ser Ile Leu Ser Phe Phe Ser Val Ala Leu Leu Val
1               5                   10                  15
Ile Leu Ala Cys Val Leu Trp
            20

<210> SEQ ID NO 26
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 26

Arg Ser Lys Arg Ser Arg Leu Leu
1               5
```

CONSTITUTIVELY ACTIVE CYTOKINE RECEPTORS FOR CELL THERAPY

This application is a national phase application under 35 U.S.C. § 371 that claims priority to International Application No. PCT/US2017/046588 filed Aug. 11, 2017, which claims priority to U.S. Provisional Patent Application Ser. No. 62/380,021, filed Aug. 26, 2016, all of which are incorporated herein by reference in their entirety.

STATEMENT REGARDING FEDERALLY SPONSORED RESEARCH OR DEVELOPMENT

This invention was made with government support under CA094237 and CA173750, awarded by the National Institutes of Health. The government has certain rights in the invention.

TECHNICAL FIELD

Embodiments of the disclosure include at least the fields of cell biology, molecular biology, immunology, and medicine, including at least cancer medicine.

BACKGROUND

Cell therapy with antigen-specific T-cells has shown promise in preclinical models and early phase clinical trials, however few patients with bulky disease have been cured. This lack of efficacy is because of several factors, including limited in vivo T-cell expansion post-infusion. Lymphodepleting patients prior to T-cell transfer with chemotherapy and/or radiation greatly enhances in vivo T-cell expansion, however these agents have unwanted side effects. There is needed a means for enabling T-cell expansion without such toxic agents.

The present disclosure satisfies a need in the art to provide methods and compositions for safely enhancing T-cell expansion in vivo.

BRIEF SUMMARY

Embodiments of the disclosure concern methods and compositions for enhancing immune cell expansion and/or proliferation, including in vivo following infusion. In specific cases, T-cells express a particular constitutively active cytokine receptor molecule to facilitate expansion of the T-cells in vivo for use as a therapy for a medical condition, including cancer. The constitutively active cytokine receptor comprises at least one endodomain, a transmembrane domain, and at least one exodomain, in specific embodiments.

In a first aspect, provided herein are engineered cytokine receptor polypeptides that homodimerize and facilitate downstream signaling without need for binding of the relevant cytokine. A common feature of such engineered cytokine receptors is that they are engineered to comprise one or more mutations, e.g., in the transmembrane domain, that cause or facilitate homodimerization, and therefore signaling, in the absence of binding of the cognate cytokine. As such, with respect to cytokine signaling, they are constitutively active (that is, the mutations are "gain-of-function" mutations).

In particular cases, the engineered cytokine receptor polypeptide is constitutively active because the transmembrane domain of the receptor comprises one or more mutations that permit the receptor to homodimerize such that an external signal, e.g., a cytokine, is not required to activate the transmembrane domain and endodomains. In at least some cases, the one or more mutations in the transmembrane domain impart a structural configuration to the transmembrane domain/endodomain that positions the molecule in closer proximity to a desired target molecule through which their signal acts. In specific examples, the mutation in the transmembrane domain is or comprises insertion of at least one cysteine in the transmembrane domain amino acid sequence to allow a disulfide bridge to form (thereby facilitating homodimerization of the polypeptide) and/or includes insertion of at least one proline to induce a conformational change (for example, to cause the molecule to kink or twist or rotate about an axis through the receptor molecule), both of which mutations would structurally impact the nature of the molecule and therefore its signaling.

In specific embodiments, the transmembrane domain is a IL-7 cytokine receptor alpha transmembrane domain comprising one or more mutations compared to the corresponding wildtype IL-7 cytokine receptor alpha transmembrane domain. In a specific embodiment, when the transmembrane domain is from IL-7 cytokine receptor alpha, the mutation is in the sequence LLTISILSFFSVALLVILACVLW (SEQ ID NO:25). In specific aspects, the mutation introduces at least one cysteine into the transmembrane domain and/or the mutation introduces a proline into the transmembrane domain. The transmembrane domain is 21, 22, 23, 24, 25, 26, 27, 28, 29, 30, 31, 32, or 33 amino acids in length, in some cases.

In particular embodiments of the transmembrane domain, the domain is self-dimerizing, and in specific cases the transmembrane domain is the endogenous transmembrane domain of the one or more cytokine receptor endodomains of the disclosure or that is a self-activating derivative thereof. A self-activating derivative may comprise one or more mutations compared to the corresponding wildtype transmembrane domain, and the one or more mutations renders the receptor able to homodimerize. In specific cases the mutation(s) render the receptor able to homodimerize through the transmembrane and endodomain components. In specific embodiments, the one or more mutations renders the transmembrane and endodomain able to structurally orient (such as twist) such that janus kinases are able to phosphorylate and activate the endodomains/polypeptides, for example. In specific embodiments, the one or more mutations renders the transmembrane and endodomain able to structurally twist collectively in a helical manner.

In certain embodiments, the engineered cytokine receptor polypeptide comprises at least one endodomain, at least one transmembrane domain and at least one exodomain, and optionally comprises one or more exodomains. In some embodiments, the endodomain is wild-type, that is, is functionally active with respect to cytokine signaling. In a specific embodiment, the engineered cytokine receptor polypeptide comprises a normal (wild-type) exodomain; in this embodiment, the polypeptide homodimerizes, and transmits a signal, in the presence or absence of the cognate cytokine. In another specific embodiment, the engineered cytokine receptor polypeptide comprises an exodomain that is not a wild-type exodomain for such a receptor. In more specific embodiments, the exodomain binds a ligand that would normally be deleterious to the cell in which the receptor resides (for example, a ligand that normally would down-regulate the cell or cause anergy of the cell or cause apoptosis of the cell). For example, such a non-wild-type exodomain can be, or can serve as, a decoy receptor for, e.g., a checkpoint protein; e.g., the exodomain comprises a receptor for the checkpoint protein PD-1. In some cases, the non-wild-type exodomain is a target for an antibody that, when bound to the exodomain, targets a cell comprising the engineered cytokine receptor polypeptide for destruction. In another specific embodiment, the engineered cytokine receptor polypeptide lacks an exodomain. In certain embodiments, the cytokine is an interleukin, such as IL-7, IL-21, IL-23, or IL-12.

In specific aspects of the disclosure, a constitutively active cytokine receptor induces constitutive IL-7 receptor activity. In certain embodiments, one or more mutations or alterations in the transmembrane domain of IL-7Rα renders the receptor able to induce signaling in a homo-dimerization state. In a specific embodiment, the interleukin is IL-7. In a specific embodiment, the engineered cytokine receptor polypeptide is an engineered IL-7 receptor polypeptide.

In other embodiments, provided herein are polynucleotides that encode such engineered cytokine receptor polypeptides, cells that comprise such polynucleotides, cells that express such polypeptides, e.g., cells that additionally express a chimeric antigen receptor, and the uses of such cells to treat disease, e.g., cancer (e.g., a blood cancer or a solid tumor).

In one embodiment, there is a polynucleotide that encodes an engineered cytokine receptor polypeptide, and the polypeptide comprises the following operably linked components: a) one or more cytokine receptor endodomains; b) a transmembrane domain that comprises one or more mutations that promote homodimerization of the engineered receptor; and c) optionally, or not, one or more extracellular domains that are not an endogenous extracellular domain for the corresponding one or more cytokine receptor endodomains in component a), wherein the extracellular domain is not derived from a cytokine receptor. In certain embodiments there are one or more cells that comprise such a polynucleotide.

In certain embodiments, one or more cytokine receptor endodomains elicits signaling through a STAT5 pathway in the cell or a STAT3 pathway in the cell. In specific cases, a cytokine receptor endodomain is from IL-7 receptor alpha, IL-21 receptor alpha, CD122, IL-23 receptor alpha, IL-12 receptor alpha, or a combination thereof.

In one embodiment, an extracellular domain is globular in form. The extracellular domain may be a decoy receptor that lacks signal transmission activity. The extracellular domain may be the target of a cytotoxic antibody. In specific cases, the extracellular domain is at least 70 amino acids and/or no more than 2000 amino acids. The length of the extracellular domain may be between 70-2000 amino acids, 100-1000 amino acids, 500-2000 amino acids, 50-500 amino acids, 100-750 amino acids, 200-2000 amino acids, or 500-2000 amino acids. In some cases, the extracellular domain is the extracellular domain of CD34. In certain embodiments, the extracellular domain is from CD30, HER2, EGFR, CD19, CD34, TGF-beta receptor, IL-4 receptor, IL-13 receptor alpha1 and alpha 2, IL-8 receptor, IL-10 receptor, PD-1, LAG3, TIGIT, CTLA4, FAS, CD19, CD27, CD28, CD52, CD134, CD137, HER2, EGFR, NGFR, or a combination thereof.

In particular embodiments, a cell(s) expressing a constitutively active cytokine receptor is an immune cell. The cell may be a T-cell, a NK cell, a NK T-cell, αβcell, γδT-cell, a Mucosa Associated Invariant T-cell (MAIT T-cell), innate lymphoid cell, a stem cell, or a progenitor cell. In specific embodiments, the cell comprises a non-natural molecule that confers antigen specificity for the cell. The cell may further comprise at least one additional engineered receptor, for example another constitutively active cytokine receptor, a chimeric antigen receptor, a recombinant T-cell receptor, a bispecific T-cell engager (BiTE or T-cell ENG), Dual-Affinity Re-Targeting (DART) protein, or a combination thereof.

In some embodiments related to cells expressing the constitutively active cytokine receptor, the cell harbors a polynucleotide that expresses a receptor polypeptide. The polynucleotide may be further defined as an expression vector, such as a viral vector or a non-viral vector. A viral vector may be a retroviral, lentiviral, adenoviral, or adeno-associated viral vector. A non-viral vector may be a plasmid, for example.

In an embodiment, there is a plurality of cells of the disclosure that express a constitutively active cytokine receptor, wherein the cells comprise a mixture of one or more of a T-cell, a NK cell, a NK T-cell, an αβ T-cell, a γδT-cell, a Mucosa Associated Invariant T-cell (MAIT T-cell), innate lymphoid cell, a stem cell, a progenitor cell, or an immune effector cell.

In one embodiment, there is a method of expanding a population of cells, comprising the step of expressing the polynucleotide in a cell encompassed by the disclosure. The cell may be in vitro or in vivo, such as in a mammal, including a human. In specific embodiments, the human is provided an effective amount of one or more inhibitors of the extracellular domain that upon binding to the extracellular domain target the cell for destruction. The inhibitor may be one or more antibodies of any kind. In certain embodiments, the human is in need of therapy and a therapeutically effective amount of cells is provided to the human. In specific aspects, the human has cancer, an infectious disease, an autoimmune disease, an immunodeficiency, or is pre- or post-solid organ transplantation or stem cell transplantation.

In certain embodiments, the constitutively active cytokine receptor utilizes an exodomain that is utilized as a sink or ligand trap, such as by binding up one or more molecules that would be detrimental to the cells expressing the constitutively active cytokine receptor. Such a ligand may be immunosuppressive, for example, because it would normally activate signaling pathways to turn off the T-cell, as in immunosuppression. In some such cases the exodomain binds the harmful ligand as a decoy receptor yet the transmembrane/endodomains are still able to independently give a positive cytokine signal. In some embodiments, a decoy receptor prevents a corresponding ligand from suppressing the T-cell as it would under normal circumstances. Exodomains of the decoy receptor may bind inhibitory cytokines, for example. Examples of harmful ligands to which the decoy receptor may bind include TGF-beta, PD-L1, IL-4, IL-13, IL-8, and IL-10. In some embodiments, the decoy receptor exodomain is one of an inhibitory receptor normally expressed by T-cells such as, but not limited to, LAG3, TIGIT, CTLA4, FAS.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 4A is data from a representative donor, and FIG. 4B is the average results of three donors.

FIGS. 14A-14I: Constitutive signaling from C7R activates STAT5 in T-cells but does not support autonomous cell expansion. (14A) Schematic comparisons of IL-7 bound to the natural IL-7 receptor composed of heterodimerized IL7Rα and γc, compared to the engineered C7R homodimerized receptor. (14B, 14C) Transduction efficiency of A34 and C7R (representative of 3) in (14B) CD4 and (c) CD8 T-cells relative to non-transduced (NT) cells. (14D, 14E) Representative flow cytometric comparison of phosphorylated STAT5 (pSTAT5) in (14D) CD4 and (14E) CD8 Tcells that were transduced with A34 or C7R. Cells were cultured without IL-15 and IL-7 for 24-72 hours before analysis. (14F, 14G) Average pSTAT5 MFI values when repeating the experiments in 14D and 14E with multiple donors. (14H, 14I) Quantitated in-vitro persistence of A34 or C7R transduced (14H) CD4 or (14I) CD8 T-cells cultured in cytokine-free complete cell culture media starting 9-12 days after PBMC activation, without further antigen stimulus. Live cells were counted weekly using trypan-blue exclusion. X-axis denotes the number of days after IL-15 and IL-7 were withdrawn from culture media. Area under the curve (AUC) values were compared with the two-tailed t-test: 10.5±0.6616 (CD8 Δ34), 56.37±7.972 (CD8 C7R), p<0.05; 10.22±1.694 (CD4 Δ34) and 31.36±2.590 (CD4 C7R), p<0.05. *P<0.05, P<0.01, *P<0.001 (two-tailed paired t-test, 14F-14I). Graphs 14F-14I represent averages from different donors ±SEM (n=3).

FIGS. 17A-17D: C7R-CAR T-cells can be deleted using the iC9 suicide switch. (17A) T-cells doubly transduced with GD2-CAR.C7R and iC9-CD19t vectors were selected for iC9 expression using CD19-specific Miltenyi Biotec® beads. Cells were then incubated with AP20187 in complete culture media for 24 hours and then stained with Annexin V and 7-AAD. Bar graphs show relative frequencies of T-cells staining positive for Annexin V, 7-AAD, both, or neither. Annexin V(+)7-AAD(−) and Annexin V(−)7-AAD(+) comparisons were n.s. (17B, 17C) LAN-1 tumors were established subcutaneously in NSG mice for 8 days before 1×10⁶ T-cells transduced with GFP-FFluc and with GD2-CARΔ.C7R, GD2-CAR.C7R, or GD2-CAR.C7R+iC9-CD19t were infused intravenously. GD2-CARΔ.C7R was used as the same control in 17B and 17C. Tumor volumes were measured over time. 2 mice in the GD2-CARΔ.C7R group were euthanized after Day 21 due to tumor burden, and on Day 24 the tumor sizes of the remaining 3 mice were compared with those in the GD2-CAR.C7R and GD2-CAR.C7R+iC9-CD19t groups. Mean tumor volume at 32 days after T-cell infusion: 236±11 mm3 for GD2-CAR.C7R, 196±18 mm3 for GD2-CAR.C7R+iC9-ΔCD19t, n.s. (p=0.1857). (17D) Bioluminescent signal of GD2-CAR.C7R T-cells (with and without iC9-CD19t) from the tumor site was quantitated over time. Red arrows indicate initiation of AP20187 dosing on Day 28 every 24 hours for a total of 3 doses. *P<0.05, **P<0.01 (two-tailed t-test, 17A, 17D; Welch's t-test, 17B, 17C). n=5 mice per group. The graph in 17A represents averages from different donors ±SEM (n=3).

FIGS. 19A-19B: Efficient retroviral transduction of C7R and Δ34 in both CD4 and CD8 selected T-cells. CD34 expression was assessed by flow cytometry to detect C7R and Δ34 transduction in (19A) CD4 and (19B) CD8 T-cells, relative to NT T-cell controls. Differences were n.s. when compared with a two-tailed t-test (n=3).

FIGS. 21A-21B: C7R does not significantly increase intracranial EphA2-CAR T-cell expansion against U373 tumors. (21A, 21B) To track T-cells, 1×10⁵ U373 cells were injected intracranially into SCID mice, followed 7 days later by 1×10⁴ T-cells expressing EphA2-CAR or EphA2-CAR.C7R, co3 expressing GFP-FFluc. (21A) Bioluminescent images were collected over time and quantitated. (21B) AUC analysis was performed and found to be n.s. between both groups (two-tailed t-test). n=5 mice per group.

FIG. 22: Differential gene expression in GD2-CAR.C7R T-cells compared to GD2-CAR T-cells. After the end of CC2, tumors were labeled with GD2-specific antibody and magnetically separated from the CAR T-cells. Total RNA was isolated from T-cells and gene expression analysis was subsequently performed using the Human Immunology Panel Version 2 and nCounter® Analysis System (NanoString@). The displayed tables shows fold changes in genes (GD2-CAR.C7R/GD2-CAR) that had P values less than 0.02. Data was generated from 5 donors (10 paired samples).

In FIG. 23A, there is imaging of luciferase in mice treated with 34.IL7RP2-EBVSTs. FIG. 23B shows measurement of tumor growth in 34.IL7RP2-EBVSTs treated mice.

Figure 1:
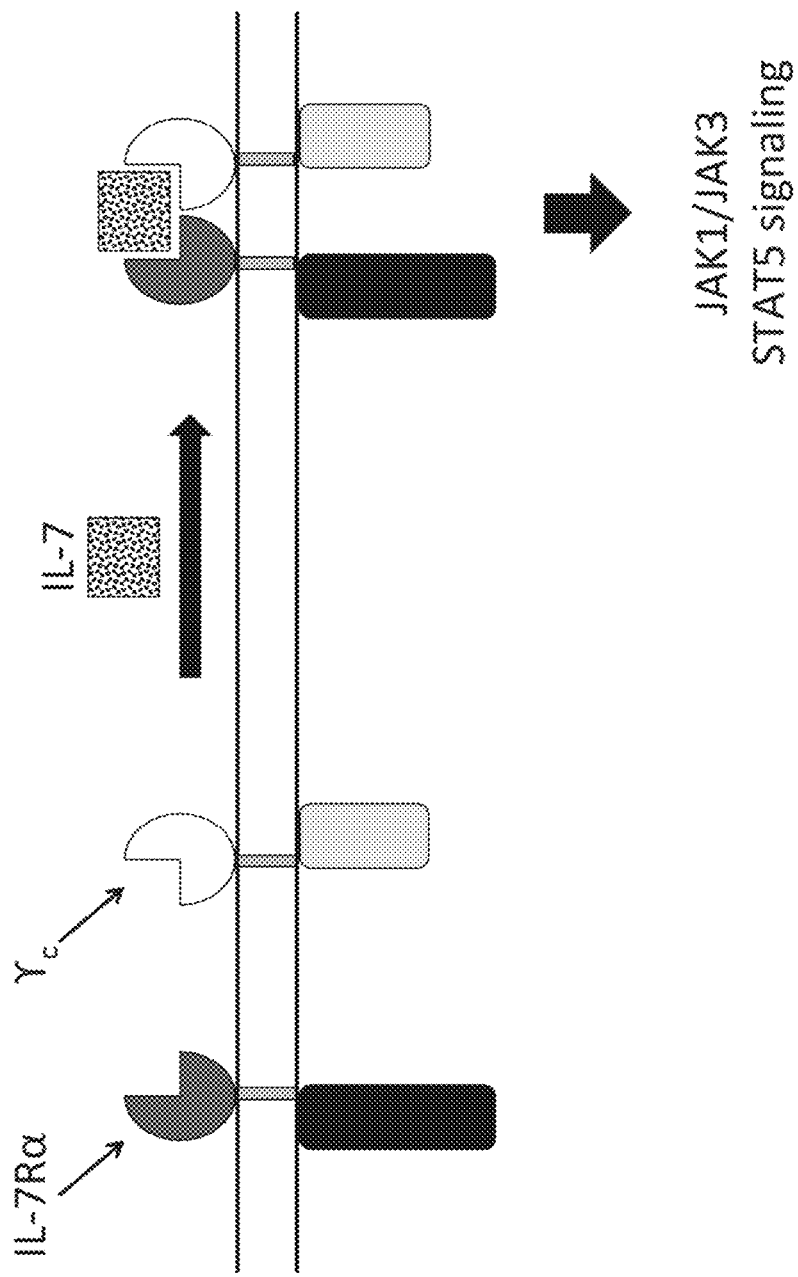
FIG. 1: Scheme of normal IL-7 cytokine/receptor signaling.

The scope of the present application is not intended to be limited to the particular embodiments of the process, machine, manufacture, composition of matter, means, methods and steps described in the specification.

DETAILED DESCRIPTION

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

The term "cytokine" as used herein refers to cell signaling molecules that regulate the immune system's response to inflammation and infection and aid cell to cell communication in immune responses. Examples include chemokines, interferons, interleukins, lymphokines, and tumour necrosis factors.

I. General Embodiments

The present disclosure concerns improvements to cellular immunotherapy agents to enhance their expansion, including in vivo following delivery to an individual in need thereof. Such improvements utilize a constitutively active cytokine receptor comprised of multiple components, including at least one endodomain of a cytokine receptor, a transmembrane domain, and at least one exodomain, although in some cases the exodomain is lacking in the receptor. In one embodiment, the constitutively active cytokine receptor utilizes the endodomain of the IL-7 cytokine receptor alpha chain. Antigen-specific T-cells, genetically modified to express a non-natural chimeric IL7R-comprising receptor, showed robust expansion in cell culture studies as well as in an animal model, in contrast to unmodified T-cells.

II. Constitutively Active Cytokine Receptor Molecules

In particular embodiments, constitutively active cytokine receptors (in protein and/or nucleic acid form), methods of making them, and methods of using them are encompassed by the disclosure. The receptors comprise at least one exodomain, a transmembrane domain, and at least one endodomain, wherein the endodomain is derived from a cytokine receptor and wherein the exodomain is derived from the same or a different molecule than the transmembrane and endodomain components. In alternative embodiments, the transmembrane domain and the exodomain are from the same molecule and the endodomain is from a different molecule, but the receptor is still constitutively active because the molecule includes a mutation that twists the transmembrane domain and/or endodomain.

In specific cases, the constitutively active cytokine receptors are constitutively active because their transmembrane domain and/or endodomain components are configured to transmit an activating signal in the absence of receipt of a corresponding signal from the exodomain to which they are operably linked. That is, in particular embodiments of the receptors, there is no ligand requirement for the cytokine receptor. In some cases, the transmembrane domain and/or endodomain of the constitutively active cytokine receptors of the disclosure may be configured such that they are able to homodimerize in a non-natural manner or situation or environment, thereby allowing the exodomain to remain in a state that transmits an activating signal to a corresponding entity downstream in a signaling pathway. In particular embodiments, the transmembrane/endodomains of the constitutively active cytokine receptors independently give a positive cytokine signal in the absence of binding of a cytokine by the exodomain to which they are operably linked.

In certain embodiments, particular constitutively active cytokine receptors are utilized in methods of the disclosure.

The dCD34.IL7RP2 cDNA sequence is provided in SEQ ID NO:2 and corresponding protein sequence is in SEQ ID NO:3. The construct dCD34.IL7RP2 comprises the entire CD34 exodomain; the IL7R TM domain with a cysteine, proline, threonine (CPT) insertion; and a normal IL7R endodomain.

The IL7RP2 cDNA sequence is provided in SEQ ID NO:4, and the corresponding protein sequence is in SEQ ID NO:5. The construct IL7RP2 comprises the IL7R exodomain; the IL7R transmembrane domain with a CPT insertion; and a normal IL7R endodomain.

The Q8E.IL7RP2 cDNA sequence is provided in SEQ ID NO:6, and the corresponding protein sequence is in SEQ ID NO:7. The construct Q8E.IL7RP2 has a fragment of the CD34 extracellular domain plus a CD8 stalk; the IL7R transmembrane domain with a CPT insertion; and a normal IL7R endodomain.

The 19AA.IL7RP2 cDNA sequence is provided in SEQ ID NO:8, while the corresponding protein sequence is in SEQ ID NO:9. The 19AA.IL7RP2 construct comprises 19 aa of the IL7R exodomain (derived from the last 19 amino acids in the IL7R ectodomain before the IL7R transmembrane domain starts); the IL7R transmembrane domain with a CPT insertion; and a normal IL7R endodomain.

A. Exodomain

In specific embodiments, the constitutively active cytokine receptor comprises one, two, or more exodomains. In particular embodiments, the exodomain is capable of binding a ligand but the signal itself is not transmitted, for example because of structural or other reasons. The exodomain may or may not be from the same natural molecule as its corresponding transmembrane and/or endodomain, in particular embodiments. The exodomain may or may not be from the same natural molecule as the endodomain to which it is operably linked.

In some cases, the exodomain is globular in form, akin to the three-dimensional geometry of the IL7-receptor exodomain and the CD34 exodomain. One characteristic provided by the exodomain may be to provide protein stabilization, as at least some data indicates that at least certain exodomains allow high protein expression and concomitant high signal activation (such as pSTAT5 activation).

In some cases, the exodomain comprises high glycosylation that stabilizes the protein and may increase signaling.

In some embodiments, the exodomain permits identification of the transduced cells. For example, in cases wherein the exodomain is not normally expressed on T-cells, the exodomain allows the transduced cells to be identified, such as by gating out during flow cytometry analysis and also, for example, magnetically selected for enrichment (such as using magnetic beads conjugated to a corresponding antibody).

In some embodiments the constitutively active cytokine receptor utilizes an exodomain that imparts a sink or ligand trap function, such as binding up of one or more molecules that would be harmful to the cells expressing the constitutively active cytokine receptor. In certain embodiments the ligand is immunosuppressive, for example, because it would normally activate signaling pathways to turn off the T-cell (immunosuppression). In some such cases the exodomain binds the harmful ligand as a decoy receptor yet the transmembrane/endodomains are still able to independently give a positive cytokine signal. In certain embodiments, a decoy receptor prevents a corresponding ligand from suppressing the T-cell as it would under normal circumstances. In specific cases, the decoy receptor exodomain is able to bind inhibitory cytokines, for example. Examples of harmful ligands include TGF-beta, PD-L1, IL-4, IL-13, IL-8, and IL-10. In addition the decoy receptor exodomain can encode the exodomain of an inhibitory receptor normally expressed by T-cells such as, but not limited to, LAG3, TIGIT, CTLA4, FAS. In certain embodiments, the receptor is constitutively signaling and signaling is further augmented in the presence of a designated trigger. In alternative embodiments, the exodomain is not from a cytokine receptor, including not from IL-4 cytokine receptor or IL-13 cytokine receptor, for example. In some cases, the exodomain may or may not comprise an antibody, such as a scFv.

In particular aspects, the exodomain is a target for destruction of the cell. For example, the exodomain may be utilized as a target for a molecule that directly or indirectly results in apoptosis of the cell that expresses the receptor. For example, the exodomain may be targeted with a corresponding antibody that binds the exodomain, resulting in the ultimate destruction of the cell.

In some cases the constitutively acting receptor has an exodomain that acts as a decoy receptor for an inhibitory ligand and also has a domain for suicide targeting, although in some cases the decoy receptor exodomain and suicide targeting exodomain are one and the same.

In specific embodiments, the exodomain comprises the extracellular domain of CD30, HER2, EGFR, CD19, CD34, CD34, TGF-beta receptor, IL-4 receptor, IL-13 receptor alpha1 and alpha 2, IL-8 receptor, IL-10 receptor, PD-1, LAG3, TIGIT, CTLA4, FAS, CD19, CD27, CD28, CD52, CD134, CD137, HER2, EGFR, or NGFR. In addition, the exodomain can comprise monoclonal antibodies or their derivatives (for example but not limited to scFVs), or dimerizer domains (for example but not limited to FKBP).

In certain cases the exodomain comprises the podocalyxin (also known as podocalyxin-like protein 1; PODXL (also known as PCLP1); thrombomucin; gp135; GCTM2; TRA-1-60; TRA-1-81; or endoglycan (also known as podocalyxin-like protein 2, PODXL2 or PCLP2).

In some embodiments the exodomain component of the receptor is from a naturally occurring molecule and is wildtype, although in other cases the exodomain comprises one or more mutations compared to a corresponding wildtype naturally-occurring molecule. The one or more mutations may function to further stabilize the receptor, for example. In cases wherein the exodomain comprises one or more mutations compared to a corresponding wildtype sequence, the mutated version may have a certain percent identity over part or all of the sequences, such as at least 50, 55, 60, 65, 70, 75, 80, 85, 90, 91, 92, 93, 94, 95, 96, 97, 98, or 99% identity compared to the corresponding wild type protein or nucleic acid sequence.

In some embodiments, the extracellular domain is of a certain length. In specific embodiments, the length of the extracellular domain is between 10-275 amino acids, 10-225 amino acids, 10-200 amino acids, 10-175 amino acids, 10-150 amino acids, 10-125 amino acids, 10-100 amino acids, 10-50 amino acids, 50-250 amino acids, 50-225 amino acids, 50-200 amino acids, 50-175 amino acids, 50-150 amino acids, 50-100 amino acids, 90-250 amino acids, 90-225 amino acids, 90-200 amino acids, 90-175 amino acids, 90-150 amino acids, 90-125 amino acids, 90-100 amino acids, 100-250 amino acids, 100-225 amino acids, 100-200 amino acids, 100-175 amino acids, 100-150 amino acids, 100-125 amino acids, 125-250 amino acids, 125-225 amino acids, 125-200 amino acids, 125-175 amino acids, 125-150 amino acids, 150-250 amino acids, 150-225 amino acids, 150-200 amino acids, 150-175 amino acids, 175-250 amino acids, 175-225 amino acids, 175-200 amino acids, 200-250 amino acids, 200-225 amino acids, and so on.

In alternative embodiments, the receptor lacks an exodomain.

B. Transmembrane Domain

In specific embodiments, the constitutively active cytokine receptor comprises a transmembrane domain that is operably linked to the exodomain(s) and the endodomain(s). The transmembrane domain may or may not be from the same natural molecule as the endodomain to which it is operably linked. In particular embodiments the transmembrane is not from the same natural molecule as the exodomain to which it is operably linked. The transmembrane domain is not natural, in particular embodiments, because it requires a mutation that causes twisting of the molecule. The transmembrane domain comprises one or more mutations compared to its corresponding wildtype molecule that allows the transmembrane to be self-active, in at least certain embodiments. As used herein, the term "self-active" refers to a transmembrane that in conjunction with the endodomain to which it is operably linked transmits a signal to the cell in the absence of a corresponding activating signal from an exodomain to which it is operably linked. In certain embodiments, the transmembrane domain comprises one or more mutations that cause or facilitate homodimerization.

In particular cases the transmembrane domain imparts a functional configuration on the receptor to permit self-activation, such as allowing the downstream endodomains to be oriented relative to each other in a manner that is conducive to signaling, such as permitting janus kinases that have associated with the endodomains to interact with each other and cross activate each other. In particular aspects the transmembrane domain comprises one or more mutations that allow the transmembrane domain and endodomain to act in conjunction in a non-transient manner when they do not naturally do so. In at least some aspects the mutation renders the transmembrane and ectodomain able to homodimerize artificially. For example, the transmembrane domain may comprise one or more mutations that allow homodimerization of two separate molecules each of which comprises the transmembrane domain and at least one endodomain, wherein the homodimerization of such molecules does not occur in nature. In specific embodiments, the one or more mutations in the transmembrane domain induce structural twisting of the transmembrane and endodomains of a receptor homodimer to form a self-activating helical structure, for example. In specific embodiments, the one or more mutations in the transmembrane domain induce twisting helically of part or all of the receptor molecule (or one or more components thereof) about a vertical axis. The ability to determine whether or not a particular mutation will induce a structural configuration such that the transmembrane and endodomains self-activate may be determined with routine methods, such as assaying for STAT3 or STAT5 phosphorylation following growth of the cells harboring the particular receptor being tested in the absence of growth factors.

In particular embodiments, transmembrane domain components with such one or more gain-of-function mutations may be employed in methods and compositions of the disclosure. The mutation(s) may be a substitution, insertion, deletion, or combination thereof, for example. In specific embodiments, the one or more mutations comprises inclusion of at least one cysteine and/or at least one proline. In some cases, the transmembrane domain utilizes a mutation identified in a tumor patient as a gain-of-function mutation in the transmembrane domain. In at least some cases, the mutant versions include cysteine insertion(s) that induce disulfide bond formation in the transmembrane domain. In other embodiments, however, the one or more mutations lacks insertion of a cysteine. For example, transmembrane derivatives may be utilized that do not have a cysteine insertion(s) (and, therefore, no disulfide bond) that still signals and is constitutively active, for example because the mutation rendered the transmembrane domain conformationally changed compared to a natural version of the transmembrane domain, thereby allowing induction of signaling. For example, insertion of an amino acid such as a proline produces a "kink" that twists the transmembrane domain, which induces signaling (see, e.g., Shochat et al., 2011, *J Exp Med.* 2011 May 9; 208(5):901-8; Zenatti et al., 2011, *Nat Genet.* 2011 Sep. 4; 43(10):932-9).

In specific embodiments, the transmembrane domain is from the IL-7Rα receptor and the mutation in the transmembrane domain is in the sequence PILLTISILSFF-SVALLVILACVLW (SEQ ID NO:1). In certain embodiments, the mutation is, or comprises, the insertion of one or more cysteines, and/or one or more prolines, into the amino acid sequence of SEQ ID NO:1, wherein the mutation enables or facilitates homodimerization of the receptor. In certain cases, the mutation comprises an insertion of a trimer peptide of cysteine, proline, threonine (CPT) into the transmembrane domain. Such a mutation confers the disulfide bond formation between the —SH (thiol) groups of cysteine residues of two molecules (as an example, two IL7RP2 receptor alpha chains), allowing a homodimer to form between them (the proline immediately following the cysteine helps to twist the homodimer into the correct orientation, in specific embodiments). In specific embodiments, the threonine of the CPT insertion is not threonine but another amino acid, and in at least specific cases that other amino acid is or is not cysteine or proline.

In embodiments wherein one or more amino acids are inserted into SEQ ID NO:1 for use in the receptor, the insertion may be between any two amino acids of SEQ ID NO:1. In specific embodiments, the insertion is located after the 1$^{st}$, 2$^{nd}$ third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth amino acid in SEQ ID NO:1.

An example of a mutated TM sequence used in an exemplar construct described herein (Δ34.IL7RP2), wherein the sequence is mutated by addition of the underlined sequences is as follows:

```
                                    (SEQ ID NO: 2)
        PILLTCPTISILSFFSVALLVILACVLW
```

Mutated TM sequence in other constitutively active IL-7 receptors

```
    1.
                                    (SEQ ID NO: 3)
        PILNPCLTISILSFFSVALLVILACVLW 2.
                                    (SEQ ID NO: 4)
        PTCLTISILSFFSVALLVILACVLW 3.
                                    (SEQ ID NO: 5)
        PSANCGAISILSFFSVALLVILACVLW 4.
                                    (SEQ ID NO: 6)
        PILLVSCPTISILSFFSVALLVILACVLW 5.
                                    (SEQ ID NO: 7)
        PILLIISIQWLSFFSVALLVILACVLW 6.
                                    (SEQ ID NO: 8)
        NSPSCLTISILSFFSVALLVILACVLW 7.
                                    (SEQ ID NO: 9)
        PCLEGLTISILSFFSVALLVILACVLW 8.
                                    (SEQ ID NO: 10)
        PILLTISILSFFWNLLVILACVLW 9.
                                    (SEQ ID NO: 11)
        RFCPHISILSFFSVALLVILACVLW 10.
                                    (SEQ ID NO: 12)
        IKCILSFFSVALLVILACVLW 11.
                                    (SEQ ID NO: 13)
        PIFHPFNCGPISILSFFSVALLVILACVLW 12.
                                    (SEQ ID NO: 14)
        PILLMCPTISILSFFSVALLVILACVLW 13.
                                    (SEQ ID NO: 15)
        PILLTISILSFFSGPSLALLVILACVLW 14.
                                    (SEQ ID NO: 16)
        PILRLGCVTISILSFFSVALLVILACVLW 15.
                                    (SEQ ID NO: 17)
        PIPQGGCILSFFSVALLVILACVLW 16.
                                    (SEQ ID NO: 18)
        LQSCILSFFSVALLVILACVLW 17.
                                    (SEQ ID NO: 19)
        PIFPHQHCTISILSFFSVALLVILACVLW 18.
                                    (SEQ ID NO: 20)
        PILLTISKCHLSFFSVALLVILACVLW 19.
                                    (SEQ ID NO: 21)
        PILLTCHLISILSFFSVALLVILACVLW 20.
                                    (SEQ ID NO: 22)
        PIFSCGPLTISILSFFSVALLVILACVLW 21.
                                    (SEQ ID NO: 23)
        PILLPPCLTISILSFFSVALLVILACVLW 22.
                                    (SEQ ID NO: 24)
        PILLTPPVCSVTISILSFFSVALLVILACVLW
```

In specific embodiments, the one or more transmembrane domain mutations structurally alter the dimerized alpha chains (for the exemplary IL-7Rα) to orient themselves such that bound Janus Kinases are now in proximity, allowing cross-phosphorylation and activation; such a structural alteration derives from twisting of the dimerized chains, in specific embodiments. (Shochat et al., 2011; Durum, 2014).

In particular embodiments, the transmembrane domain comprises one or more mutations compared to its corresponding wildtype component, and in doing so has certain percent identity compared to wild type. In specific cases the transmembrane domain is at least 50, 60, 65, 70, 75, 80, 85, 90, 91, 92, 93, 94, 95, 96, 97, 98, or 99% identical to the corresponding wild-type transmembrane domain The transmembrane may be of any suitable length, but in specific embodiments it is 21, 22, 23, 24, 25, 26, 27, 28, 29, 30, 31, 32, or 33 amino acids in length.

C. Endodomain

The constitutively active cytokine receptor comprises one or more endodomains. In some cases the endodomain is from the same molecule as the transmembrane domain, although in other cases it is not. In particular embodiments the endodomain is from a cytokine receptor, including an immunostimulatory cytokine receptor. In specific embodiments, the cytokine receptor acts in a signaling pathway that includes STAT5, STAT3, and so forth. Immunostimulatory cytokine endodomains useful for receptors of the disclosure include IL-7Rα receptor alpha, CD122 (the common receptor beta of IL-2 and IL-15), IL-21 receptor alpha, IL-23 receptor alpha, and IL-12 receptor alpha, and IL-6 receptor, for example.

In some embodiments the endodomain is selected based on the desired downstream pathway. For example, the endodomain may be selected based on the desire for the signal to be transmitted via JAK1, STAT5, STAT4, JAK3, STAT3, and so on.

In certain cases the signaling pathway includes STAT5. STAT5 is a major downstream signaling node of immunostimulatory cytokines IL-15 and IL-7, both of which are known to be useful in activating T-cells in the context of immunotherapy. Several publications have already shown that bypassing the cytokine and the cytokine receptor interactions, and activating STAT5 directly (using constitutively active STAT5 mutants), CD8 T-cell function is enhanced via increased persistence in vivo and enhanced anti-tumor efficacy in vivo using preclinical models. The same concept can be extended to activating STAT proteins downstream of other known immunostimulatory cytokines, such as STAT4, which is downstream of IL-12.

In particular embodiments the endodomain comprises the endodomain from the IL7 receptor alpha chain, which may or may not comprise one or more mutations. In certain cases it is operably linked to a transmembrane domain that comprises a mutation that allows that cause or facilitate homodimerization.

In some embodiments, the endodomain is of a certain length. In specific embodiments, the length of the endodomain is between 70-250 amino acids, 70-225 amino acids, 70-200 amino acids, 70-175 amino acids, 70-150 amino acids, 70-125 amino acids, 70-100 amino acids, 80-250 amino acids, 80-225 amino acids, 80-200 amino acids, 80-175 amino acids, 80-150 amino acids, 80-100 amino acids, 90-250 amino acids, 90-225 amino acids, 90-200 amino acids, 90-175 amino acids, 90-150 amino acids, 90-125 amino acids, 90-100 amino acids, 100-250 amino acids, 100-225 amino acids, 100-200 amino acids, 100-175 amino acids, 100-150 amino acids, 100-125 amino acids, 125-250 amino acids, 125-225 amino acids, 125-200 amino acids, 125-175 amino acids, 125-150 amino acids, 150-250 amino acids, 150-225 amino acids, 150-200 amino acids, 150-175 amino acids, 175-250 amino acids, 175-225 amino acids, 175-200 amino acids, 200-250 amino acids, 200-225 amino acids, and so on. In certain embodiments, these fragments of certain lengths retain signaling activity.

II. Cells Comprising the Engineered Cytokine Receptors

It is further envisaged that pharmaceutical composition(s) of the disclosure comprises a host cell expressing a constitutively active cytokine receptor, such as transformed or transfected with a vector encoding the engineered receptor. The host cell may be produced by introducing a vector encoding the receptor. A nucleic acid molecule or vector encoding the engineered receptor introduced into the host cell may either integrate into the genome of the host or it may be maintained extrachromosomally.

The host cell can be any prokaryote or eukaryotic cell, but in specific embodiments it is a eukaryotic cell. In specific embodiments, the host cell is a bacterium, an insect, fungal, plant or animal cell. It is particularly envisaged that the host cell may be a mammalian cell, more preferably a human cell or human cell line. Particularly preferred host cells comprise immune cells, such as T-cells, NK cells, or NKT-cells.

In one embodiment, the host cell is a T-cell comprising an engineered cytokine receptor. In some cases, the cell that expresses the engineered cytokine receptor also expresses another non-naturally occurring molecule, such as an engineered T-cell receptor. Naturally occurring T-cell receptors comprise two subunits, an α-subunit and a 0-subunit, each of which is a unique protein produced by recombination event in each T-cell's genome. Libraries of TCRs may be screened for their selectivity to particular target antigens. An "engineered TCR" refers to a natural TCR, which has a high-avidity and reactivity toward target antigens that is selected, cloned, and/or subsequently introduced into a population of T-cells used for adoptive immunotherapy. In some cases, the cell that expresses the engineered cytokine receptor also expresses a chimeric antigen receptor (CAR). In contrast to engineered TCRs, CARs are engineered to bind target antigens in an MHC independent manner. In particular embodiments, a CAR comprises an extracellular binding domain including, but not limited to, an antibody or antigen binding fragment thereof such as an scFv); a transmembrane domain; one or more intracellular costimulatory signaling domains and a primary signaling domain.

IV. Therapeutic Uses of Host T-cells Expressing the Receptor

Provided herein is a method of treating a cancer comprising administering to an individual having said cancer an effective amount of T-cells expressing a CAR specific to the cancer, wherein the CAR T-cells additionally express a constitutively active cytokine receptor. In a more specific embodiment, the cancer is a solid tumor, including glioblastoma, for example. In another specific embodiment, the CAR T-cells target the antigen GD2. In a more specific embodiment, the constitutively active cytokine receptor comprises a transmembrane domain derived from IL-7 receptor alpha, wherein the transmembrane domain comprises one or more mutations that promote homodimerization of the cytokine receptor.

In particular methods of treatment of cancer, the cells are T-cells that comprise a cytokine receptor having a transmembrane domain having one or more mutations, and in specific embodiments the transmembrane domain includes the sequence in SEQ ID NO:1. In particular embodiments the transmembrane domain in the T-cells for treatment includes the sequence in one of SEQ ID NO:2 to SEQ ID NO:24.

An effective amount of the cells expressing the constitutively active cytokine receptor are provided to an individual in need thereof. The individual may have cancer, in certain cases, yet in other cases the individual is in need of treatment for a non-cancerous disease. A therapeutically effective amount of the cells are provided to the individual and may be provided in one or multiple administrations. In some cases, the cell therapy of the disclosure are provided to an individual in addition to one or more other types of therapy for the individual that may or may not simultaneously be provided.

By way of illustration, cancer patients or patients susceptible to cancer or suspected of having cancer may be treated as described herein. Immune cells modified as described herein may be administered to the individual and retained for extended periods of time. One of a variety of administration routes may be utilized. In some embodiments, the genetically modified cells are encapsulated to inhibit immune recognition and administered locally, for example at the site of the tumor.

In various embodiments the expression constructs, nucleic acid sequences, vectors, host cells and/or pharmaceutical compositions comprising the same are used for the prevention, treatment or amelioration of a cancerous disease, such as a tumorous disease. In particular embodiments, the pharmaceutical composition comprising cells of the present disclosure may be particularly useful in preventing, ameliorating and/or treating cancer, including cancer having solid tumors, for example.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

The methods and compositions described herein can be applied to a broad range of immune cells, such as, but not limited to αβ T-cells, γδ T-cells, NK cells, NKT-cells, Mucosa Associated Invariant T-cells (MAIT T-cells), innate lymphoid cells, or a mixture thereof. In addition, the invented receptor may be expressed in stem and/or progenitor cells that are subsequently differentiated into the aforementioned immune cells. In addition, all aforementioned immune cells could be redirected to tumor cells with a second genetic modification, for example but not limited to chimeric antigen receptors (CARs), bispecific T-cell engager (BiTE or T-cell ENG), Dual-Affinity Re-Targeting (DART) protein, or αβ T-cell receptors. In certain embodiments, the cells are CAR-expressing immune cells, as defined above, or antigen specific immune cells (such as a viral specific T-cell, or tumor antigen specific T-cell) that target the tumors. In examples wherein the constitutively active cytokine receptor-expressing cells also express a CAR, the CAR may be directed to any tumor antigen, such as EphA2, EphA3, HER2 (ERBB2), GD2, Glypican-3, 5T4, 8H9, $\alpha_v\beta_6$ integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD96, CD123, CD138, CD171, CEA, CLL-1, CSPG4, EGFR, EGFRvIII, EGP2, EGP40, EPCAM, ERBB3, ERBB4, ErbB3/4, FAP, FAR, FBP, fetal AchR, Folate Receptor u, GD2, GD3, HLA-AI MAGE A1, HLA-A2, IL13Ra2, KDR, Lambda, Lewis-Y, MCSP, Mesothelin, Mucd, Muc16, NCAM, NKG2D ligands, NY-ESO-1, PRAME, PSCA, PSC1, ROR1, Sp17, TAG72, TEM8, Tn-O-glycopeptide, VEGRR2, carcinoembryonic antigen, HMW-MAA, VEGF receptors, TSHR, CS-1, CMA, Tn Ag, prostate specific membrane antigen (PSMA), FLT3, CD44v6, KIT, interleukin-11 receptor a (IL-1 lRa), PRSS21, VEGFR2, CD24, platelet-derived growth factor receptor-beta (PDGFR-beta), SSEA-4, ERBB2 (Her2/neu), Prostase, PAP, ELF2M, Ephrin B2, IGF-I receptor, CAIX, LMP2, gplOO, bcr-abl, tyrosinase, EphA2, Fucosyl GM1, sLe, GM3, TGS5, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WTi, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-l/Galectin 8, MelanA/ MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B 1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLECi2A, BST2, EMR2, LY75, GPC3, FCRL5, and 1GLL1 and/or other exemplary antigens that are present within the extracellular matrix of tumors, such as oncofetal variants of fibronectin, tenascin, or necrotic regions of tumors and other tumor-associated antigens or actionable mutations that are identified through genomic analysis and or differential expression studies of tumors, for example.

Also provided herein is a method of treating cancer in an individual, wherein the cancer expresses a tumor antigen, comprising administering to the individual an immune cell expressing (1) a chimeric antigen receptor that targets said tumor antigen; and (2) a constitutively-active cytokine receptor. The constitutively-active cytokine receptor may be any of the constitutively-active cytokine receptors encompassed herein. In certain embodiments, the constitutively-active cytokine receptor comprises an interleukin-7 (IL-7) receptor endodomain and a transmembrane domain that promotes homodimerization of the cytokine receptor such that the cytokine receptor is constitutively active. In certain embodiments, the constitutively-active cytokine receptor comprises an interleukin-21 (IL-21) receptor endodomain and a transmembrane domain that promotes homodimerization of the cytokine receptor such that the cytokine receptor is constitutively active. In certain embodiments, the constitutively-active cytokine receptor comprises an interleukin-23 (IL-23) receptor endodomain and a transmembrane domain that promotes homodimerization of the cytokine receptor such that the cytokine receptor is constitutively active. In certain embodiments, the constitutively-active cytokine receptor comprises an interleukin-12 (IL-12) receptor endodomain and a transmembrane domain that promotes homodimerization of the cytokine receptor such that the cytokine receptor is constitutively active. In specific embodiments, the transmembrane domain comprises the sequence of any of SEQ ID NOS:1-24. In a specific embodiment of any of the foregoing, the constitutively-active cytokine receptor comprises an extracellular domain that does not transmit a signal when the cognate cytokine binds to the extracellular domain. For example, in a more specific embodiment, the constitutively-active cytokine receptor comprises an IL-7 receptor endodomain, and the cognate cytokine is IL-7. In a specific embodiment of any of the foregoing, the constitutively active cytokine receptor comprises an extracellular domain that is an extracellular domain from CD34. In another specific embodiment of any of the foregoing, the constitutively active cytokine receptor comprises the extracellular domain that is an extracellular domain from PD-1 or B7.

In a specific embodiment of any of the methods of treatment provided herein, the cancer is glioblastoma. In certain specific embodiments of the methods provided herein, the cancer is breast cancer, prostate cancer, lung cancer (e.g., small cell lung cancer or non-small cell lung cancer), brain cancer, colon cancer, head and neck cancer, skin cancer (e.g., melanoma), ovarian cancer, endometrial cancer, cervix cancer, kidney cancer, gastric cancer, cancer of the small intestine, liver cancer, pancreatic cancer, gall bladder cancer, a cancer of the bile duct, esophageal cancer, cancer of the salivary glands or cancer of the thyroid gland.

In a specific embodiment of any of the methods provided herein, the tumor antigen is GD2. In another specific embodiment of any of the methods provided herein, the tumor antigen is EphA2. In other specific embodiments of the methods provided herein, the tumor antigen is EphA3, HER2 (ERBB2), GD2, Glypican-3, 5T4, 8H9, αvβ6 integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD96, CD123, CD138, CD171, CEA, CLL-1, CSPG4, EGFR, EGFRvIII, EGP2, EGP40, EPCAM, ERBB3, ERBB4, ErbB3/4, FAP, FAR, FBP, fetal AchR, Folate Receptor u, GD2, GD3, HLA-AI MAGE A1, HLA-A2, IL13Ra2, KDR, Lambda, Lewis-Y, MCSP, Mesothelin, Mucd, Muc16, NCAM, NKG2D ligands, NY-ESO-1, PRAME, PSCA, PSC1, ROR1, Sp17, TAG72, TEM8, Tn-O-glycopeptide, VEGFR2, carcinoembryonic antigen, HMW-MAA, VEGF receptors, TSHR, CS-1, CMA, Tn Ag, prostate specific membrane antigen (PSMA), FLT3, CD44v6, KIT, interleukin-11 receptor a (IL-1 lRa), PRSS21, VEGFR2, CD24, platelet-derived growth factor receptor-beta (PDGFR-beta), SSEA-4, ERBB2 (Her2/neu), Prostase, PAP, ELF2M, Ephrin B2, IGF-I receptor, CAIX, LMP2, gplOO, bcr-abl, tyrosinase, EphA2, Fucosyl GM1, sLe, GM3, TGS5, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-l/Galectin 8, MelanA/MARTI, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES 1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or lGLL1.

In some embodiments, the constitutively active cytokine receptor-expressing cells are provided to an individual for a medical condition other than cancer, including another disease in which lymphocyte therapy is therapeutic including, but not limited to, infectious diseases, autoimmune diseases, and complications for post solid organ and stem cell transplantation. In such cases, the T-cells are desired to have enhanced expansion, and so the constitutively active cytokine receptor molecules are the same or similar to those for cancer indications, but the cell may be modified specifically for targeting non-malignant indications. In embodiments wherein the individual has an autoimmune disease, for example, the cells may be broadly specific for autoreactive T-cells via their TCRs, for example using the autoreactive T-cells as antigens (as in OPEXA® Therapeutics; The Woodlands, TX).

In particular embodiments, the present disclosure contemplates, in part, cells harboring expression constructs, nucleic acid molecules and/or vectors that can administered either alone or in any combination with another therapy, and in at least some aspects, together with a pharmaceutically acceptable carrier or excipient. In certain embodiments, prior to administration of the cells, said nucleic acid molecules or vectors may be stably integrated into the genome of the cells. In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying the above identified diseases.

Furthermore, the disclosure relates to a method for the prevention, treatment or amelioration of a cancerous (including tumorous) disease comprising the step of administering to a subject in need thereof an effective amount of cells harboring a constitutively active cytokine receptor, nucleic acid sequence that encodes them, vector(s) that encodes them, as contemplated herein and/or produced by a process as contemplated herein.

Possible indications for administration of the composition(s) of the exemplary modified immune cells are cancerous diseases, including tumorous diseases, including breast, prostate, lung, brain, colon, head and neck cancer, skin cancer, ovarian cancer, endometrial cancer, cervix cancer, kidney cancer, lung cancer, gastric cancer, cancer of the small intestine, liver cancer, pancreatic cancer, gall bladder cancer, cancers of the bile duct, esophagus cancer, cancer of the salivary glands and cancer of the thyroid gland as well as hematological malignancies of T-cells, B-cells, NK-cells and myeloid cells or their precursors. Exemplary indications for administration of the composition(s) of cells are cancerous diseases, including any malignancies having cells that express an antigen to which the receptor-expressing cells are targeted, for example. In addition, it includes malignancies that aberrantly express other tumor antigens and those may also be targeted. The administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before and/or after the administration of the other component. Particular combination therapies include chemotherapy, radiation, surgery, hormone therapy, or other types of immunotherapy.

Embodiments relate to a kit comprising one or more immune cells as described herein, a nucleic acid sequence as described herein, a vector as described herein and/or a host as described herein. It is also contemplated that the kit of this disclosure comprises a pharmaceutical composition as described herein above, either alone or in combination with further medicaments to be administered to an individual in need of medical treatment or intervention.

The immune cells (such as T-cells or NK cells) that have been modified with the construct(s) may then be grown in culture under selective conditions (in some cases only) and cells that are selected as having the construct may then be expanded and further analyzed, using, for example; the polymerase chain reaction for determining the presence of the construct(s) in the host cells. Once the modified host cells have been identified, they may then be used as planned, e.g., expanded in culture or introduced into a host organism.

Depending upon the nature of the cells, the cells may be introduced into a host organism, e.g., a mammal, in a wide variety of ways. The cells may be introduced at the site of the tumor, in specific embodiments, although in alternative embodiments the cells home to the cancer or are modified to home to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest or may be delivered intravenously. The cells may be in a physiologically-acceptable medium.

Routes of administration include intravenous, subcutaneous, intraperitoneal, intramuscular, topical or intradermal administration, for example. In some cases, a particular dose of cells is provided to the individual, such as from $10^4$ to $10^{11}$ cells total, for example. In specific embodiments, a dosage of $1\times10^5$ cells/kg to $1\times10^9$ cells/kg may be employed. Particular doses include from $1\times10^6$ cells/mL to $1\times10^8$ cells/mL.

The vector introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

It should be appreciated that the system may be subject to variables, such as the efficiency of expression, the activity of the expression product, the particular need of the patient, which may vary with time and circumstances, the rate of loss of the cellular activity as a result of loss of cells or expression activity of individual cells, and the like. Therefore, it is expected that for each individual patient, each patient would be monitored for the proper dosage for the individual, and such practices of monitoring a patient are routine in the art.

V. Vectors Generally

Vectors of the disclosure may be used for recombinant engineering to produce and at least in some cases express, a constitutively active cytokine receptor.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, transposons, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 to 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5'-non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The identity of tissue-specific promoters or elements, as well as assays to characterize their activity, is well known to those of skill in the art. In specific embodiments, environment-specific promoters or elements are utilized, such as hypoxic-specific regulatory elements. Tissue-specific, lineage-specific, and/or activation-specific promoters may be employed, and examples include activated T-cell elements, NFAT (lineage-restricted activation), Early growth response gene (activation), liver X receptor response elements (activation), Hypoxia Response elements (environmental), etc.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature.

D. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present disclosure may be a viral vector that encodes heparanase. Non-limiting examples of virus vectors that may be used to deliver a nucleic acid of the present disclosure are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present disclosure as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a heparanase retroviral vector, a nucleic acid (e.g., one encoding part or all of heparanase) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present disclosure. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

E. Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

F. Ex Vivo Transformation

Methods for transfecting eukaryotic cells and tissues removed from an organism in an ex vivo setting are known to those of skill in the art. Thus, it is contemplated that cells or tissues may be removed and transfected ex vivo using heparanase or other nucleic acids of the present disclosure. In particular aspects, the transplanted cells or tissues may be placed into an organism. In preferred facets, a nucleic acid is expressed in the transplanted cells.

VI. Combination Therapy

In certain embodiments of the disclosure, methods of the present disclosure for clinical aspect, e.g., administration to an individual having a constitutively active cytokine receptor-expressing cells, such as immune cells, e.g., T-cells, expressing a constitutively active cytokine receptors, may be combined with one or more other agents effective in the treatment of the medical condition for the individual (such as hyperproliferative disease, including anti-cancer agents). An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In embodiments of the disclosure in which an individual with cancer is in need of combination therapy, one or more of the following are provided to an individual in addition to the therapeutic cells of the disclosure: chemotherapy or other drugs, pattern-associated molecular patterns (PAMPs), such as toll like receptor (TLR) ligands, immunotherapy, radiation, surgery, hormone therapy, and a combination thereof. In cases where an immunotherapy is provided to the individual, the immunotherapy may or may not be part of the constitutively active cytokine receptor-expressing cells. In some cases, the constitutively active cytokine receptor-expressing cells comprise other receptors or molecules that themselves provide therapy for the individual, such as binding a tumor antigen or viral antigen.

Tumor cell resistance to chemotherapy and radiotherapy agents represents a major problem in clinical oncology. One goal of current cancer research is to find ways to improve the efficacy of chemo- and radiotherapy by combining it with other therapies. In the context of the present disclosure, it is contemplated that cell therapy could be used similarly in conjunction with chemotherapeutic, radiotherapeutic, or immunotherapeutic intervention, in addition to other pro-apoptotic or cell cycle regulating agents.

The methods and compositions of the present disclosure may precede or follow one or more other agent treatment by intervals ranging from minutes to weeks. In embodiments where the other agent and that of the present disclosure are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

In cases wherein another therapy is provided in conjunction with the cells of the disclosure and multiple administrations of one or both are needed, the administration of the agents may be of different administration routes and at different times.

A. Chemotherapy

Cancer therapies also include a variety of combination therapies, for example with both chemical and radiation based treatments. Examples of chemotherapies that may be utilized with the therapeutic cells of the disclosure include, for example, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone: didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin;

methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin: neridronic acid; nilutamide; nisamycin; nitric oxide modulators; nitroxide antioxidant; nitrullyn; oblimersen (GENASENSE®); 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

In one embodiment, an immunotherapy other than the constitutively active cytokine receptor-specific-expressing cells is employed along with the methods and compositions of the present disclosure. Such therapy may or may not be the cells themselves.

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include T-cells, cytotoxic T-cells, NKT cells, NK cells, dendritic cells or macrophages.

Immunotherapy could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, p155, Melanoma-associated antigen (MAGE), Preferentially expressed antigen of melanoma (PRAME), survivin, CD19, CD20, CD22, k light chain, CD30, CD33, CD123, CD38, ROR1, ErbB2, ErbB3/4, ErbB dimers, EGFr vIII, carcinoembryonic antigen, EGP2, EGP40, mesothelin, TAG72, PSMA, NKG2D ligands, B7-H6, IL-13 receptor a2, MUC1, MUC16, CA9, GD2, GD3, HMW-MAA, CD171, Lewis Y, CLL-1, G250/CAIX, HLA-AI MAGE A1, HLA-A2 NY-ESO-1, PSCA, folate receptor-α, CD44v6, CD44v7/8, avb6 integrin, 8H9, NCAM, VEGF receptors, 5T4, Foetal AchR, NKG2D ligands, CD44v6, dual antigen, universal, EphA2, EphA3, HER2 (ERBB2), GD2, Glypican-3, 5T4, 8H9, Wv06 integrin, B cell maturation antigen (BCMA) B7-H3, B7-H6, CAIX, CA9, CD19, CD20, CD22, kappa light chain, CD44, CD44v6, CD44v7/8, CD70, CD96, CD123, CD138, CD171, CEA, CLL-1, CSPG4, EGFR, EGFRvIII, EPCAM, ERBB3, ERBB4, FAP, FAR, FBP, fetal AchR, IL1 lRa, KDR, Lambda, MCSP, NCAM, PSC1, PSMA, ROR1, Sp17, SURVIVIN, TAG72, TEM1, TEM8, Tn-O-glycopeptide, VEGRR2, and HMW-MAA.

Another type of immunotherapy uses PAMPs. These may be injected into the tumor to activate innate immunity, that in turn recruits and activates adaptive immunity including the present constitutively active cytokine receptor-specific-expressing cells.

D. Genes

In yet another embodiment, the secondary treatment is a gene therapy in which a therapeutic polynucleotide is administered before, after, or at the same time as the present disclosure clinical embodiments. A variety of expression products are encompassed within the disclosure, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present disclosure may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VII. Pharmaceutical Compositions

In accordance with this disclosure, the term "pharmaceutical composition" relates to a composition for administration to an individual. In specific aspects of the disclosure, the pharmaceutical composition comprises a plurality of immune cells that express one or more constitutively active cytokine receptors. In a preferred embodiment, the pharmaceutical composition comprises a composition for parenteral, transdermal, intraluminal, intra-arterial, intrathecal or intravenous administration or for direct injection into a cancer. It is in particular envisaged that said pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A preferred dosage for administration might be in the range of $1\times10^7/m^2$ to $1\times10^{10}/m^2$. Progress can be monitored by periodic assessment. constitutively active cytokine receptor-modified cells (such as T-cells) may administered via intravenous infusion. Doses can range from $1\times10^7/m^2$ to $1\times10^{10}/m^2$.

The compositions of the disclosure may be administered locally or systemically. Administration will generally be parenteral, e.g., intravenous; DNA may also be administered directly to the target site, e.g., by biolistic delivery to an internal or external target site or by catheter to a site in an artery. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the constitutively active cytokine receptor constructs or nucleic acid molecules or vectors encoding the same (as described in this disclosure), further biologically active agents, depending on the intended use of the pharmaceutical composition.

Any of the compositions described herein may be comprised in a kit for treating cancers expressing the constitutively active cytokine receptor. In a non-limiting example, one or more constitutively active cytokine receptor-directed immune cells for use in cell therapy and/or the reagents to generate one or more cells for use in cell therapy that harbors recombinant expression vectors may be comprised in a kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

In particular embodiments, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes an engager molecule as described herein and/or regulatory elements therefore.

In particular embodiments, there are one or more apparatuses in the kit suitable for extracting one or more samples from an individual. The apparatus may be a syringe, scalpel, and so forth.

In particular aspects, the kit comprises the cell therapy of the disclosure and also the chemotherapy for which the cells are immune. In some cases, the kit, in addition to the cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Constitutively Active Cytokine Receptors for Cell Therapy

Figure 2:
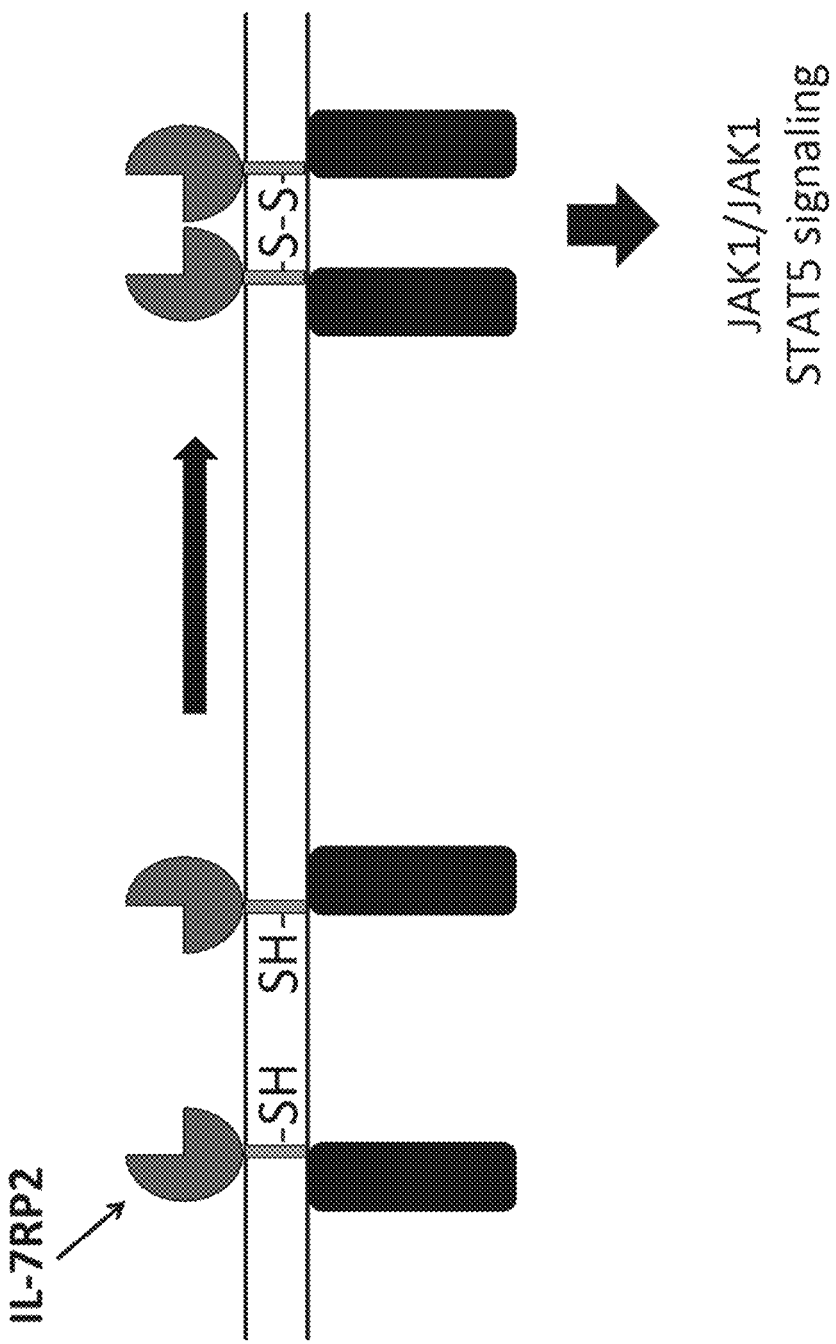
FIG. 2: Scheme of signaling at the IL7RP2 receptor.

The present example demonstrates the generation and activity of particular specific embodiments of constitutively active cytokine receptors. The present disclosure concerns constitutively active cytokine receptors that are non-natural and have been modified compared to wildtype that leads to changes in signaling properties. FIG. 1 illustrates what occurs in normal IL-7 cytokine/receptor signaling. At rest, the IL-7 receptor alpha (IL-7Rα) protein remains separated from the gamma-chain receptor (γc) protein. This changes when extracellular IL-7 binds the extracellular domains of both receptors, induces heterodimerization of IL-7Rα and γc, which activates JAK1/JAK3 signaling to activate STAT5 phosphorylation. STAT5 is the primary downstream signaling node activated by the IL-7 receptor. FIG. 2 shows signaling at the IL7RP2 receptor. Independently of extracellular IL-7, the cysteine residue in the transmembrane domain of the IL7RP2 monomer protein will form a disulfide bond with the cysteine residue in another IL7RP2 monomer. This induces formation of a homodimer protein that constitutively activates JAK1/JAKI signaling resulting in STAT5 phosphorylation.

Figure 3:
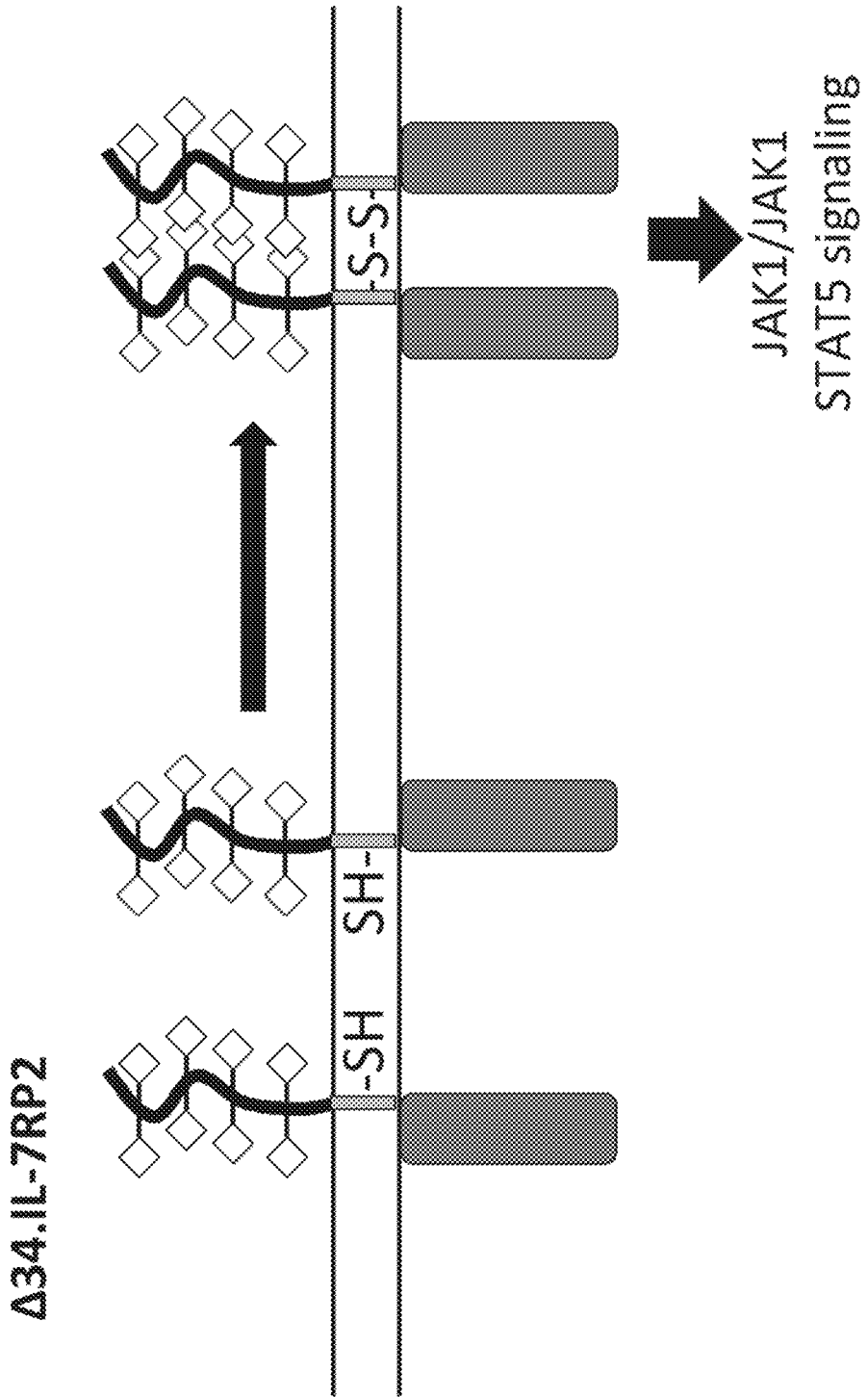
FIG. 3: Scheme of signaling in the Δ34.IL7RP2 protein.
Figure 4B:
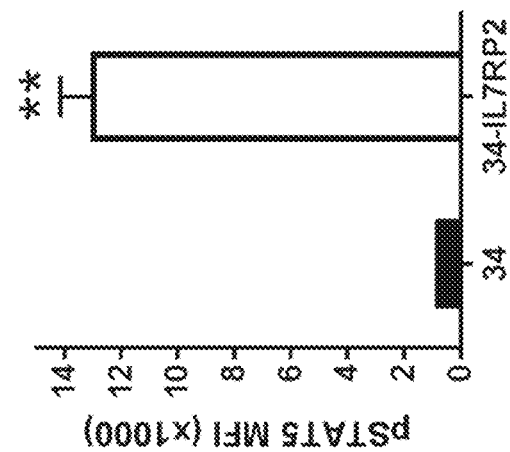
FIGS. 4A and 4B: STAT5 is constitutively active in IL7RP2-transduced T-cells.
Figure 4A:
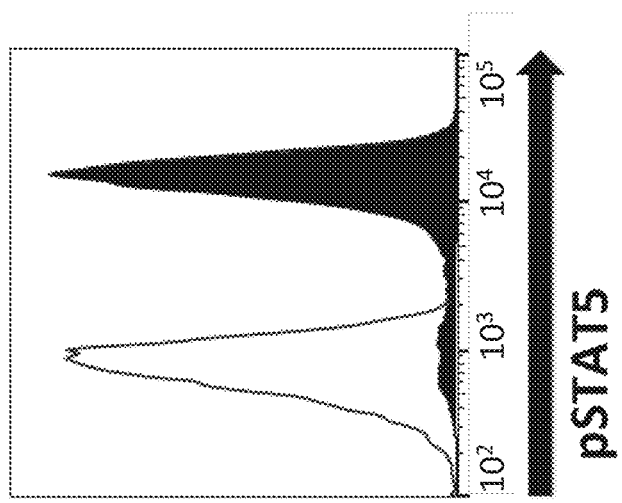

Thus, the present disclosure encompasses embodiments of engineered cytokine receptors that in some cases have a particular extracelullular domain and a particular transmembrane domain such that the engineered receptor is constitutively active even in the absence of an initial signal for the receptor. In FIG. 3, there is illustrated signaling in the particular example of a Δ34.IL7RP2 protein. The extracellular domain of the IL7RP2 receptor was replaced with the extracellular domain of CD34 to form Δ34.IL7RP2. This ablates sensitivity to extracellular cytokines such as IL-7, while maintaining the transmembrane and cytoplasmic domains of the protein intact to constitutively activate STAT5. FIG. 4 shows that STAT5 is constitutively active in IL7RP2-transduced T cells. A retroviral vector with an expression cassette encoding Δ34.IL7RP2 (SFG.Δ34.IL7RP2) was generated. OKT3/CD28-activated T cells were transduced with RD114-pseudotyped SFG.Δ34.IL7RP2 retroviral particles. As a negative control, T-cells were separately transduced with a non-signaling SFG.Δ34 vector, which expresses the extracellular and transmembrane domains and a portion of the cytoplasmic domain of CD34. In representative FACs data from one donor (FIG. 4A), constitutive STAT5 activation is demonstrated by higher phosphorylated-STAT5 (pSTAT5) signal in Δ34.IL7RP2 transduced T-cells (white) rested without cytokines for 24 hours, relative to T-cells transduced with SFG.Δ34 (black). Averaging results from n of 3 donors showed that the mean fluorescence intensity (MFI) of pSTAT5 in Δ34.IL7RP2 transduced T-cells is significantly higher than SFG.Δ34 (FIG. 4B).

Figure 5:
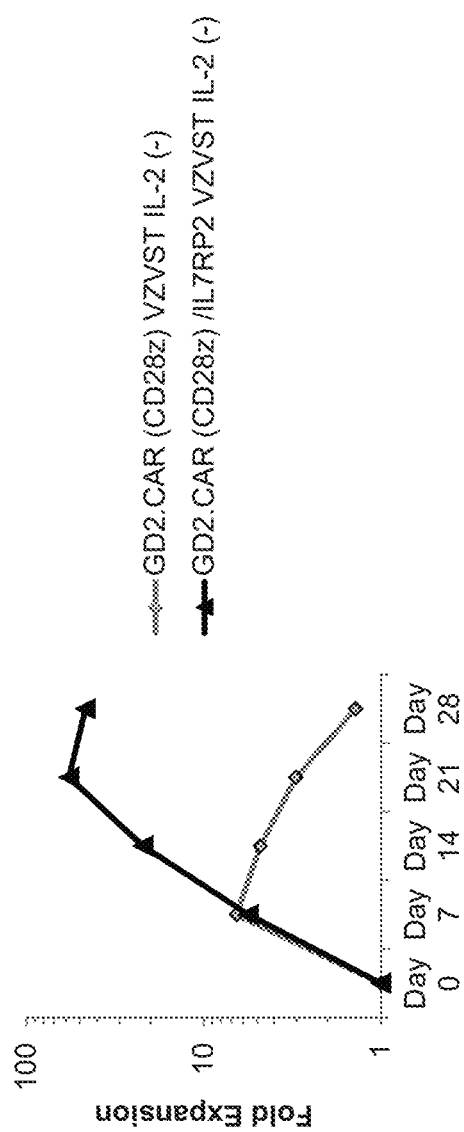
FIG. 5: IL7RP2-transduced, antigen-specific T-cells have greater proliferative potential then unmodified, antigen-specific T-cells after antigen-specific stimulation.

Cells comprising modified cytokine receptors of the disclosure and also comprising a chimeric antigen receptor (for example) maintain the ability to proliferate even in the absence of the cytokine. In FIG. 5, it is shown that IL7RP2-transduced, antigen-specific T-cells have greater proliferative potential then unmodified, antigen-specific T cells after antigen-specific stimulation. Varicella zoster virus (VZV)-specific T-cells (VZVSTs) were genetically modified with a chimeric antigen receptors (CARs) specific for the solid tumor antigen GD2. The benefit of IL7RP2 in this system was evaluated. VZVSTs were genetically modified with a retroviral vector encoding a GD2-CAR with a CD28.-ξ signaling domain (SFG.GD2.CAR.CD28 ξ) or SFG.GD2.CAR.CD28ξ and SFG.IL7RP2-mOrange (mO). Both T-cell populations were repeatedly exposed to GD2+ LAN-1 tumor cells in the absence of IL2. While L7RP2-transduced GD2.CAR VZVST continued to proliferate, unmodified GD2.CAR VZVST did not.

Figure 6A:
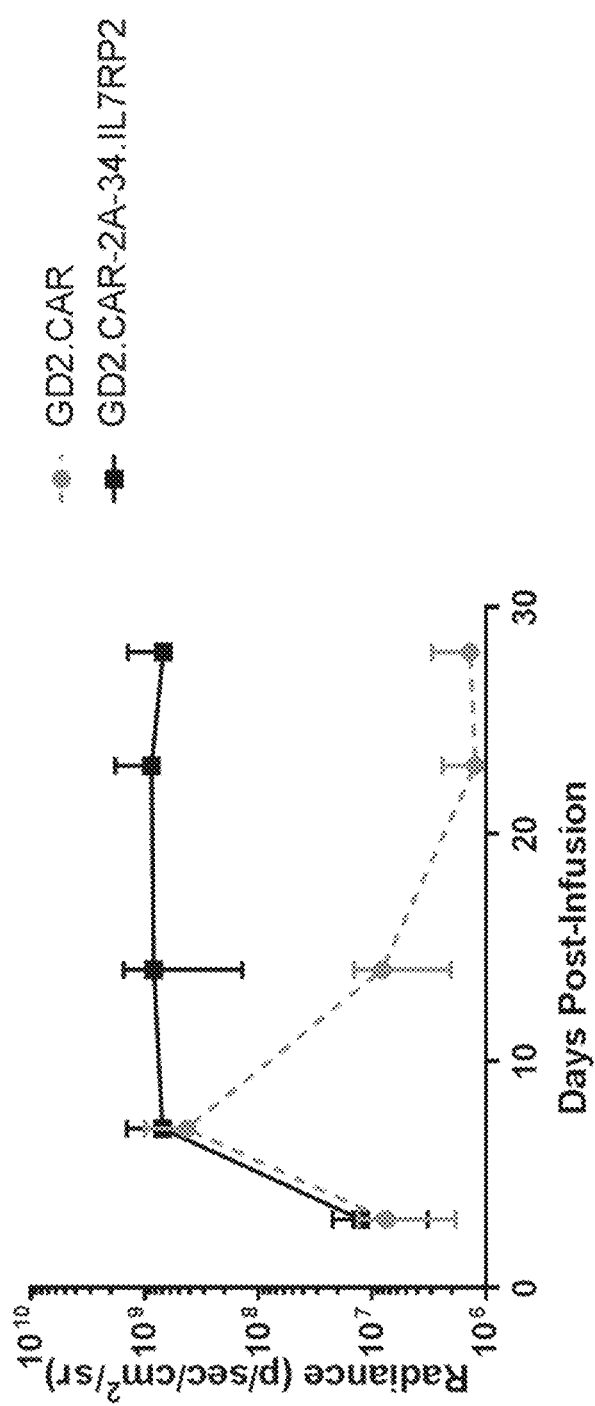
FIGS. 6A, 6B, and 6C: GD2.CAR T-cells co-expressing Δ34.IL7RP2 have greater expansion and anti-tumor efficacy then GD2.CAR T-cells in vivo. GD2.CAR-Δ34.IL7RP2 T-cells significantly expanded in vivo and demonstrated prolonged T-cell persistence at the tumor site in comparison to GD2.CAR T-cells (FIG. 6A). LAN-1 tumors outgrew in mice receiving GD2.CAR T-cells, while tumors were eliminated in GD2.CAR-Δ34.IL7RP2 T-cells (FIG. 6B). This resulted in a significantly enhanced survival advantage in mice receiving GD2.CAR-Δ34.IL7RP2 T-cells (FIG. 6C).
Figure 6B:
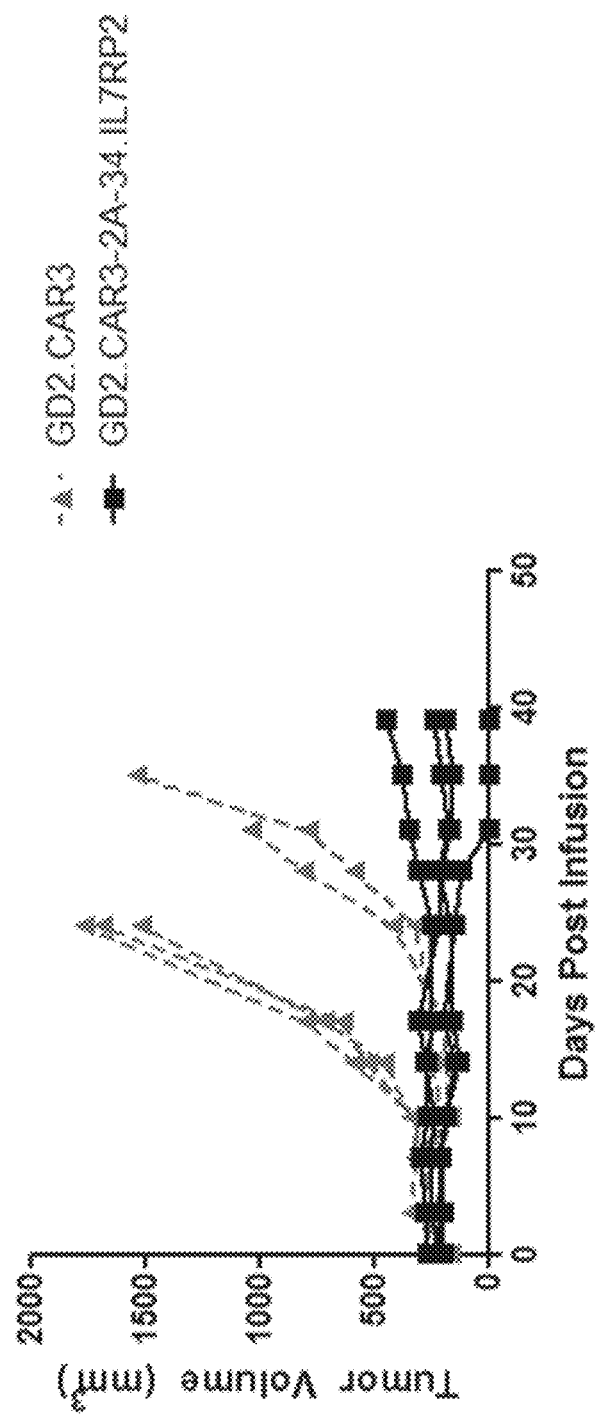
Figure 6C:
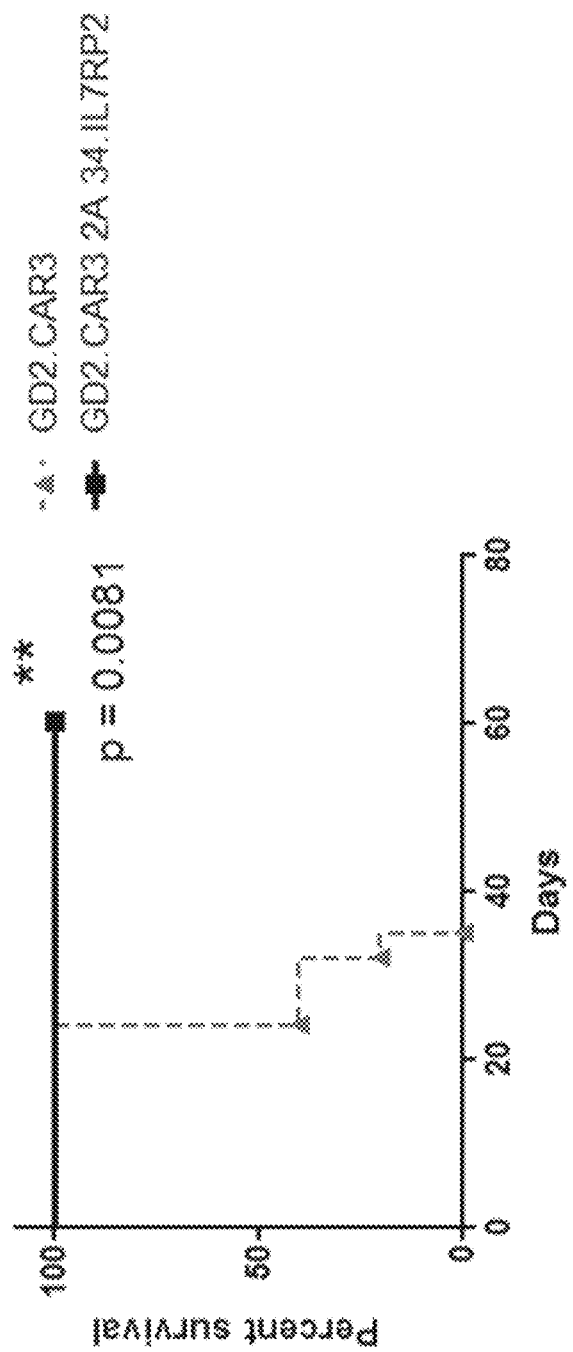

The constitutively active cytokine receptors of the present disclosure allow increased expansion and cancer cell cytotoxicity compared to cells that lack the receptors. FIG. 6 demonstrates that GD2.CAR T-cells co-expressing Δ34.IL7RP2 have greater expansion and anti-tumor efficacy then GD2.CAR T-cells in vivo. To evaluate if Δ34.IL7RP2 enhances the expansion of antigen-redirected T-cells in vivo, OKT3/CD28-activated T-cells were transduced with a retroviral vector encoding a GD2.CAR with an OX40.CD28.ξ signaling domain (SFG.GD2.CAR.OX40.CD28.Q) or a bicistronic SFG vector co-expressing GD2.CAR.OX40.CD28.ξ and Δ34.IL7RP2 with a 2A sequence in between. In addition, both T-cell populations were transduced with a retroviral vector encoding firefly luciferase to allow for noninvasive bioluminescence imaging. NSG mice with 8 day-old left dorsal flank GD2+ LAN-1 tumors were injected intravenously with 2 million GD2.CAR T cells or 2 million GD2.CAR-Δ34.IL7RP2 T cells. GD2.CAR-Δ34.IL7RP2 T-cells significantly expanded in vivo and demonstrated prolonged T-cell persistence at the tumor site in comparison to GD2.CAR T cells (FIG. 6A). LAN-1 tumors outgrew in mice receiving GD2.CAR T-cells, while tumors were eliminated in GD2.CAR-Δ34.IL7RP2 T cells (FIG. 6B). This resulted in a significantly enhanced survival advantage in mice receiving GD2.CAR-Δ34.IL7RP2 T cells (FIG. 6C).

Figure 7:
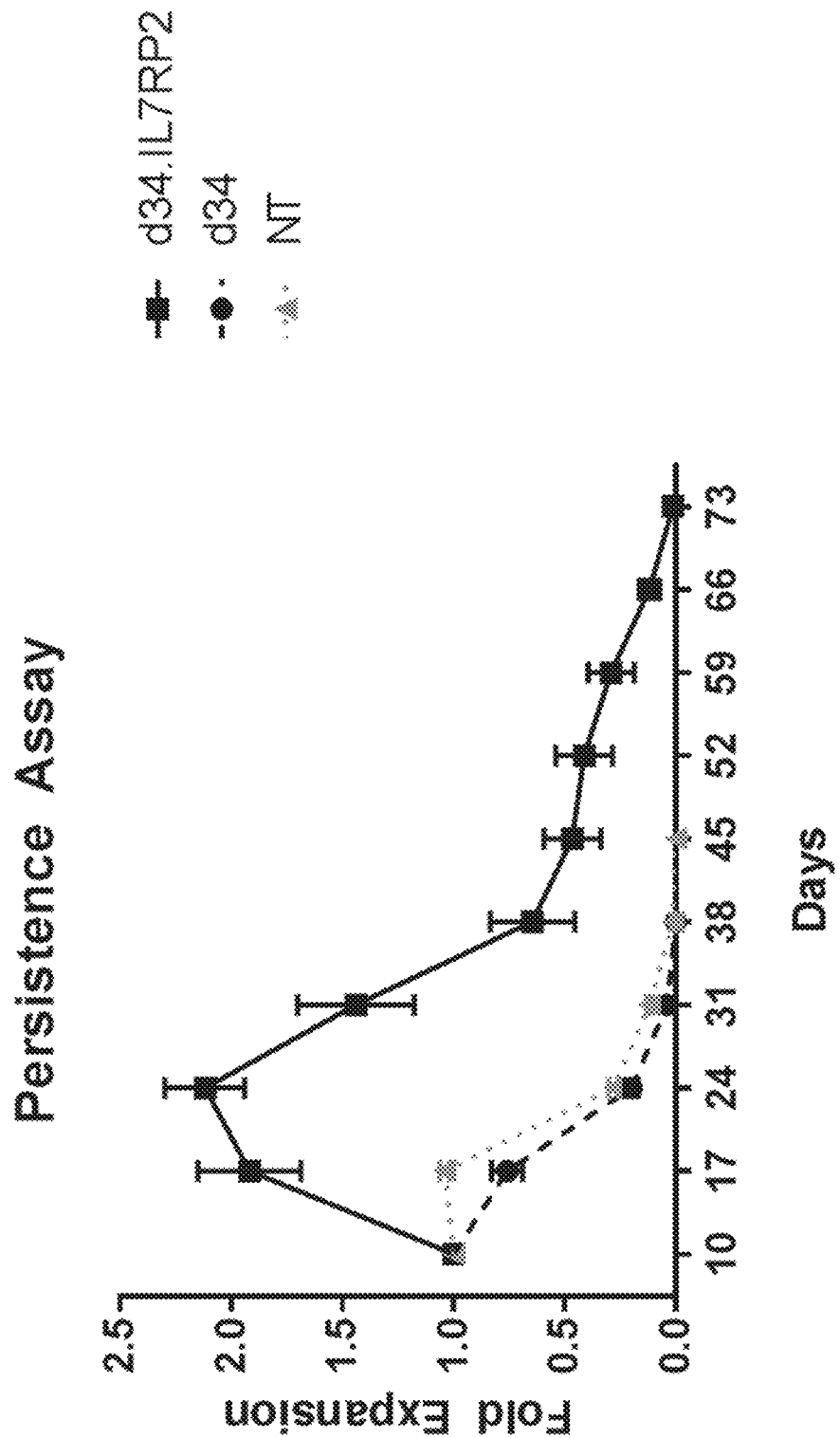
FIG. 7: Δ34.IL7RP2-transduced T-cells have limited persistence in the absence of antigen-stimulation.

Δ34.IL7RP2-transduced T-cells have limited persistence in the absence of antigen-stimulation. To evaluate if Δ34.IL7RP2 induced constitutively expansion of T-cells in the absence of antigen or cytokine stimulus, Δ34.IL7RP2-transduced T cells were cultured (10 days after PBMC isolation and activation) in complete culture media that was devoid of human cytokine supplement or antigen stimulus. As a control, Δ34-transduced T-cells and non-transduced (NT) T-cells were cultured in the same manner. Δ34.IL7RP2-transduced T-cells expand 1-fold during the first 14-days of culture, after which cells contracted (FIG. 7A). Δ34 and NT T-cells did not expand and contracted during the course of the culture. This demonstrates that Δ34.IL7RP2 alone is incapable of inducing constitutive cell expansion in T-cells and that Δ34.IL7RP2 transduced T-cells still require antigen for proliferation.

Figure 8:
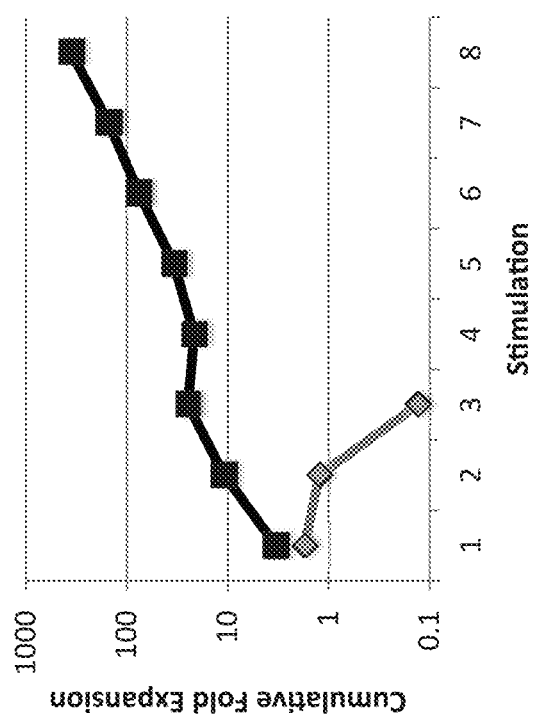
FIG. 8: Δ34.IL7RP2 prolongs cytotoxic capacity and expansion of EphA2.CAR T-cells.

Δ34.IL7RP2 prolongs cytotoxic capacity and expansion of EphA2.CAR T cells. To evaluate if Δ34.IL7RP2 enhances the expansion of T-cells of redirected against EphA2-expressing targets through the EphA2-CAR, OKT3/CD28-activated T cells were transduced with a bicistronic SFG vector encoding a EphA2.CAR with a 41BB.ξ signaling domain, connected by a 2A sequence to a truncated CD19 molecule, ΔCD19 (SFG.EphA2.41BB.ξ-2A-ΔCD19) or a bicistronic SFG vector co-expressing SFG.EphA2.41BB.ξ and Δ34.IL7RP2 with a 2A sequence in between (SFG.EphA2.41BB.ξ-2A-Δ34.IL7RP2). When the CAR T-cells were subjected to a serial killing assay where they were challenged with EphA2-positive U373 glioblastoma cells weekly (2 T-cell to 1 tumor cell ratio), SFG.EphA2.41BB.ξ-2A-Δ34.IL7RP2 T-cells could eliminate tumor cells and proliferate for 8 stimulations (black), while SFG.EphA2.41BB.ξ-2A-ΔCD19 T-cells (gray) became dysfunctional after 2 stimulations (FIG. 8).

Figure 9:
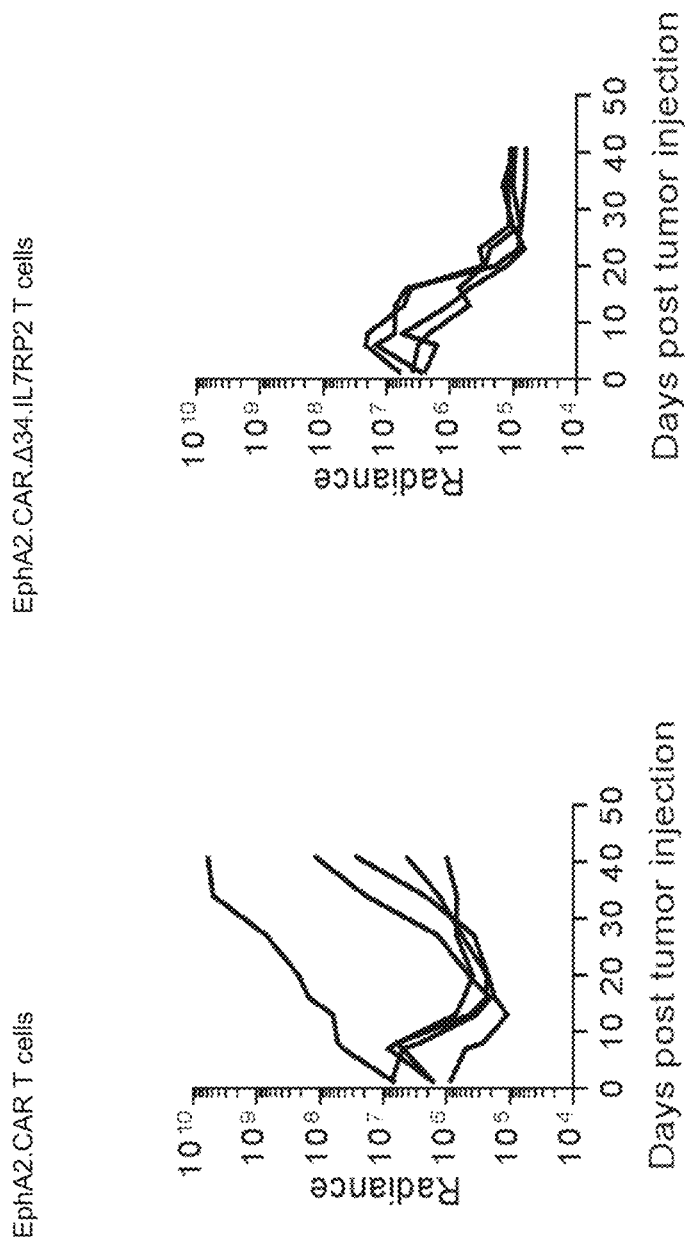
FIG. 9: Δ34.IL7RP2 enhances antiglioma activity of EphA2.CAR T-cells in vivo.

Δ34.IL7RP2 enhances antiglioma activity of EphA2.CAR T-cells in vivo. Mice were injected with fire fly luciferase expressing U373 cells and on day 7 received and intratumoral injection of EphA2.CAR T cells or EphA2.CAR.Δ34.IL7RP2 T-cells. Tumor growth was followed by serial bioluminescence imaging. Tumors regressed in all four mice treated with EphA2.CAR.Δ34.IL7RP2 T-cell and did not recur (FIG. 9). In contrast only 4/5 mice had tumor regression after EphA2.CAR T-cell therapy and all four responding tumors recurred within 4 weeks post T-cell injection.

Figure 10A:
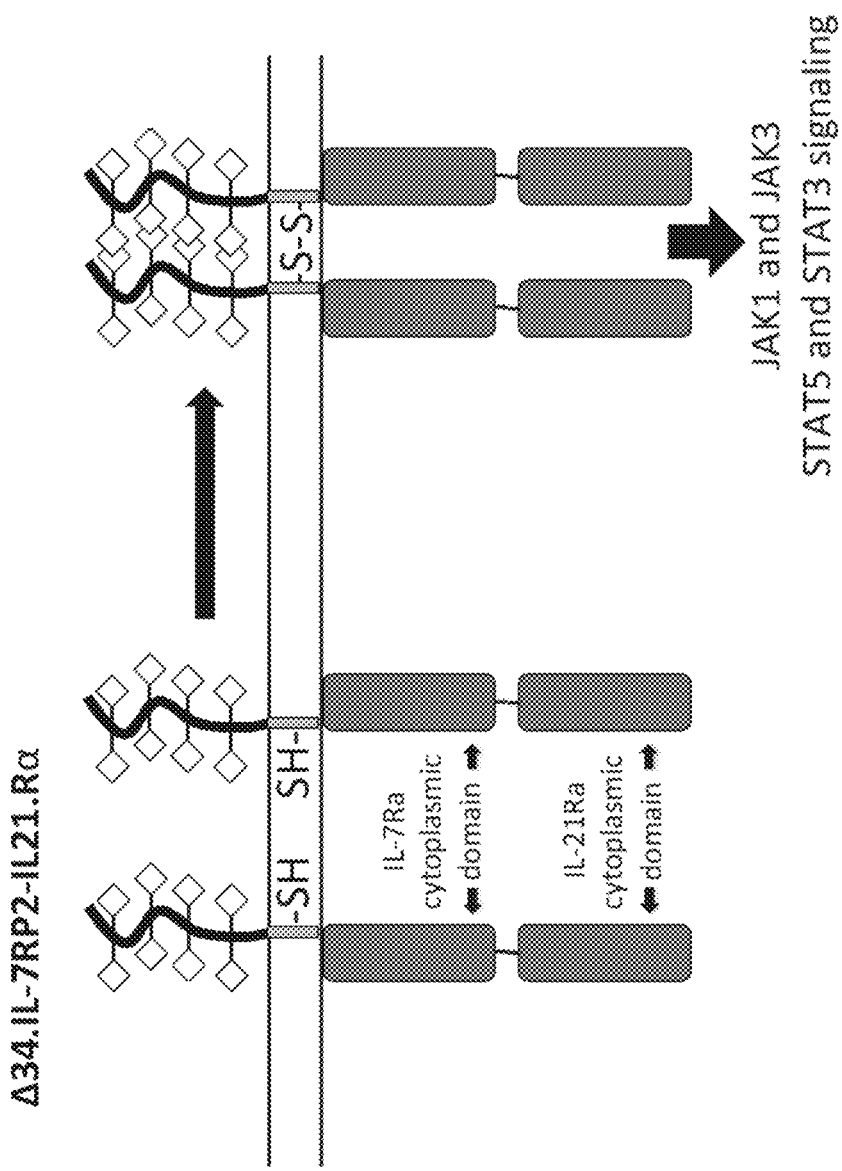
FIGS. 10A, 10B, and 10C: The Δ34.IL7RP2 protein can be fused with the IL-21Rα cytoplasmic domain to generate constitutively active combinatorial cytokine receptors. Schematic of activation of Δ34.IL7RP2-linker-IL21Rα (FIG. 10A). Constitutive activation of STAT5 by Δ34.IL7RP2 and Δ34.IL7RP2-linker-IL21Rα T-cells (FIG. 10B) and constitutive activation of STAT3 by only Δ34.IL7RP2-linker-IL21Rα (FIG. 10C).
Figure 10B:
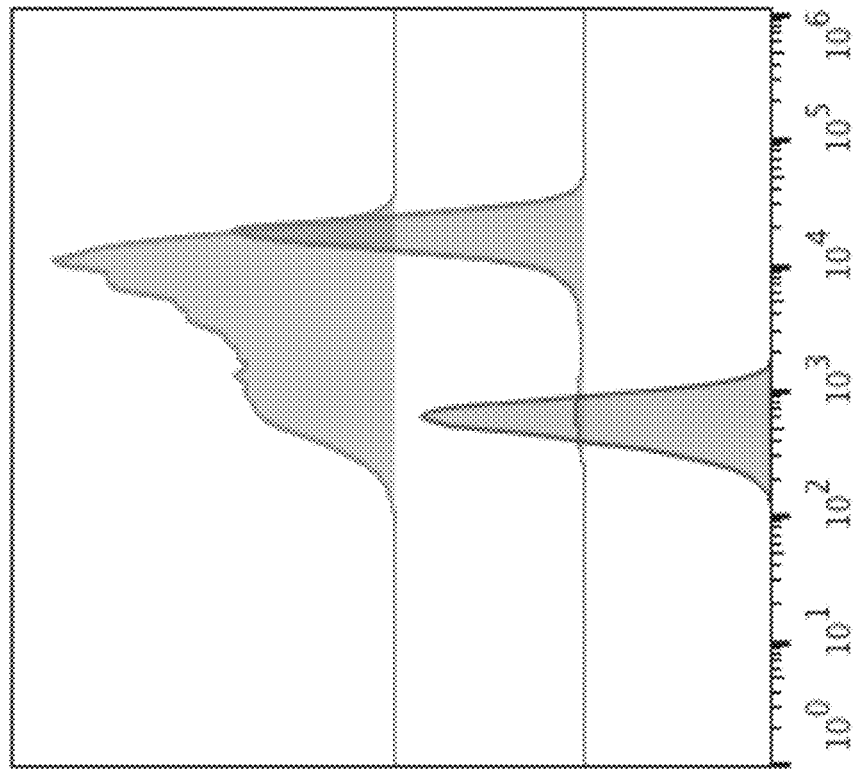
Figure 10C:
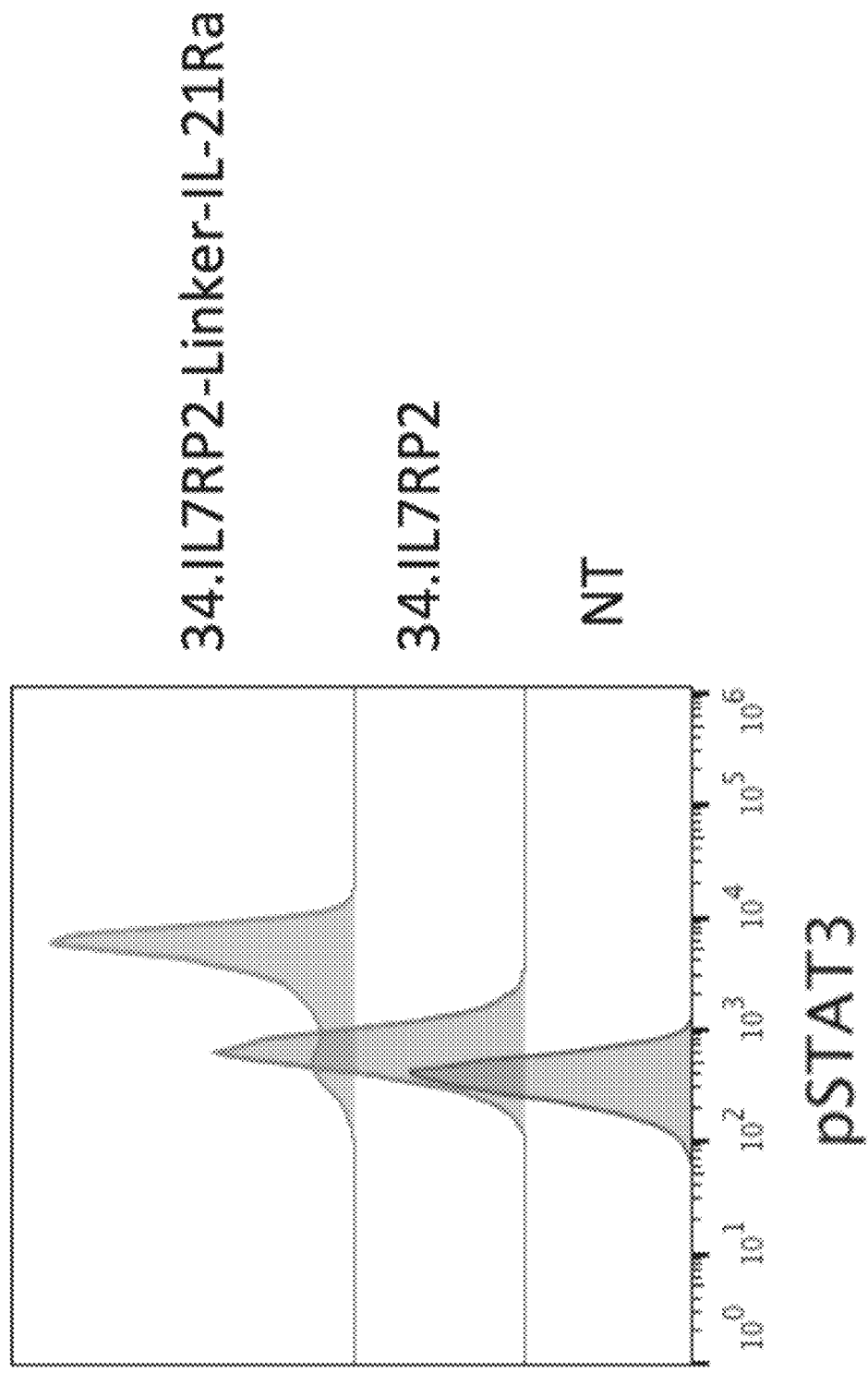

Combinatorial constitutively active cytokine receptors are encompassed in embodiments of the disclosure. For example, the Δ34.IL7RP2 protein can be fused with the IL-21Rα cytoplasmic domain to generate constitutively active combinatorial cytokine receptors. Δ34.IL7RP2 was fused at the C-terminus to the cytoplasmic domain of the IL-21 receptor, with a flexible linker in between the two cytoplasmic domains to avoid steric hindrance of STAT5 binding, to generate Δ34.IL7RP2-linker-IL21Rα (FIG. 10A). To evaluate STAT activation capacity, T-cells (NT, Δ34.IL7RP2 transduced T-cells, or Δ34.IL7RP2-linker-IL21Rα transduced T-cells) were rested for 24 hours without cytokines. Δ34.IL7RP2 and Δ34.IL7RP2-linker-IL21Rα T-cells were able to constitutively activate STAT5 (FIG. 10B), but only Δ34.IL7RP2-linker-IL21Rα demonstrated constitutive STAT3 activity (FIG. 10C). STAT3 is the key downstream signaling node activated by the IL-21 receptor.

Figure 11:
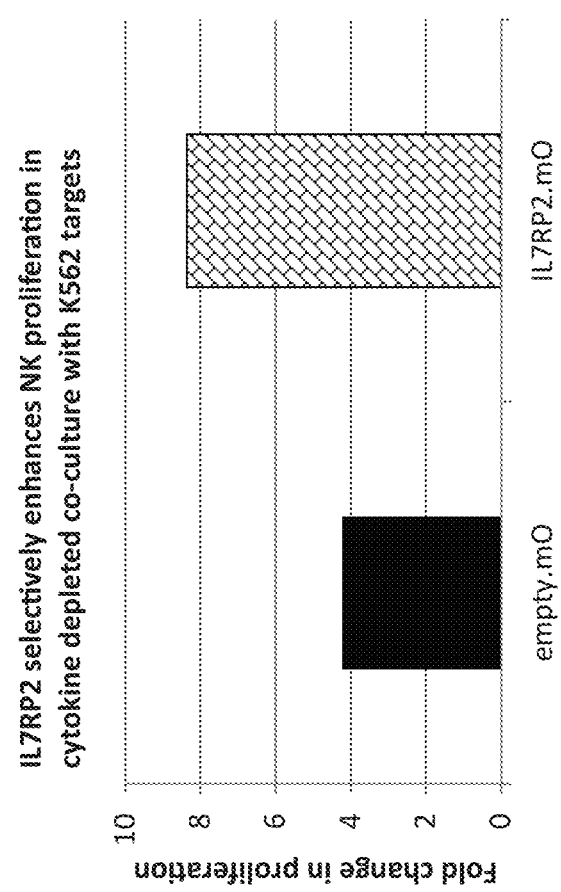
FIG. 11: IL7RP2 enhances antigen-mediated proliferation of NK cells.

Cells other than T-cells may be modified to express one or more constitutively active cytokine receptors. In FIG. 11, IL7RP2 enhances antigen-mediated proliferation of NK cells. NK cells were transduced with the IL7RP2-IRES-mOrange (IL7RP2.mO) vector or control vector IRES-mOrange (empty.mO) and then stimulated with irradiated K562 target cells in the absence of cytokines for 7 days. IL7RP2.mO NK cells demonstrated an 8-fold increase in fold proliferation while empty.mO NK cells only proliferated 4-fold.

Example 2

Particular Embodiments of Exodomains

Figure 12:
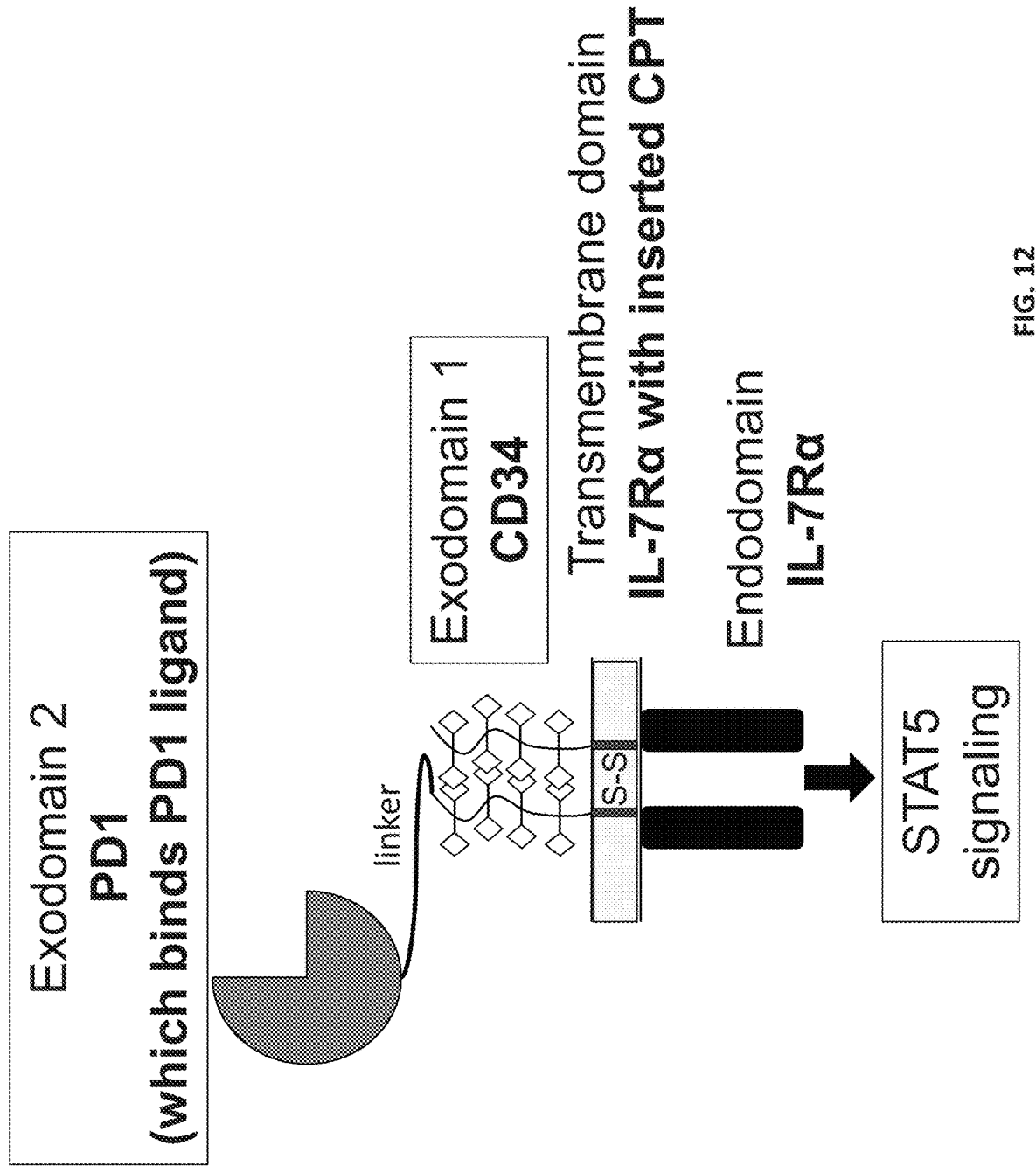
FIG. 12: Illustration of one embodiment wherein the constitutively active cytokine receptor is comprised of two exodomains.
Figure 13:
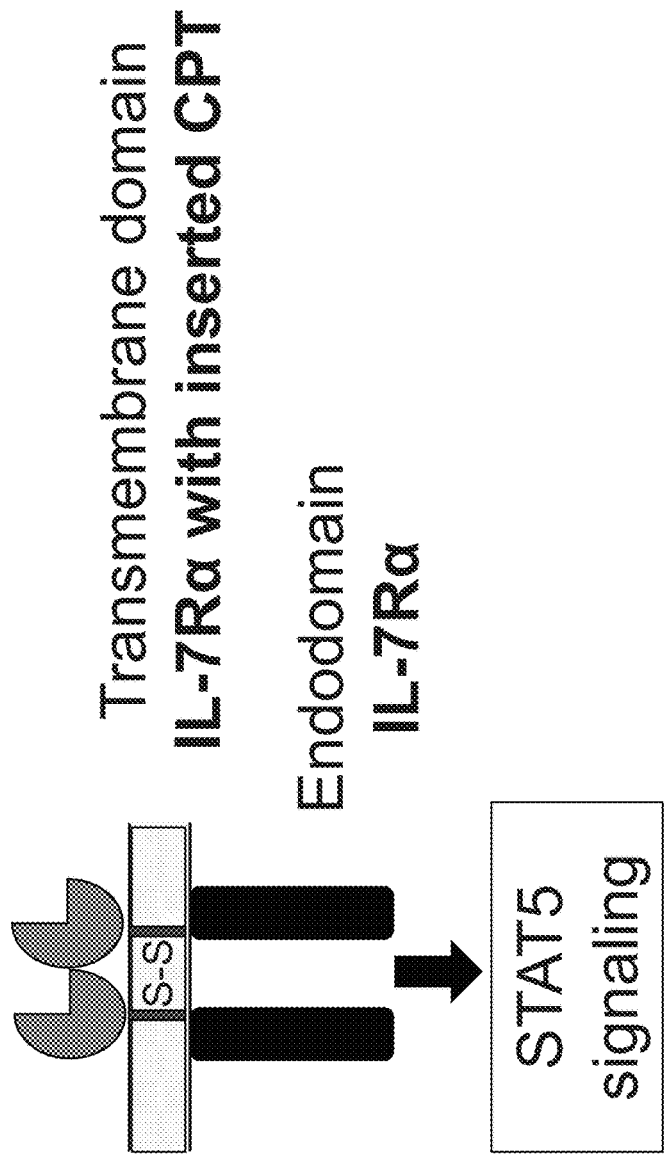
FIG. 13: Illustration of an embodiment wherein the constitutively active cytokine receptor utilizes an exodomain as a decoy receptor to bind harmful or potentially harmful ligands to the cell that expresses the receptor.

FIG. 12 illustrates a particular example wherein multiple exodomains are utilized in the constitutively active cytokine receptor. Therein, the PD1 exodomain is linked to the ΔCD34 exodomain of Δ34.IL7RP2, and this particular PD1 exodomain competes with normal PD1 for PDL1 binding (and thereby acting as a decoy receptor), which would decrease PD1 immuno-suppression. In some cases, the receptor utilizes such an exodomain as a single exodomain (FIG. 13). For a decoy receptor, the receptor may or may not include CD34 or a portion thereof. Other embodiments of exodomains for a decoy receptor include CTLA4.

Example 3

Constitutive Delivery of Cytokine Signaling to Lymphocytes Facilitates Enhanced Anti-Tumor Efficacy Adoptive lymphocyte therapy has shown success against leukemias and lymphomas but minimal efficacy against solid tumors. The challenges posed by solid tumors to tumor-specific T-cells may be understood by examining the 3 signal paradigm required for T-cell activation: Signal 1 (T-cell receptor activation by antigen), Signal 2 (co-stimulation), and Signal 3 (cytokine activation). These signals work together to expand adoptively transferred lymphocytes in-vivo and drive their elimination of tumors. Solid tumors prevent the 3-signal activation of T-cells by mechanisms such as down-regulation of MHCI molecules that present tumor antigens to T-cells, failure to express co-stimulatory ligands, and production of immunosuppressive cytokines. A solution has been to genetically modify T-cells to express chimeric antigen receptors (CARs), which provide Signals 1 and 2 upon MHCI-independent antigen ligation and some Signal 3 from IL-2 secretion. However, Signal 3 remains incompletely activated by this approach. This deficiency was corrected through overexpression of a genetic construct that constitutively delivers IL-7 cytokine signaling. In the absence of cytokine support, the cytokine-delivery strategy enhances antigen-dependent cytotoxicity, expansion, and persistence of CAR T-cells in-vitro. This was reproduced in-vivo with xenograft neuroblastoma and glioblastoma mouse models (as examples only), demonstrating significantly improved efficacy of Signal 3 supplemented adoptive immunotherapy against solid tumors.

Example 4

Constitutive Signaling from an Engineered IL-7 Receptor Promotes Durable Tumor Elimination by Tumor Redirected T-Cells

INTRODUCTION

Adoptive immunotherapy using T-cells modified with chimeric antigen receptors (CARs) has achieved remarkable clinical efficacy against refractory leukemia and lymphoma but challenges remain in translating these successes to solid tumors. Substantial expansion and persistence of adoptively transferred T-cells are necessary for durable antitumor efficacy. Of the 3 signals required for optimal T-cell activation and expansion, CAR activation can recapitulate Signal 1 (T-cell receptor (TCR) activation) and Signal 2 (co-stimulation) but cannot sustain a positive Signal 3 derived from immunostimulatory cytokines that are scarce in tumor microenvironments. In xenograft tumor models, Signal 3 has been supplemented with injections of cytokines such as IL-2 to augment anti-tumor activity, without notable adverse effects. However, systemic administration of cytokines to cancer patients has caused significant toxicity. Alternative approaches such as genetic modification of T-cells to secrete or trans-present cytokines carry a risk of severe adverse events including neurotoxicity and cytokine release syndrome from systemic accumulation of secreted cytokine, while T cells that overexpress cytokine receptors do not eliminate the need for exogenous cytokine.

The present example provides a strategy to selectively provide Signal 3 to T-cells with a constitutively active IL-7 cytokine receptor (C7R), avoiding the above-mentioned problems. This novel chimeric receptor provides signal 3 without the requirement for exogenous agents or the non-specific bystander T-cell activation caused by forced expression of transgenic cytokines. The growth and survival of C7R-expressing CAR T-cells remains antigen dependent, but in the presence of tumor, these cells have superior anti-tumor activity in multiple model systems.

C7R Constitutively Activates STAT5 and is Engineered to be Unresponsive to Extracellular Ligand In this Example, IL-7 was the focus of attention, because the cytokine bolsters the persistence of tumor-specific T-cells. IL-7 receptors bearing certain mutations result in gain of function due to cysteine and/or proline insertions in the transmembrane domain, causing IL-7Rα homodimerization. Once the homodimer is formed, cross-phosphorylation of JAK1/JAKI activates STAT5, a core signaling node downstream of IL-7.

Figure 14D:
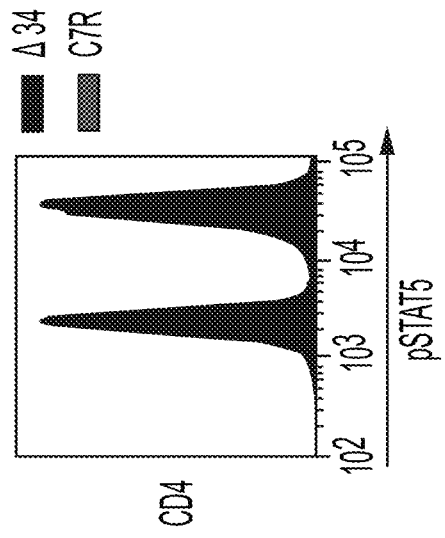
Figure 14E:
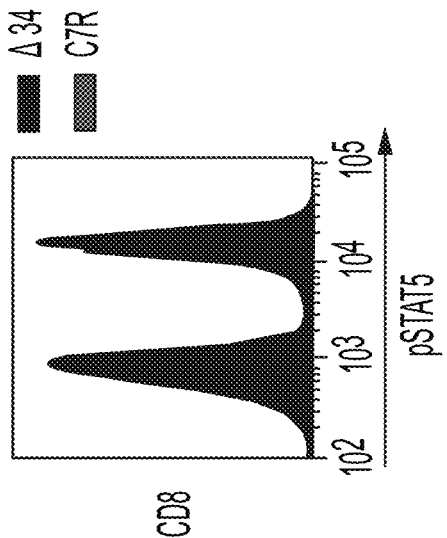

To discover whether this class of receptors could produce a consistent Signal 3 to complete the three-signal requirement for optimal CAR T-cell activity, a constitutively active IL-7 receptor variant (IL7R*) that has significant STAT5 activation was selected. To avoid additional activation of the receptor by external ligand and provide a means of detecting transduced cells, the native extracellular domain of the receptor was replaced with ectodomains derived from CD34. To learn whether ectodomain size factored into the efficiency of protein expression and function ectodomains from Q8 (65 amino acids) and CD34 (259 amino acids) were used. The Q8 ectodomain comprises a CD34 epitope mounted on top of a CD8 spacer, allowing detection by the anti-CD34 antibody clone QBEND10. Retroviral-mediated expression of the CD34-IL7R* and Q8-IL7R* constructs in healthy donor T-cells revealed poor expression of the Q8-IL7R* fusion protein and suboptimal STAT5 activation (FIG. 18). In contrast, CD34-IL7R* was robustly expressed in T-cells and was functionally active. Therefore CD34-IL7R* was used, henceforth referred to as C7R (but also referred to herein as Δ34.IL7RP2), for all subsequent studies (FIG. 14A).

Figure 14B:
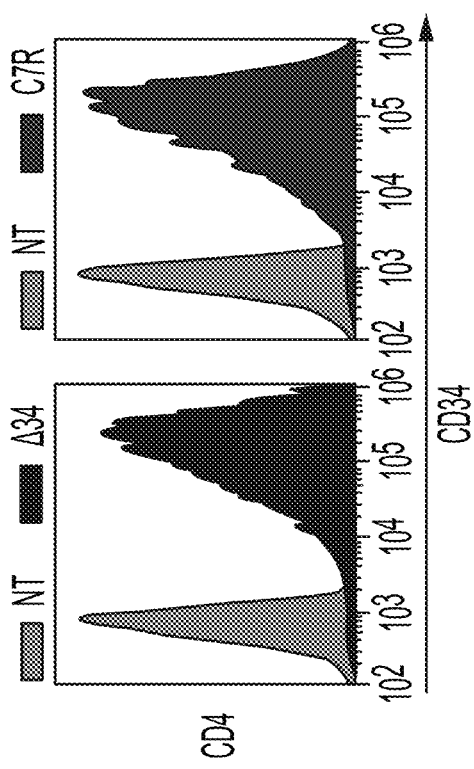
Figure 14C:
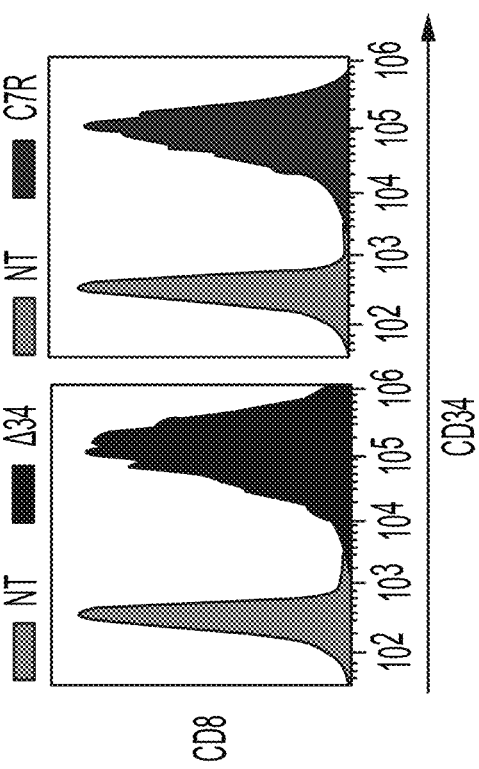
Figure 14F:
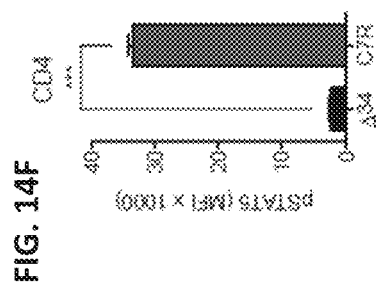
Figure 14G:
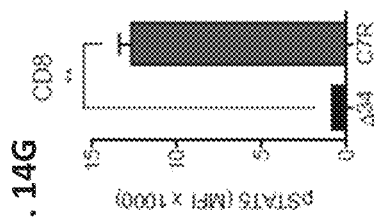
Figure 14H:
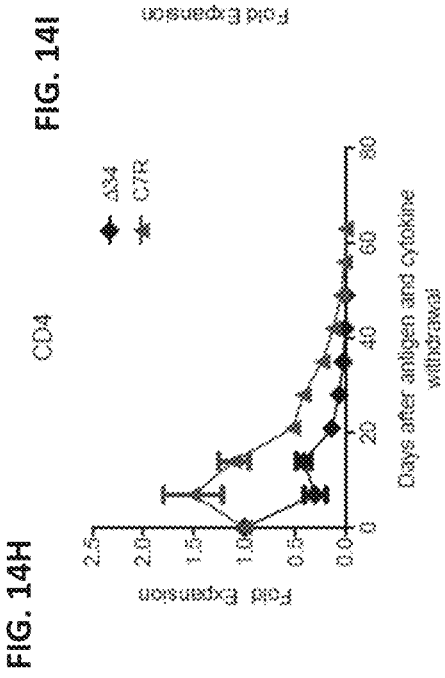
Figure 14I:
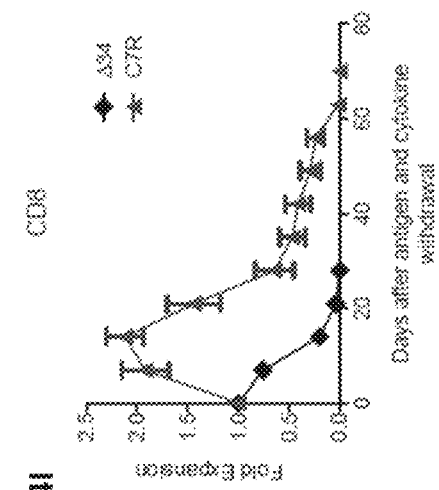

To determine the relative effects of C7R in CD4 and CD8 T-cells, the two subpopulations were separated using antibody coated magnetic beads, activated and transduced them, and cultured the T-cell subsets separately from each other. C7R was readily expressed by both CD4 and CD8 T-cells (FIGS. 14B,14C and FIG. 19), and produced greater constitutive activation of STAT5 in T-cells than a control construct consisting of a truncated CD34 (Δ34) molecule (Quintarelli, 2007) (FIGS. 14D-14G). Importantly, C7R did not promote antigen-independent expansion of CD4 and CD8 Tcells in vitro (FIGS. 14H,14I). While C7R transduced cells persisted significantly longer in antigen and cytokine depleted conditions than control cells in vitro, the C7R population began to contract by 14-21 days, with all cells dying by day 70 after initiation of the persistence assay. This confirmed that C7R, alone, does not sustain autonomous T-cell expansion, an important property for CAR T-cell safety.

Figure 15B:
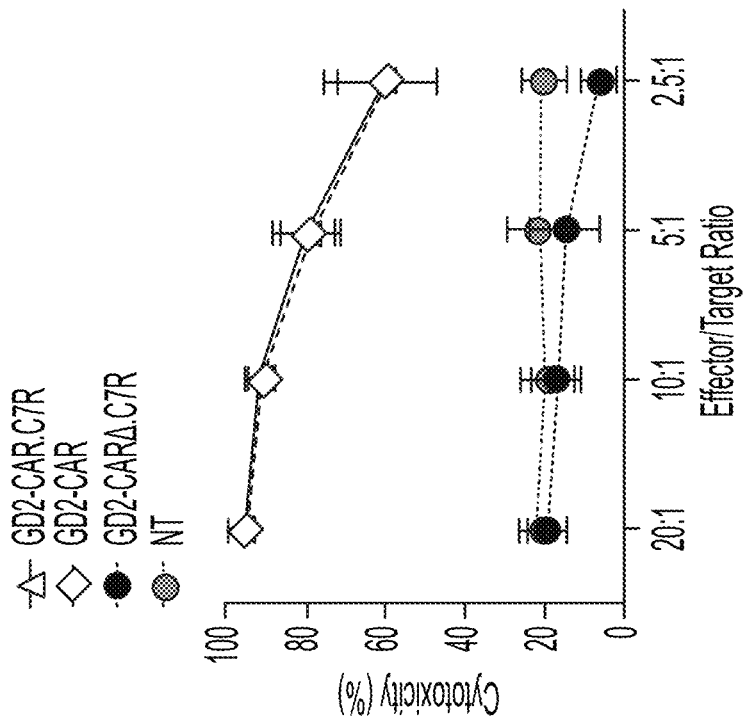
FIGS. 15A-15I: C7R enhances GD2-CAR T-cell activity during serial tumor to document, challenge. (15 A) Cytokines secreted by GD2-CAR T-cells or GD2-CAR.C7R T-cells 24 hours after co-culture with LAN-1 tumor cells was determined by ELISA. (15B) 4-hour luciferase based cytotoxicity assay of T-cells killing LAN-1 tumor cells. (15C) Serial co-culture schematic. The first co-culture (CC1) was initiated with 1×106 GD2-CAR or GD2-CAR.C7R T-cells together with 0.5×106 LAN-1 GFP-FFluc tumor cells for 7 days, in the absence of TL-15 or IL-7. For the second and third co-cultures (CC2 and CC3), T-cells were harvested from the previous co-culture and then replated in new culture medium with fresh tumor cells at the same 2:1 E:T ratio. (15D) Cumulative expansion of GD2-CAR or GD2-CAR.C7R T-cells during serial co-culture. Arrows indicate timepoints of T-cell re-stimulation with tumor cells. (15E) LAN-1 tumor cells remaining after CC3 with GD2-CAR T-cells and GD2-CAR.C7R T-cells, respectively. (15F, 15G) For proliferation analysis, GD2-CAR and GD2-CAR.C7R T-cells collected at the end of CC1 were labeled with CELL TRACE® (cell monitoring system to trace multiple cell generations) Violet before being rechallenged during CC2. (15F) Histogram overlay represents data from a representative donor. (15G) The experiment in F was repeated with multiple donors and the division indices compiled from the GD2-CAR and GD2-CAR.C7R proliferation histograms. (15H) For survival analysis, GD2-CAR and GD2-CAR.C7R T-cells were stained with Annexin V and 7-AAD after 2 serial tumor challenges with LAN-1 tumor cells. Bar graphs show the frequencies of T-cells staining positive for Annexin V, 7-AAD, both, or neither. The Annexin V(+)7-AAD(−) and Annexin V(−)7-AAD(+) mean comparisons were n.s. (151) After the end of CC2, tumors were labeled with GD2-specific antibody and magnetically separated from the CAR T-cells. Total RNA was isolated from T-cells and gene expression analysis was subsequently performed using the Human Immunology Panel Version 2 and nCounter Analysis System (Nanostring). The displayed heat map shows genes with log 2 fold changes (GD2-CAR.C7R/GD2-CAR) that had P values less than 0.02. Data was generated from 5 donors (10 paired samples). *P<0.05, **P<0.01, (two-tailed paired t-test, 15 A, 15B, 15D, 15E, 15G, 15H). Graphs 15 A, 15B, 15C, 15E, 15G, 15H represent averages from different donors SEM (n=6, 15 A, 15D, 15E; n=3, 15G, 15H).
Figure 15A:
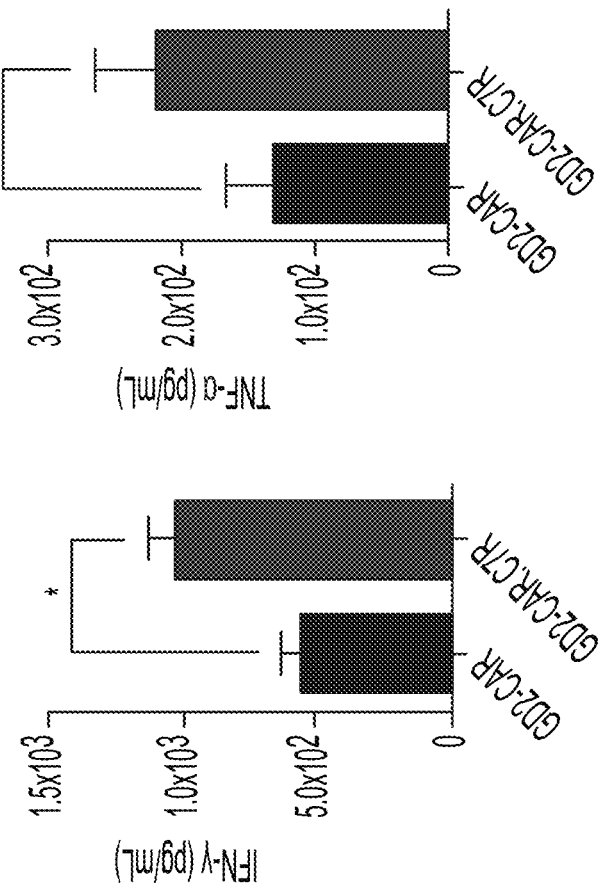
Figure 15C:
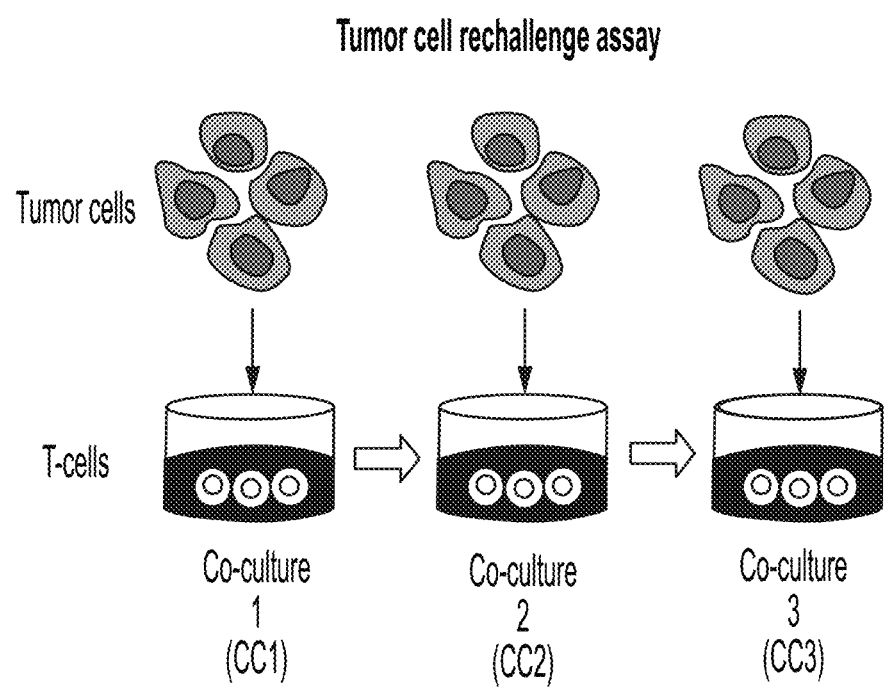
Figure 15F:
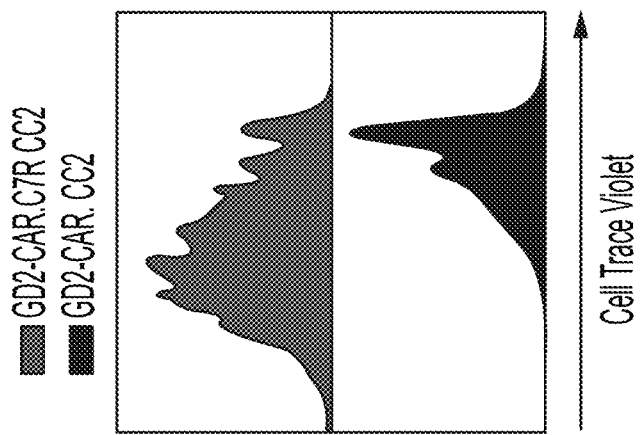
Figure 15E:
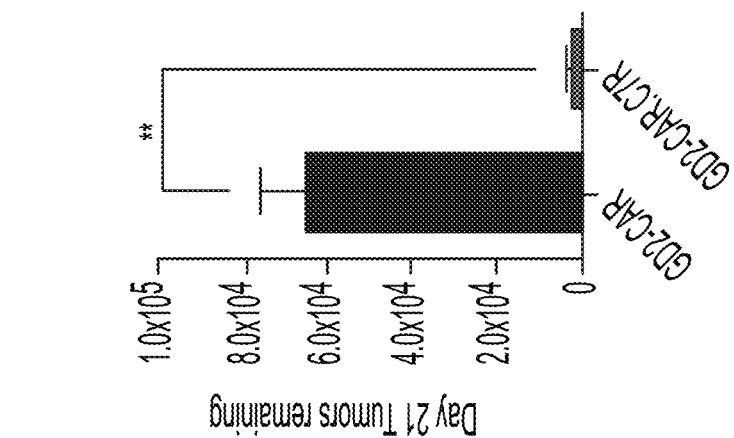
Figure 15D:
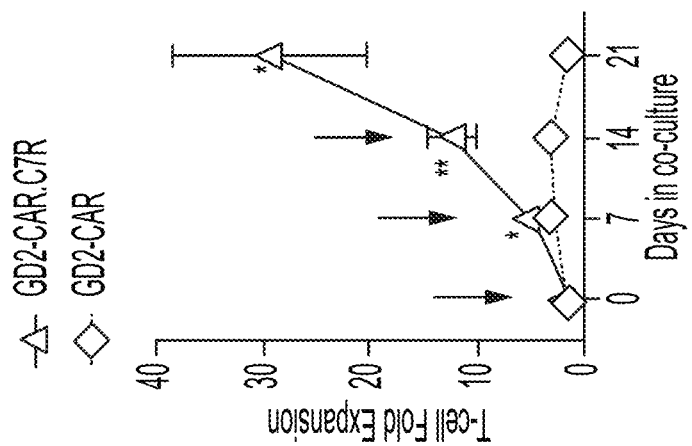
Figure 15H:
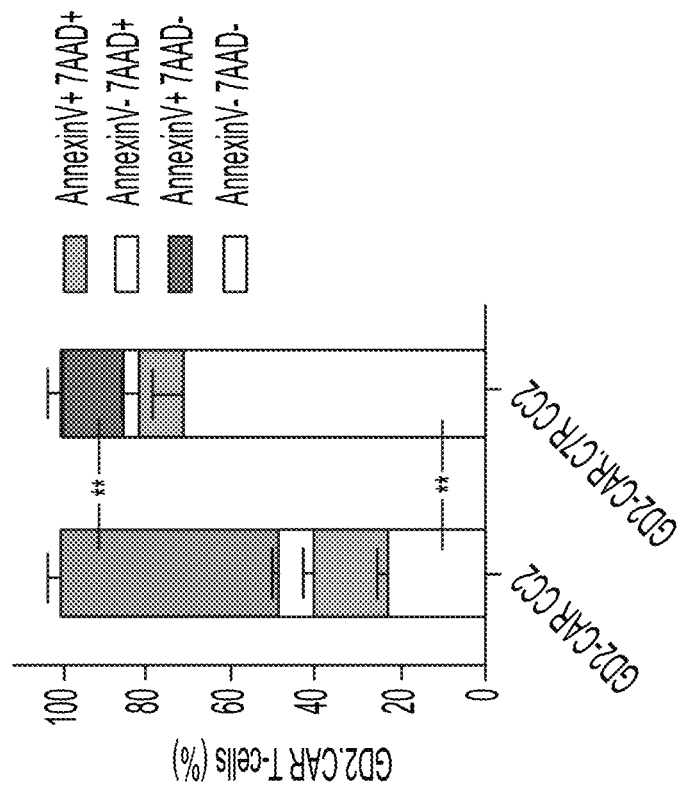
Figure 15G:
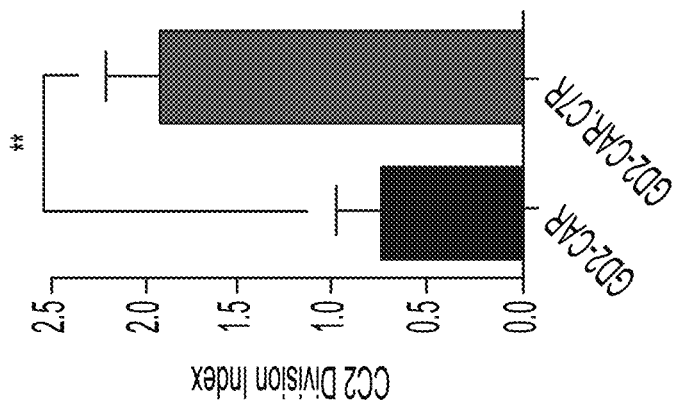
Figure 15I:
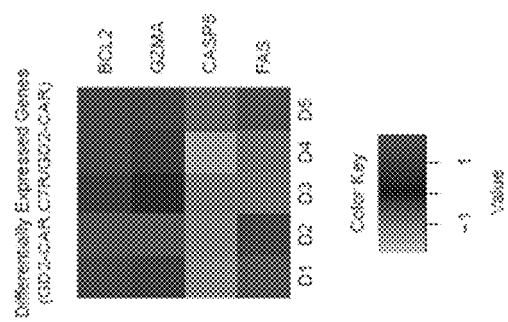
Figure 16A:
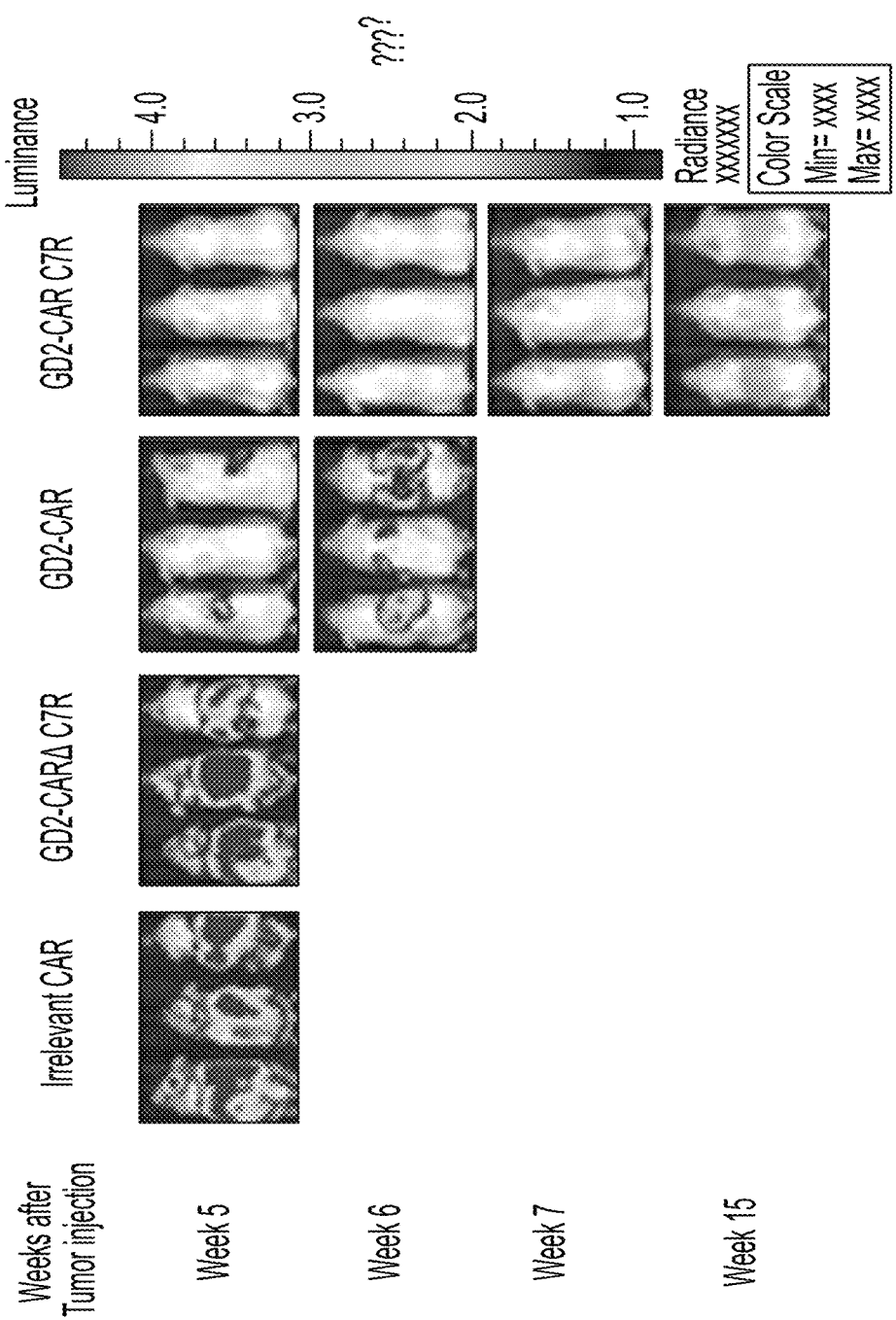
FIGS. 16A-16F: C7R enhances adoptive T-cell immunotherapy against metastatic and intracranial malignancies. (16A) and (16B) 1×10$^6$ CHLA-255 FFluc cells were injected i.v. into female NSG mice, followed 7 days later by 1×10⁶ T-cells expressing an irrelevant CAR, GD2-CARΔ.C7R, GD2-CAR, or GD2-CAR.C7R. (16A) Representative bioluminescent images of neuroblastoma growth over time. (16B) Kaplan Meier survival analysis of CHLA-255 FFluc challenged mice. (16C, 16D) To track T-cell migration and persistence, in a parallel experiment, 1×10⁶ CHLA-255 cells were injected intravenously into NSG mice, followed 7 days later by 1×10⁶ GFP-FFluc T-cells co-expressing GD2-CAR or GD2-CAR.C7R. (16C) Sequential bioluminescent imaging of T-cells (16D) Quantitated bioluminescent signal of T-cells over time (16E) 1×10⁵ U373 GFP-FFluc cells were injected intracranially into male SCID mice. 7 days later, 1×10⁴ T-cells expressing EphA2-CARΔ.C7R, EphA2-CAR, or EphA2-CAR.C7R were intracranially injected into the tumor. Quantitated U373 GFP-FFluc bioluminescence from each treatment group is displayed over time. (16F) Kaplan Meier survival analysis of U373 GFP-FFluc challenged mice after treatment with T-cells. *P<0.05, **P<0.01 (Welch's t-test, D; paired two-tailed t-test.
Figure 16B:
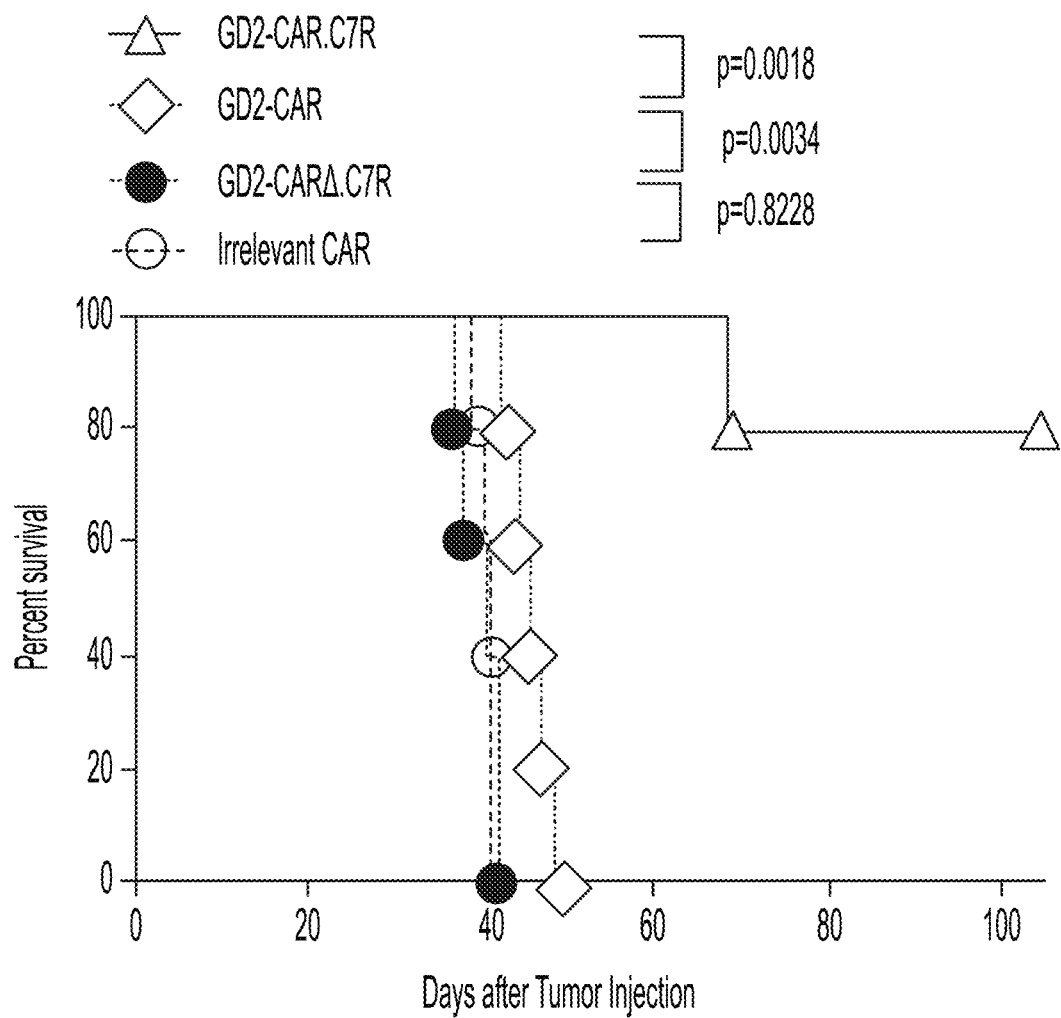
Figure 16C:
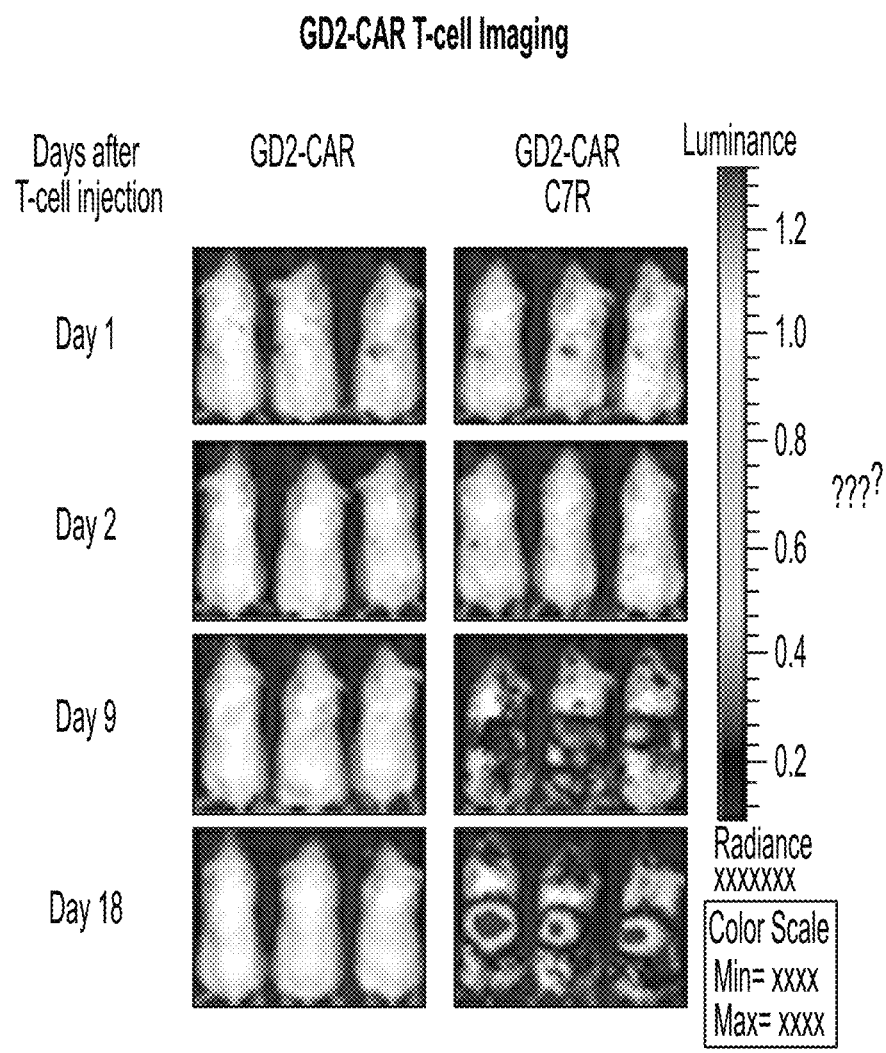
Figure 16D:
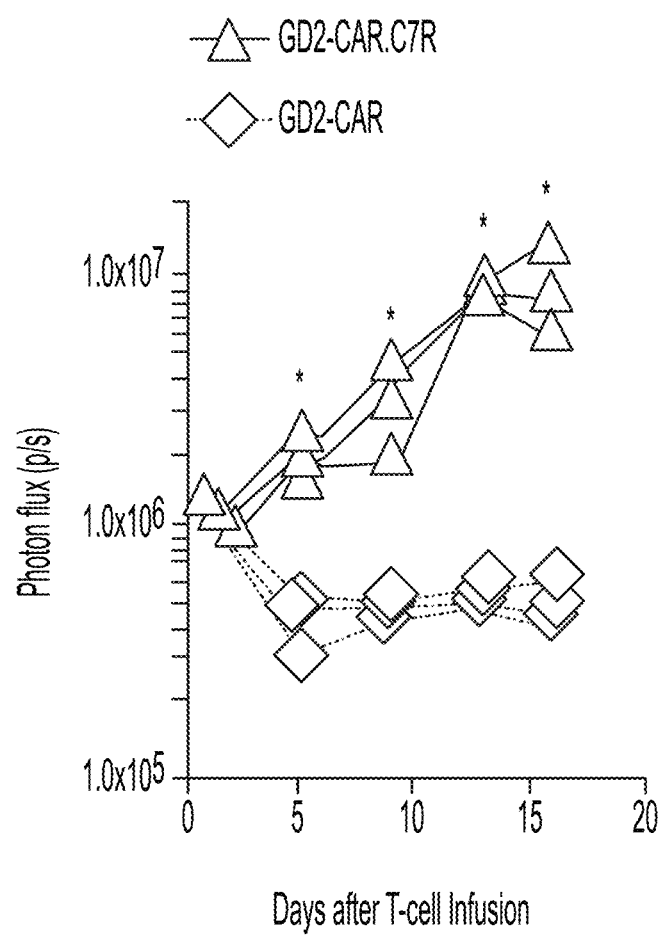
Figure 20A:
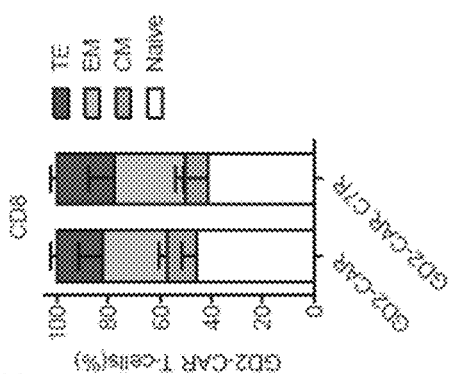
FIGS. 20A-20D: C7R signaling does not change phenotypic composition of GD2-CAR T-cells during culture. (20A) Scheme of the GD2-CAR and GD2-CAR.C7R vectors. The GD2-CAR construct is composed of a 14g2a scFv, a CD8 extracellular spacer, a CD8 transmembrane domain, and 41BBξ endodomain, followed by IRES and a truncated NGFR. The GD2-CAR.C7R construct is identical except that the IRES and truncated NGFR are replaced with a 2A sequence followed by C7R. (20B, 20C) The memory phenotype of T-cells expressing GD2-CAR or GD2-CAR.C7R was compared. Bar graphs show relative frequencies of (20B) CD4 T-cells and (20C) CD8 T-cells that were CD45RO−CCR7−(Terminal Effector-like, TE), CD45RO+CCR7−(Effector Memory, EM), CD45RO+CCR7+(Central Memory, CM), or CD45RO−CCR7+(Naïve). Differences between GD2-CAR and GD2-CAR.C7R were n.s. for all four memory subpopulations in both CD4 and CD8 T-cells. (20D) The CD4 and CD8 percentages were compared between GD2-CAR and GD2-CAR.C7R T-cells. Differences were n.s. Graphs 20B-20D represent averages ±SEM (n=3) and populations were compared using the two-tailed t-test.
Figure 20B:
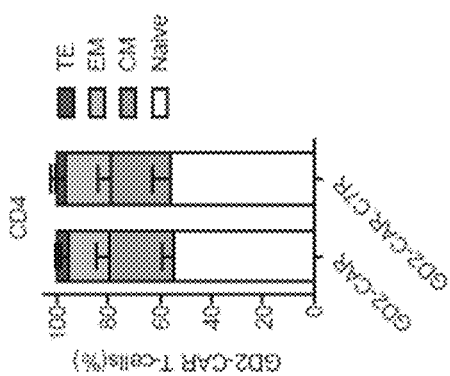
Figure 20C:
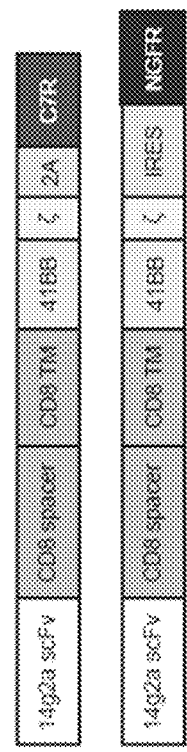
Figure 20D:
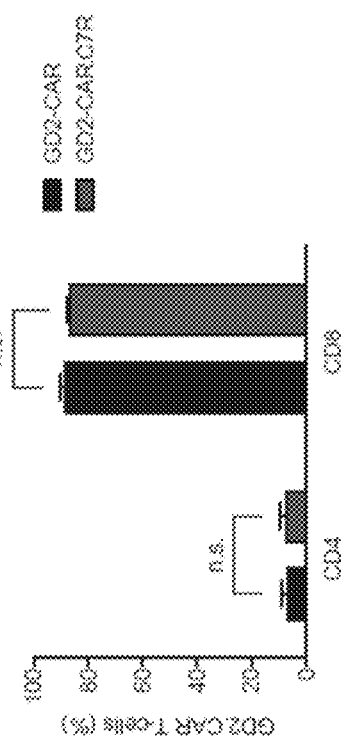

C7R Promotes Survival in GD2-CAR T-Cells During Serial In Vitro Tumor Cell Challenges To evaluate whether C7R could increase anti-tumor efficacy of CAR T-cells, we treated GD2+ neuroblastoma cells were separated with T-cells expressing a GD2-CAR comprising a 14g2a scFv linked to a CD8a stalk and transmembrane domain, and a 41BB.ξ signaling 7/3/2202 endodomain (FIG. 20A). 14g2a-based GD2-CAR T-cells have shown a safe profile in clinical trials treating neuroblastoma patients, and while complete remissions haven been achieved in select patients, higher efficacy remains desirable. In comparing T-cells expressing either the GD2-CAR alone or a bicistronic construct containing the GD2-CAR and C7R (GD2-CAR.C7R), C7R did not induce significant differences in the memory subset composition or the CD4/CD8 percentages of GD2-CAR T-cells (FIGS. 16B-16D). While C7R increased secretion of IFN-γ and T F-a in GD2-CAR T-cells after stimulation with LAN-1 tumors (FIG. 15 A), this was not associated with any increase in the potency of T-cell killing during a 4-hour cytotoxicity assay (FIG. 15B). However, GD2-CAR.C7R T-cells significantly outperformed GD2-CAR T-cells when their ability was measured to maintain cytotoxicity and expansion after repeated challenges with tumors during in vitro sequential co-culture killing assays (FIG. 15C). GD2-CAR T-cells failed by the third challenge, losing both their ability to expand and eliminate tumor cells (FIGS. 15D, 15E). In contrast, GD2-CAR T-cells expressing C7R responded to all 3 sequential tumor challenges. To determine the relative contributions of increased proliferation versus reduced apoptosis to the improved cell expansion of GD2-CAR.C7R T-cells, CELL TRACE® (cell monitoring system to trace multiple cell generations) Violet labeling was used after the first co-culture. Upon subsequent re-stimulation with tumor cells, GD2-CAR.C7R T-cells showed greater cell division than T-cells expressing only the GD2-CAR (FIGS. 15F,15G). To assess whether C7R also reduced T-cell apoptosis, Annexin V and 7-AAD staining were used following the second tumor restimulation. Flow cytometric analyses showed larger populations of Annexin V(+)/7-AAD(+) GD2-CAR T-cells compared to GD2-CAR.C7R T-cells (FIG. 15H), demonstrating increased viability generated by C7R despite sequential tumor challenges. To further understand the molecular basis for these results, Nanostring technology was used to perform gene expression analysis of GD2-CAR and GD2-CAR.C7R Tcells after the second tumor restimulation (FIG. 15I and FIG. 22). BCL2, which mediates the anti-apoptotic effects of IL-7, was one of the top genes upregulated by C7R in GD2-CAR T-cells. There was upregulation of cytolytic granzyme A (GZMA) and downregulation of pro-apoptotic FAS and caspase 8 (CASP8), which are involved in cellular apoptosis and activation induced cell death (AICD) (Krammer, 2007). Therefore, C7R augments both proliferation and survival of GD2-CAR T-cells to enhance their performance during sequential encounters with tumor cells.

C7R Co-Expression in CAR T-Cells Enhances their Anti-Tumor Activity Against Xenograft Tumor Models The ability of C7R-enhanced GD2-CAR T-cells to eradicate metastatic neuroblastoma in a xenograft model was tested. Neuroblastoma cells were engrafted in nonobese diabetic (NOD) severe/combined immunodeficient (SCID) IL-2rγ–/– (NSG) mice by intravenous injection of the multidrug-resistant, MYC-N non-amplified neuroblastoma cell line CHLA-255 modified to express firefly luciferase (CHLA-255 FFluc) (Heczey, 2014, Blood. 2014 Oct. 30; 124(18):2824-33). Treatment with a low dose of GD2-CAR T-cells one week after tumor engraftment increased median survival by one week, compared to control mice treated with T-cells expressing an irrelevant CAR. Mice receiving T cells expressing C7R and a nonfunctional GD2-CAR with a truncated endodomain (GD2-CARΔ.C7R) had identical survival to the control mice. (FIGS. 16A,16B). In contrast, disease was eliminated in mice infused with GD2-CAR.C7R T-cells. In a parallel experiment in which T-cells rather than CHLA-255 cells were GFP-FFluc transduced, there was no expansion of GD2-CAR T-cells with the limited dose that were infused but robust expansion of GD2-CAR.C7R T-cells was seen with accumulation of T-cell signal in the liver, a site of extensive neuroblastoma metastasis (FIGS. 16C,16D). These results demonstrated that GD2-CAR T-cells could not persist against tumors in vivo whereas GD2-CAR T-cells expressing C7R could proliferate and survive to mediate metastatic tumor clearance.

Figure 16E:
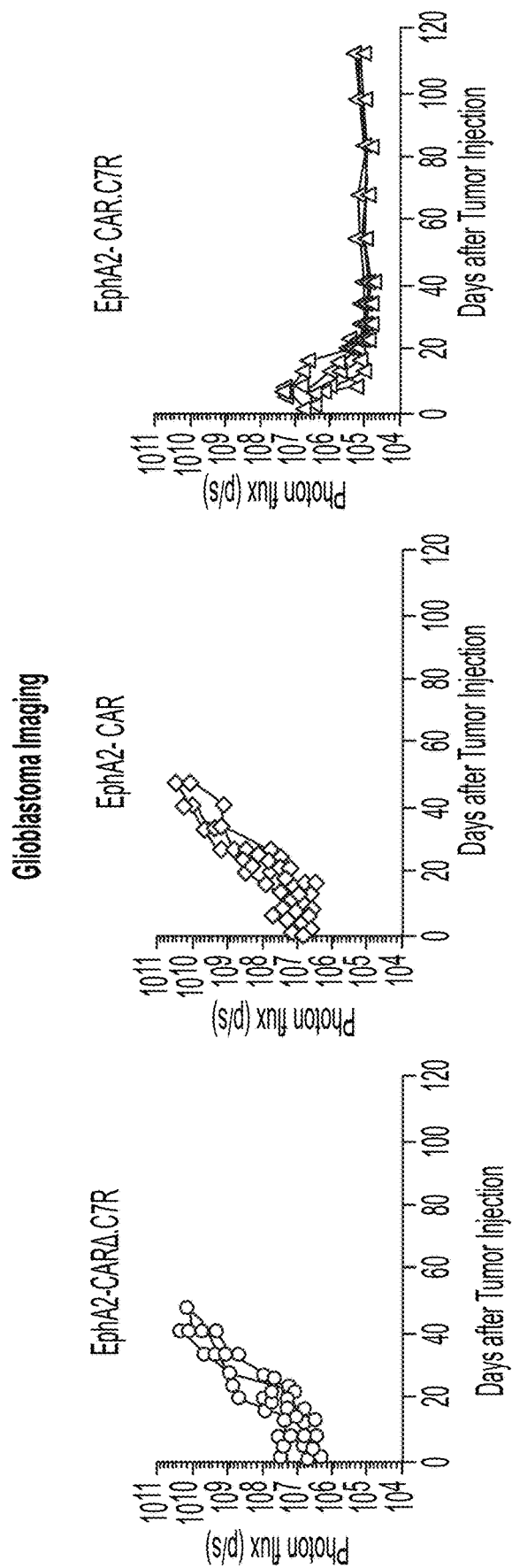
Figure 16F:
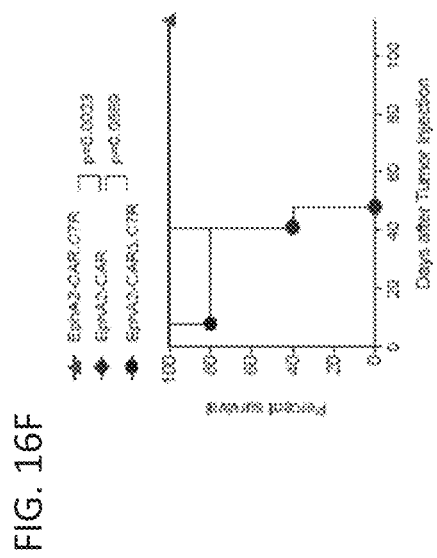
Figure 18A:
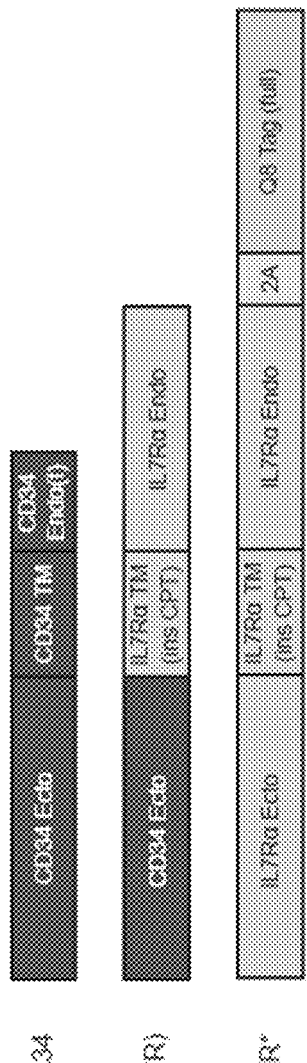
FIGS. 18A-18D: CD34-IL7R* (C7R) is stably expressed in T-cells and enhances constitutive STAT5 activation relative to IL7R*. (18A) Schematics of IL7R* fusion constructs and Δ34. All IL7R* constructs contain a modified IL-7Rα transmembrane domain (insertion of cysteine, proline, and threonine between Thr244 and Ile245 in IL-7Rα) and the unmodified IL-7Rα endodomain. The Δ34 construct contains the ectodomain and transmembrane of CD34 but retains only a portion of the endodomain. (18B) Transduced cells were stained with an anti-CD34 antibody specific for QBEND10 (which detects the CD34 epitope used in Q8) to compare transduction efficiency of the constructs in a, relative to NT cells. Due to background expression of IL-7Rα on cultured NT cells, IL7R* transduction was indirectly detected by the Q8 tag in the bicistronic vector. Differences in transduction efficiency were n.s. when comparing Δ34 to IL7R* (p=0.2951) and when comparing IL7R* to C7R (p=0.1736). (18C) The MFI of the different constructs were compared from B. MFI comparison of Δ34 and IL7R*, as well as between Δ34 and C7R, were n.s. (18D) Comparison of STAT5 phosphorylation by T-cells. Cells were cultured without IL-15 and IL-7 for 24-72 hours before analysis. *P<0.05, P<0.01, *P<0.001, ****P<0.0001 (two-tailed t-test, 18B-18D). Graphs 18B-18D represent averages from different donors (n=3) ±SEM.
Figure 18D:
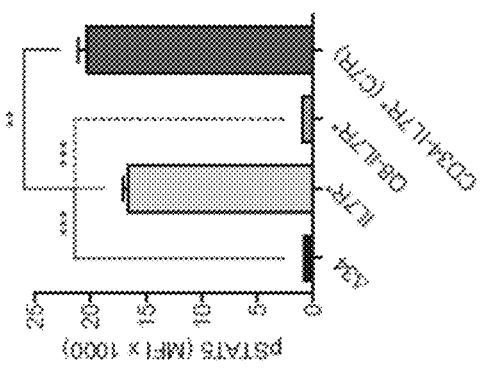
Figure 18C:
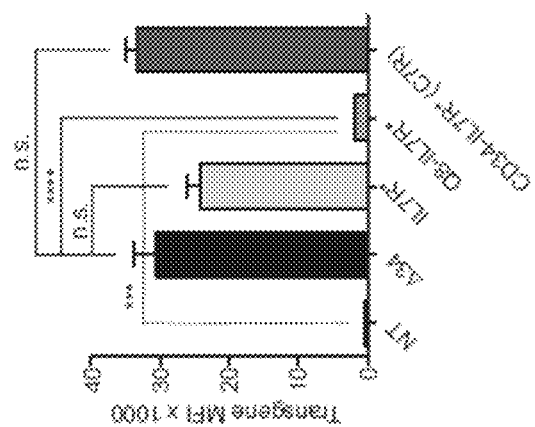
Figure 18B:
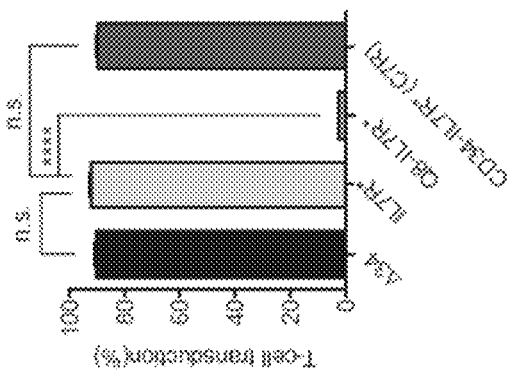

To investigate whether C7R could augment the performance of other CAR T-cells, the molecule was co-expressed with an EphA2-CAR intended to treat glioblastoma. U373 glioblastoma cells genetically modified with GFP-FFluc were injected intracranially into SCID mice. Seven days later, $10^4$ EphA2-CAR T-cells were administered intratumorally, a cell dose at which gliomas could not be eradicated based on previous experience. Glioblastoma bioluminescence increased rapidly in mice treated with control T-cells co-expressing C7R and a non-functional EphA2-CAR (EphaA2-CARΔ.C7R) and no significant improvement in anti-tumor control was seen in mice receiving EphA2-CAR T-cells (FIGS. 16E,16F). In contrast, tumors were completely eliminated in mice infused with the low "stress" dose of EphA2-CAR T-cells when they co-expressed C7R (EphA2-CAR.C7R) and these mice remained disease-free at the conclusion of the experiment. When the experiment was repeated using EphA2-CAR T-cells transduced also with GFPFFluc, bioluminescent signal from T-cells expressing the CAR alone had largely dissipated 4-6 days after infusion. In comparison, while EphA2-CAR.C7R T-cells lacked the significantly greater expansion observed in the (extracranial) neuroblastoma models, there was a trend towards greater T-cell persistence as determined by area under the curve (AUC) comparison between EphA2-CAR and EphA2-CAR.C7R T-cells (FIG. 21).

GD2-CAR.C7R T-Cells can be Efficiently Deleted Using iC9 after Tumor Clearance

As an additional safety measure, however, T-cells were generated that co-express a clinically validated inducible caspase9 (iC9) suicide gene (Di Stasi, et al., 2011) that can electively eliminate T-cells. After double transduction with iC9 and GD2-CAR.C7R, T-cells remained sensitive to iC9 signaling and underwent apoptosis in vitro within 24 hours of exposure to the chemical inducer of dimerization AP20187 (CID) (FIG. 17A). It was considered if iC9 could efficiently remove GD2-CAR.C7R T-cells in vivo after tumor regression. In order to evaluate T-cell activity and tumor growth simultaneously, a subcutaneous LAN-1 neuroblastoma model was used. Tumor cells were injected in the left dorsal flanks of NSG mice and 8 days later $1 \times 10_6$ GD2-CAR.C7R T-cells alone or doubly transduced with iC9 were intravenously injected. Control mice received GD2-CARΔ.C7R T-cells. All T-cells were co-transduced with GFP-FFluc for in vivo visualization. After 3 weeks, LAN-1 tumors outgrew in control mice, which were euthanized. T-cells co-expressing the GD2-CAR.C7R T-cells and iC9 vectors demonstrated similar anti-tumor efficacy and in vivo expansion as GD2-CAR.C7R T-cells alone (FIGS. 17B, 17C). To model T-cell deletion required to control toxicity after immunotherapy, 3 doses of CID were administered to mice beginning at 28 days after T-cell infusion within the same experimental approach. There was a loss of T-cell bioluminescence signal (mean 93%) immediately after CID administration (FIG. 17D) and the signal remained at baseline two weeks later without tumor recurrence, at which time the experiment was terminated. These results confirmed that CAR T-cells co-expressing C7R could be used together with iC9 if needed, without detriment to efficacy and permitting elective T-cell deletion.

Figure 23A:
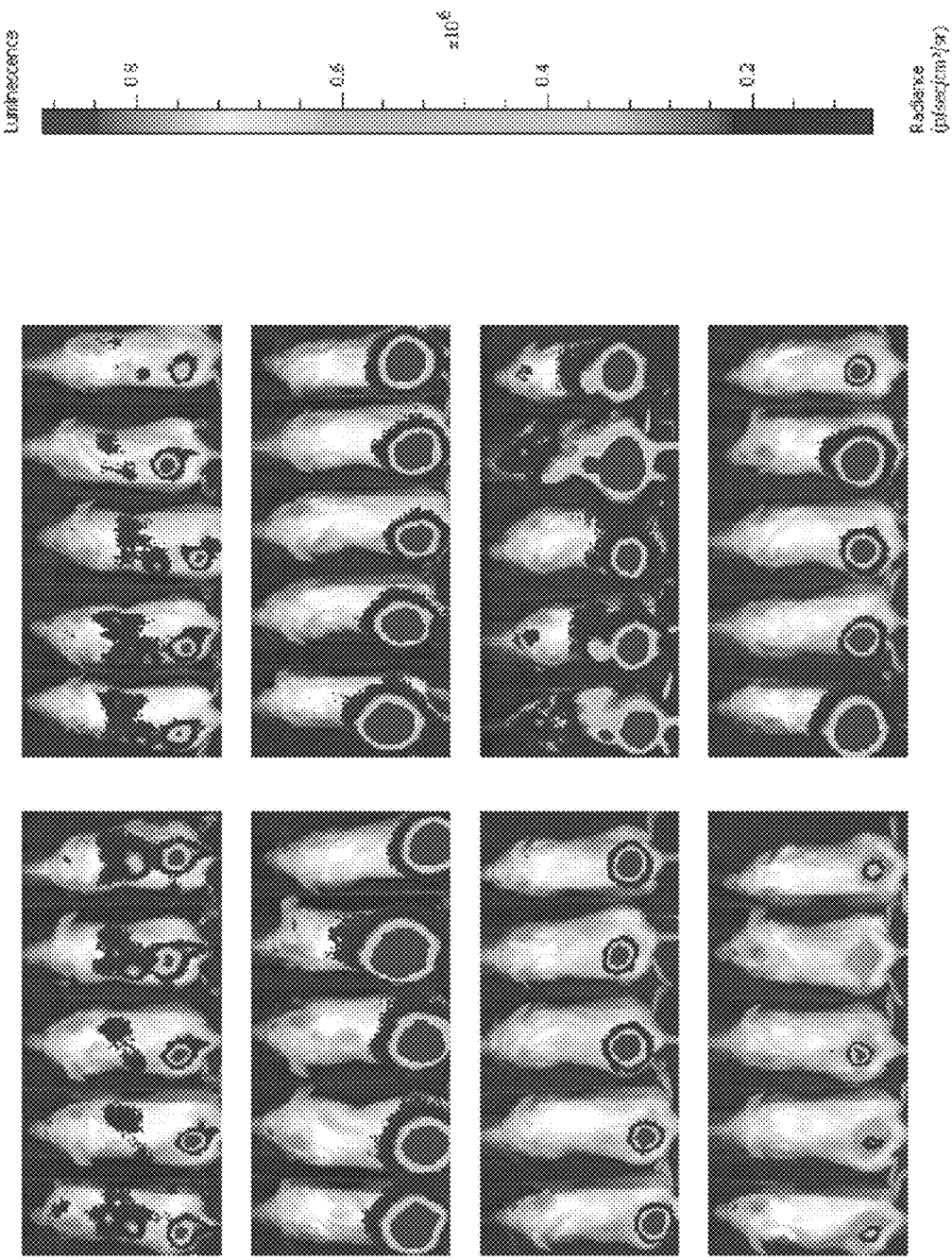
FIGS. 23A-23B: Treatment of LCL tumors with 34.IL7RP2-EBVSTs.
Figure 23B:
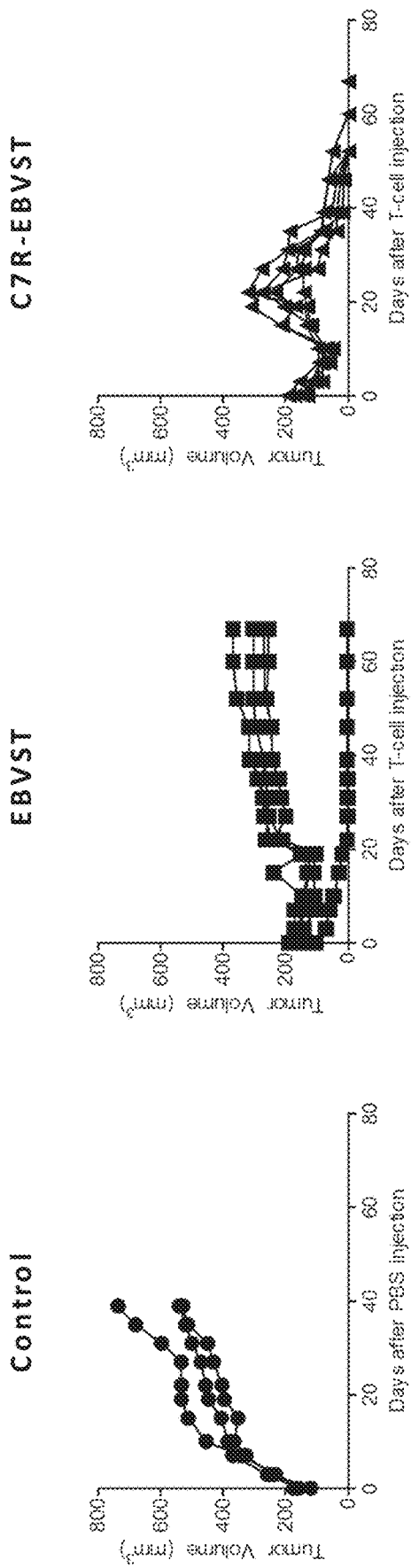

Treatment of LCL tumors with 34.IL7RP2-transduced EBV-specific T-cells shows anti-tumor efficacy. LCL tumors were injected subcutaneously into the dorsal left flanks of female NSG mice. 8 days later, $5 \times 10^6$ EBV-specific T-cells (EBVST)s or 34.IL7RP2-transduced EBVSTs (34.IL7RP2-EBVST)s, co-expressing GFP-firefly-luciferase (GFP-Ffluc) were injected intravenously. PBS was injected into tumor bearing mice as a control. In FIG. 23A, imaging of the luciferase signal in mice reveals that 34.IL7RP2-EBVSTs have prolonged persistence at the tumor site relative to EBVSTs alone. Likewise, in FIG. 23B, measurement of tumor growth shows that 34.IL7RP2 EBVSTs have superior anti-tumor efficacy relative to EBVSTs alone.

Significance of Certain Embodiments

The results demonstrate Signal 3 in T-cell activation significantly improves sustaining the activity of CAR T-cells against solid tumors, and that constitutively active IL-7 receptors can be used to provide Signal 3 for the enhancement of adoptive immunotherapy. Under the stress of repeated antigen exposure that T-cells will likely encounter within solid malignancies, only GD2-CAR T-cells co-expressing C7R were able to undergo multiple rounds of expansion and retain anti-tumor activity. The superiority of C7R-enhanced CAR T-cells was shown for two different CAR and tumor models in vivo in which functional CAR T-cells administered at ineffective doses could, if combined with C7R, sustain the ability to eradicate established tumors.

The gene expression analysis revealed that C7R-promoted survival of GD2-CAR T-cells during repeated tumor cell challenges is correlated with an increase of BCL2 transcription and reduced expression of FAS and CASP8. This would suggest that C7R exerts a broad anti-apoptotic influence within CAR T-cells to decrease their susceptibility to AICD. Other potential benefits from C7R include resistance to immunosuppressive agents such as TGF-β within the tumor microenvironment (Pickup, 2013), as there is downregulation of TGF-βRII in GD2-CAR.C7R T-cells relative to GD2-CAR T-cells alone (FIG. 22).

In particular embodiments, C7R will not significantly increase the severity of cytokine release syndrome, based on the observation that C7R only modestly enhanced antigen-driven cytokine secretion by CAR T-cells. Furthermore, the low toxicity seen in a glioblastoma patient successfully treated with intraventricular IL-13Rα2 CAR T-cell infusions (Brown, 2016), together with the observation that C7R functionally enhanced EphA2-CAR T-cells without substantially increasing expansion in our orthotopic glioblastoma model, also suggests a low risk for adverse events if the CAR T-cell and C7R combination strategy was used for glioblastoma treatment. There was no evidence that C7R could induce antigen-independent proliferation, although the NSG model has obvious limitations for assessing the long-term fate of human T-cells in vivo. As added protection against both concerns, however, inclusion of a dimerizable iC9-mediated safety switch would allow deletion of CAR T-cells expressing C7R.

Given the effective application of C7R to GD2-CAR T-cells and EphA2-CAR T-cells against metastatic neuroblastoma and orthotopic glioblastoma, the C7R molecule (merely as an example) is useful to enhance many other CAR T-cells. In particular embodiments, this same approach increases the anti-tumor activity of other adoptive cell therapies for cancer including those based on the specificities of native (Dudley, 2008) or transgenic TCRs (Obenaus, 2015) as well as those exploiting the properties of NK and NKT-cells (Pellegrini, 2009), given that all respond to IL-7 supplementation.

Examples of Materials and Methods

Generation of Retroviral Vectors pSFG.ΔCD34-IL7R* (pSFG.C7R): A cDNA encoding a mutant IL-7Rα with a TTGTCCCAC insertion between base pairs 731 and 732 (IL7R*) (Zenatti et al., Nat Genet. 2011; 43:932-9) was synthesized (Genscript®, Piscataway, NJ). pSFG.C7R were generated by IN-Fusion® (Takara, Mountainview, CA) cloning using a XhoI and MluI-digested SFG vector backbone, the IL7R* cDNA, and the entire extracellular domain of CD34 (ΔCD34).

pSFG.GD2-CAR, pSFG.GD2-CAR-2A-C7R (GD2-CAR.C7R), and pSFG.GD2A-CAR-2A-C7R (GD2-CARΔ.C7R): A cDNA encoding a n-terminal leader peptide, the GD2-specific 14g2a single chain variable fragment (scFv), a CD8 stalk and transmembrane domain, and a 41BB.ξ endodomain was synthesized (Biobasic®, Marham, ON, Canada) and cloned by IN-Fusion® (Takara) cloning into a SFG retroviral vector upstream of an internal ribosomal entry site (IRES) and truncated NGFR. For pSFG.GD2-CAR-2A-C7R, the GD2-CAR was subcloned into a SFG vector upstream of a 2A sequence and C7R. For pSFG.GD2A-CAR-2A-C7R, the 2A-C7R was cloned downstream of a non-functional GD2-CAR available in the laboratory composed of the 14g2a scFv, a short IgG1 exodomain spacer, a CD28 transmembrane domain, and a truncated CD28 endodomain (RSKRSRLL; SEQ ID NO:26).

pSFG.EphA2-CAR-2A-CD19t (EphA2-CAR), pSFG.EphA2-CAR-2A-C7R (EphA2-CAR.C7R), and pSFG.EphA2-CARΔ-2A-C7R (EphA2-CARΔ.C7R): pSFG.EphA2-CAR-2A-CD19t encodes an EphA2-specific CAR consisting of the EphA2-specific 4H5 scFv (ref 25), a CD8 extracellular spacer, a CD8 transmembrane domain, a 41BB.ξ endodomain, a 2A sequence, and a truncated CD19 molecule (CD19t). pSFG.EphA2-CAR-2A-C7R was generated by IN-Fusion® (Takara) cloning replacing 2A-CD19t with 2A-C7R. For pSFG.EphA2-CARΔ-2A-C7R, 2A-C7R was cloned downstream of a non-functional EphA2-CAR which is composed of a EphA2-specific 4H5 scFv on the outside, a CD8 extracellular spacer, a CD8 transmembrane domain, and a truncated endodomain.

pSFG.iC9-2A-CD19t: The vector was generated as previously described elsewhere (Di Stasi, 2011).

All restriction enzymes were purchased from New England Biolabs Inc.® (Ipswich, MA) and the sequence of all cloned constructs was verified by Seqwright (Houston, TX).

T-Cell Generation

Peripheral blood mononuclear cells (PBMCs) from healthy donors were obtained to document under a Baylor College of Medicine IRB-approved protocol with informed consent obtained in accordance to the Declaration of Helsinki. When CD4 and CD8 T-cells were individually evaluated, PBMCs were labeled with CD4 or CD8 magnetic selection beads (Miltenyi, Auburn, CA) and positively selected following the manufacturer's instructions. For T-cell activation on day 0, bulk or selected T-cells were suspended in complete medium consisting of 90% RPMI 1640 (Hy clone, Logan, UT), 10% Fetal Bovine Serum (Hy clone), and 1% Glutamax (GIBCO® (microbiological culture media), Grand Island, NY), and cultured in wells coated with OKT3 (CRL-8001, American Type Culture Collection, Manassas, VA) and CD28 antibodies (BD Biosciences, San Jose, CA) for activation. IL-15 and IL-7 (PEPROTECH® (manufacturer of recombinant cytokines and growth factors), Rocky Hill, NJ) were added one day after activation, and cells were retrovirally transduced on day 2. T-cells were used for experiments beginning at 9-12 days after OKT3 and CD28 activation.

Flow Cytometry

Fluorochrome-conjugated antibodies were purchased from BIOLEGEND® (manufacturer of antibodies and reagents used in biomedical research) (San Diego, CA; CCR7, CD45RO, NGFR); ABNOVA® (manufacturer of antibodies, proteins, and kits), (Taoyuan City, Taiwan; CD34); THERMO FISHER SCIENTIFIC® (supplier of scientific instrumentation, and reagents) (Life Technologies, Frederick, MD; CD8); eBioscience (San Diego, CA; CD4); BECKMAN COULTER® (manufacturer of products for biomedical testing) (Indianapolis, IN; CD3), BD Biosciences (CD 8, CD4, CD3, CD34, Stat5 (pY694), Annexin V, 7-AAD). For surface staining, cells were incubated with antibodies for 15 minutes at 4 degrees C. Cells were acquired on a BECKMAN COULTER® (manufacturer of products for biomedical testing) Galios (10,000 events) and analysis was performed using Flowjo 10.0.7r2 (Tree Star, Ashland, OR). Proliferation analysis was performed using Flowjo 9.3.2 (Tree Star).

Cytotoxicity Assay

A 4-hour luciferase-based cytotoxicity assay was performed using the LAN-1 neuroblastoma cell line expressing GFP-Firefly luciferase (GFP-FFluc) based on a previously described protocol with minor modifications (Liu, 2013). Briefly, $2 \times 10^4$ LAN-1 neuroblastoma cells were plated per well in a 96 well black plate (Corning®, Corning, NY). 24 hours later, CAR T-cells were added in varying effector to target (E:T) ratios. The viable number of LAN-1 cells per well was determined using a standard curve generated by serial dilution of LAN-1 cells. The formula used to calculate the percent cytotoxicity is as follows: (Cell number in untreated well—Cell number in assay well)/(Cell number in untreated well).

Serial Tumor Challenge Assay 0.5×106 LAN-1 cells and 1×106 T-cells transduced with GD2-CAR or GD2-CAR.C7R were co-cultured in a 24 well plate using fresh culture media without IL-15 and IL-7. Seven days later, cells were harvested either for FACs analysis or for T-cell quantification by trypan-blue exclusion. CAR T-cells were then replated at a 2:1 E:T ratio with fresh LAN-1 cells in fresh cell culture media to start the second and third tumor cocultures. At the conclusion of the third co-culture, T-cells were counted and the coculture was analyzed by FACS.

Quantitative Flow Analysis

To count antibody-stained cells, following a PBS wash, 25 μL of counting beads (Life Technologies) and 2 μL of 7-AAD were added (for dead cell exclusion), and cells were immediately analyzed. Acquisition of events was based on collection of 3000 counting beads. Analysis of cytokine production.

Analysis of Cytokine Production

T-cells expressing GD2-CAR or GD2-CAR.C7R were cultured with LAN-1 cells using a 1:4 E:T ratio in a 24-well plate in complete culture medium without cytokines. 24 hours later, supernatants were harvested. IFN-γ and TNF-α release was quantitated using ELISA kits (R&D Systems®, Minneapolis, MN).

Phosphorylated-STAT5 Assay

Transduced T-cells were harvested and re-suspended at 0.5×106 cells/mL of complete medium without cytokines, then plated at 0.5×106 cells per well in a 48-well tissue cultured plate. 24-72 hours later, cells were harvested into a FACs tube and washed in cold flow buffer (PBS containing 5% FBS). 100 [iL of FIX & PERM™ (kit for fixing and permeabilizing cells in suspension) Reagent A (Life Technologies) was added to the cells, gently vortexed, and incubated for 3 minutes at room temperature before 3 mL of ice-cold methanol was slowly added to the tube with constant vortexing. The tubes were then incubated for 10 minutes at 4 degrees C. Afterwards, the tubes were centrifuged and the methanol was discarded, followed by another wash step with cold flow buffer. 100 μl^ of FIX & PERM™ (kit for fixing and permeabilizing cells in suspension) Reagent B (Life Technologies) and 5 uL of anti-STAT5 antibody were then added to the cells. The cells were gently vortexed then incubated in the dark for 30 minutes at room temperature. Afterwards, the cells were washed one more time with cold flow buffer and then immediately analyzed.

CELL TRACE® (Cell Monitoring System to Trace Multiple Cell Generations) Violet Proliferation Assay After a single co-culture with LAN-1 tumor cells, GD2-CAR T-cells and GD2-CAR.C7R T-cells were labeled with CELL TRACE® (cell monitoring system to trace multiple cell generations) Violet using the kit purchased from Thermo Fisher in accordance with the manufacturer's instructions. T-cells were then re-challenged with tumor cells for 1 week before analysis. 7-AAD was added to exclude dead cells.

Apoptosis Analysis

Cells were incubated with Annexin V antibody and 7-AAD, and analyzed by flow cytometry. For experiments with iC9, the chemical inducer of dimerization (CID), AP20187, was purchased from Takara Clontech®.

Cell Lines

LAN-1 and U373 were purchased from ATCC® (repository of authenticated cells lines and microorganisms) and used to generate LAN-1 GFP-FFluc and U373 GFP-FFluc. CHLA-255 and CHLA-255 FFluc were established and maintained as previously described (Liu, 2012, J Clin Invest. 2012 Jun. 1 122(6): 2221-223). Routine mycoplasma surveillance was performed using an enzyme-based assay (Lonza, Rockland, ME) and cells were authenticated within a year of the experiments described using STR profiling.

Gene Expression Analysis

Total RNA was collected using the QIAzol® reagent and the miRNeasy Micro Kit (Qiagen®, Germantown, MD). Gene expression analysis used the Immunology Panel version 2 (NanoString®, Seattle, WA) at the Baylor College of Medicine Genomic and RNA Profiling Core using the nCounter®Analysis System. Data was analyzed using nSolver 3.0 software (NanoString®).

In-Vivo Experiments

All animal experiments followed a protocol approved by the Baylor College of Medicine Institutional Animal Care and Use Committee.

Subcutaneous neuroblastoma mouse model: 10-14 week old female NSG mice were implanted subcutaneously in the dorsal left flank with 2 million LAN-1 neuroblastoma cells in 100 μL of basement membrane MATRIGEL® (solubilized basement membrane matrix) (Corning). 8 days later, mice were divided into groups based on tumor sizes such that the group tumor means and variances were similar. They were then injected intravenously with 1 million GD2-CAR T-cells (10-12 days after PBMC isolation). Tumor sizes were measured twice a week with calipers and the mice were imaged for bioluminescence signal from T-cells at the same time points using the IVIS® system (IVIS, Xenogen Corporation, Alameda, CA) 10-15 minutes after 150 mg/kg D-luciferin (Xenogen) per mouse was injected intraperitoneally. The mice were euthanized when the tumor diameter was equal to or greater than 15 mm, or when the tumor exceeded 10% of the mouse body weight.

Metastatic neuroblastoma mouse model: 10-14 week old female NSG mice were intravenously injected with 1 million Firefly-luciferase expressing CHLA-255 cells (CHLA-255 FFluc). 7 days later, mice were injected intravenously with 1 million GD2-CAR T-cells (10-12 days after PBMC isolation). In parallel experiments, tumor growth or T-cell expansion was indirectly assessed by weekly bioluminescent imaging as described above. In the experiments where tumor growth was tracked, mice groups were not standardized for tumor burden because CHLA-255 FFluc luminescence was not detectable at the time of T-cell injection.

Orthotopic glioblastoma mouse model: 105 U373 glioblastoma cells were established intracranially in 8-week-old male ICR-SCID mice as previously described (Chow, 2013, Mol Ther. 2013 March; 21(3): 629-637). 7 days after tumor engraftment, 104 T-cells were injected intracranially directly into tumors. Tumor growth or T-cell expansion was assessed by weekly bioluminescent imaging as described above. Mice in tumor growth experiments were standardized for tumor burden but not variances.

Statistical Analysis

Graphs and statistics were generated using Prism 5.0 software for Windows (Graphpad Software Inc., La Jolla, CA). Measurement data are presented as mean±standard error of the mean (SEM). The differences between means were tested using the paired two-tailed t-test. For the mouse experiments, changes in tumor radiance from baseline at each time point were calculated and compared between groups using a two-tailed paired t-test or Welch's t-test, when appropriate. 1-way ANOVA and Bartlett's test for equal variances was used when appropriate to ensure similar tumor means and variances between groups. Survival determined from the time of tumor cell injection was analyzed by the Kaplan-Meier method and differences in survival between groups were compared by the log-rank test.

What is claimed is:

1. A polynucleotide that encodes an engineered constitutively active receptor polypeptide, said polypeptide comprising the following components:
   a) an IL-7 cytokine receptor alpha chain endodomain;
   b) a transmembrane domain comprises the sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24; and
   c) one or more extracellular domains, wherein the extracellular domain is from PD-1, B7, CD30, HER2, EGFR, CD19, CD34, TGF-beta receptor, IL-4 receptor, IL-13 receptor alpha1 and alpha 2, IL-8 receptor, IL-10 receptor, LAG3, TIGIT, CTLA4, FAS, CD27, CD28, CD52, CD134, CD137, or NGFR.

2. A cell comprising the polynucleotide of claim 1.

3. The cell of claim 2, wherein the transmembrane domain is self-oligomerizing.

4. The cell of claim 2, wherein the extracellular domain is globular in form.

5. The cell of claim 2, wherein the extracellular domain comprises an extracellular domain from PD-1 or B7.

6. The cell of claim 2, wherein the extracellular domain is the extracellular domain of CD34.

7. The cell of claim 2, wherein the length of the extracellular domain, except CD52, is at least 70 amino acids.

8. The cell of claim 2, wherein the length of the extracellular domain is no more than 2000 amino acids.

9. The cell of claim 2, wherein the length of the extracellular domain is between 70-2000 amino acids.

10. The cell of claim 2, wherein the cell is an immune cell.

11. The cell of claim 2, wherein the cell is a T-cell, a NK cell, a NKT cell, αβ cell, γδ T-cell, a Mucosa Associated Invariant T-cell (MAIT T-cell), innate lymphoid cell, a stem cell, or a progenitor cell.

12. The cell of claim 2, wherein the cell comprises a non-natural molecule that confers antigen specificity for the cell.

13. The cell of claim 2, wherein the cell further comprises at least one additional engineered receptor.

14. The cell of claim 13, wherein the additional engineered receptor is a constitutively active cytokine receptor, a chimeric antigen receptor, a recombinant T-cell receptor, a bispecific T-cell engager, Dual-Affinity Re-Targeting protein, or a combination thereof.

15. The cell of claim 2, wherein the cell is a T-cell that comprises at least one chimeric antigen receptor.

16. The cell of claim 2, wherein the polynucleotide further comprises an expression vector.

17. The cell of claim 16, wherein the expression vector is a viral vector or a non-viral vector.

18. The cell of claim 17, wherein the viral vector is a retroviral, lentiviral, adenoviral, or adeno-associated viral vector.

19. A plurality of cells of claim 2, wherein the cells comprise a mixture of one or more of a T-cell, a NK cell, a NKT cell, an αβ T-cell, a γδ T-cell, a Mucosa Associated Invariant T-cell (MAIT T-cell), innate lymphoid cell, a stem cell, or a progenitor cell.

20. A plurality of cells of claim 2, wherein the cells comprise one or more immune effector cells.

21. The cell of claim 2, wherein the length of the extracellular domain is between 50-500 amino acids.

* * * * *

UNITED STATES PATENT AND TRADEMARK OFFICE
CERTIFICATE OF CORRECTION

| | |
|---|---|
| PATENT NO. | : 12,102,652 B2 |
| APPLICATION NO. | : 16/326270 |
| DATED | : October 1, 2024 |
| INVENTOR(S) | : Shum et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1128 days.

Signed and Sealed this
Third Day of December, 2024

Katherine Kelly Vidal
*Director of the United States Patent and Trademark Office*